(12) United States Patent
Schnittman et al.

(10) Patent No.: US 9,233,471 B2
(45) Date of Patent: *Jan. 12, 2016

(54) DEBRIS MONITORING

(71) Applicant: iRobot Corporation, Bedford, MA (US)

(72) Inventors: Mark Steven Schnittman, Somerville, MA (US); Michael Todd Rosenstein, Westford, MA (US)

(73) Assignee: iRobot Corporation, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,440

(22) Filed: Apr. 22, 2014

(65) Prior Publication Data

US 2014/0229008 A1 Aug. 14, 2014

Related U.S. Application Data

(63) Continuation of application No. 13/340,784, filed on Dec. 30, 2011, now Pat. No. 8,742,926.

(60) Provisional application No. 61/428,808, filed on Dec. 30, 2010.

(51) Int. Cl.
*G08B 21/00* (2006.01)
*B25J 11/00* (2006.01)
(Continued)

(52) U.S. Cl.
CPC ............ *B25J 11/0085* (2013.01); *A47L 9/106* (2013.01); *A47L 9/19* (2013.01); *A47L 9/2826* (2013.01); *A47L 9/2842* (2013.01); *A47L 9/2894* (2013.01); *A47L 11/4013* (2013.01);
(Continued)

(58) Field of Classification Search
CPC .... A47L 9/2842; A47L 2201/024; A47L 9/19
USPC ......................... 340/540; 15/319, 339, 340.1; 318/568.1; 700/245, 250
See application file for complete search history.

(56) References Cited

U.S. PATENT DOCUMENTS

| 4,401,909 A | 8/1983 | Gorsek |
| 4,674,048 A | 6/1987 | Okumura |

(Continued)

FOREIGN PATENT DOCUMENTS

| CN | 101036568 A | 9/2007 |
| EP | 1331537 A1 | 7/2003 |

(Continued)

OTHER PUBLICATIONS

Authorized Officer R. Stadlmeyer, PCT International Search Report and Written Opinion for International Application No. PCT/US2011/068119 issued May 4, 2012, 11 pages.
International Preliminary Report on Patentability issued in International Application No. PCT/US2011/068119, issued Jul. 2, 2013, 7 pages.

*Primary Examiner* — John A Tweel, Jr.
(74) *Attorney, Agent, or Firm* — Fish & Richardson P.C.

(57) ABSTRACT

A debris monitoring system includes a receptacle, a first and a second emitter, and a first receiver. The receptacle defines an opening to receive debris into the receptacle. The first and second emitter are each arranged to emit a signal across at least a portion of the opening. The first receiver is proximate to the first emitter to receive reflections of the signal emitted by the first emitter, and the first receiver is disposed toward the opening to receive an unreflected portion of the signal emitted by the second emitter across at least a portion of the opening.

14 Claims, 33 Drawing Sheets

(51) Int. Cl.
*A47L 9/10* (2006.01)
*A47L 9/19* (2006.01)
*A47L 9/28* (2006.01)
*A47L 11/40* (2006.01)
*G01N 21/47* (2006.01)
*G05D 1/02* (2006.01)

(52) U.S. Cl.
CPC ........ *A47L 11/4025* (2013.01); *A47L 11/4041* (2013.01); *G01N 21/47* (2013.01); *G05D 1/0225* (2013.01); *G05D 1/0234* (2013.01); *A47L 2201/00* (2013.01); *A47L 2201/02* (2013.01); *A47L 2201/024* (2013.01); *A47L 2201/06* (2013.01); *G05D 2201/0215* (2013.01)

(56) References Cited

U.S. PATENT DOCUMENTS

| | | | |
|---|---|---|---|
| 4,918,441 A | 4/1990 | Bohman | |
| 4,920,605 A | 5/1990 | Takashima | |
| 4,961,304 A | 10/1990 | Ovsborn et al. | |
| 5,023,788 A | 6/1991 | Kitazume et al. | |
| 5,109,566 A | 5/1992 | Kobayashi et al. | |
| 5,163,202 A | 11/1992 | Kawakami et al. | |
| 5,216,777 A | 6/1993 | Moro et al. | |
| 5,233,682 A | 8/1993 | Abe et al. | |
| 5,251,358 A | 10/1993 | Moro et al. | |
| 5,284,522 A | 2/1994 | Kobayashi et al. | |
| 5,341,540 A | 8/1994 | Soupert et al. | |
| 5,352,901 A | 10/1994 | Poorman | |
| 5,369,347 A | 11/1994 | Yoo | |
| 5,410,479 A | 4/1995 | Coker | |
| 5,507,067 A | 4/1996 | Hoekstra et al. | |
| 5,515,572 A | 5/1996 | Hoekstra et al. | |
| 5,539,953 A | 7/1996 | Kurz | |
| 5,542,146 A | 8/1996 | Hoekstra et al. | |
| 5,568,589 A | 10/1996 | Hwang | |
| 5,613,261 A | 3/1997 | Kawakami et al. | |
| 5,652,489 A | 7/1997 | Kawakami | |
| 5,722,109 A | 3/1998 | Delmas et al. | |
| 5,815,884 A | 10/1998 | Imamura et al. | |
| 5,910,700 A | 6/1999 | Crotzer | |
| 5,935,179 A | 8/1999 | Kleiner et al. | |
| 5,942,869 A | 8/1999 | Katou et al. | |
| 5,959,423 A | 9/1999 | Nakanishi et al. | |
| 6,055,702 A | 5/2000 | Imamura et al. | |
| 6,076,226 A | 6/2000 | Reed | |
| 6,076,227 A | 6/2000 | Schallig et al. | |
| 6,124,694 A | 9/2000 | Bancroft et al. | |
| 6,142,252 A | 11/2000 | Kinto et al. | |
| 6,167,332 A | 12/2000 | Kurtzberg et al. | |
| 6,178,590 B1 * | 1/2001 | Lindsay et al. | 15/327.1 |
| 6,278,918 B1 | 8/2001 | Dickson et al. | |
| 6,285,930 B1 | 9/2001 | Dickson et al. | |
| 6,323,570 B1 | 11/2001 | Nishimura et al. | |
| 6,327,741 B1 | 12/2001 | Reed | |
| 6,385,515 B1 | 5/2002 | Dickson et al. | |
| 6,389,329 B1 | 5/2002 | Colens | |
| 6,400,048 B1 | 6/2002 | Nishimura et al. | |
| 6,437,465 B1 | 8/2002 | Nishimura et al. | |
| 6,459,955 B1 | 10/2002 | Bartsch et al. | |
| 6,481,515 B1 | 11/2002 | Kirkpatrick et al. | |
| 6,490,539 B1 | 12/2002 | Dickson et al. | |
| 6,532,404 B2 | 3/2003 | Colens | |
| 6,615,108 B1 | 9/2003 | Peless et al. | |
| 6,671,592 B1 | 12/2003 | Bisset et al. | |
| 6,690,134 B1 | 2/2004 | Jones et al. | |
| 6,732,826 B2 | 5/2004 | Song et al. | |
| 6,801,015 B2 | 10/2004 | Bertram et al. | |
| 6,809,490 B2 | 10/2004 | Jones et al. | |
| 6,810,305 B2 | 10/2004 | Kirkpatrick | |
| 6,841,963 B2 | 1/2005 | Song et al. | |
| 6,956,348 B2 | 10/2005 | Landry et al. | |
| 6,968,592 B2 | 11/2005 | Takeuchi et al. | |
| 7,024,278 B2 | 4/2006 | Chiappetta et al. | |
| 7,066,291 B2 | 6/2006 | Martins et al. | |
| 7,113,847 B2 | 9/2006 | Chmura et al. | |
| 7,166,983 B2 | 1/2007 | Jung | |
| 7,167,775 B2 | 1/2007 | Abramson et al. | |
| 7,188,000 B2 | 3/2007 | Chiappetta et al. | |
| 7,233,122 B2 | 6/2007 | Kim et al. | |
| 7,251,853 B2 | 8/2007 | Park et al. | |
| 7,320,149 B1 | 1/2008 | Huffman et al. | |
| 8,742,926 B2 * | 6/2014 | Schnittman et al. | 340/540 |
| 2002/0116089 A1 | 8/2002 | Kirkpatrick | |
| 2002/0120364 A1 | 8/2002 | Colens | |
| 2003/0025472 A1 | 2/2003 | Jones et al. | |
| 2003/0026472 A1 | 2/2003 | Abe et al. | |
| 2003/0060928 A1 | 3/2003 | Abramson et al. | |
| 2003/0097875 A1 | 5/2003 | Lentz et al. | |
| 2003/0120389 A1 | 6/2003 | Abramson et al. | |
| 2003/0146739 A1 | 8/2003 | Bertram et al. | |
| 2004/0045117 A1 | 3/2004 | Alowonle et al. | |
| 2004/0049877 A1 | 3/2004 | Jones et al. | |
| 2004/0111184 A1 | 6/2004 | Chiappetta et al. | |
| 2004/0187249 A1 | 9/2004 | Jones et al. | |
| 2004/0204792 A1 | 10/2004 | Taylor et al. | |
| 2004/0211444 A1 | 10/2004 | Taylor et al. | |
| 2004/0236468 A1 | 11/2004 | Taylor et al. | |
| 2004/0244138 A1 | 12/2004 | Taylor et al. | |
| 2005/0022330 A1 | 2/2005 | Park et al. | |
| 2005/0138764 A1 | 6/2005 | Grey | |
| 2005/0150074 A1 | 7/2005 | Diehl et al. | |
| 2005/0162119 A1 | 7/2005 | Landry et al. | |
| 2005/0163119 A1 | 7/2005 | Ito et al. | |
| 2005/0166355 A1 | 8/2005 | Tani | |
| 2005/0171644 A1 | 8/2005 | Tani | |
| 2005/0183229 A1 | 8/2005 | Uehigashi | |
| 2005/0204505 A1 | 9/2005 | Kashiwagi | |
| 2005/0212478 A1 | 9/2005 | Takenaka | |
| 2005/0212680 A1 | 9/2005 | Uehigashi | |
| 2005/0234595 A1 | 10/2005 | Tani | |
| 2006/0056677 A1 | 3/2006 | Tani | |
| 2006/0238157 A1 | 10/2006 | Kim et al. | |
| 2006/0238159 A1 | 10/2006 | Jung | |
| 2006/0241814 A1 | 10/2006 | Jung | |
| 2006/0253224 A1 | 11/2006 | Tani et al. | |
| 2006/0259212 A1 | 11/2006 | Jeon | |
| 2007/0096676 A1 | 5/2007 | Im et al. | |
| 2010/0293742 A1 | 11/2010 | Chung et al. | |

FOREIGN PATENT DOCUMENTS

| | | |
|---|---|---|
| EP | 1836941 | 9/2007 |
| JP | 53110257 A | 9/1978 |
| JP | 59131668 A2 | 7/1984 |
| JP | 62189057 | 8/1987 |
| JP | 04084921 A | 3/1992 |
| JP | 4300516 | 10/1992 |
| JP | H05-095879 A | 4/1993 |
| JP | 6038912 | 2/1994 |
| JP | 7281752 | 10/1995 |
| JP | H08-038408 A | 2/1996 |
| JP | 10165738 | 6/1998 |
| JP | 2000-060782 A | 2/2000 |
| JP | 2001-504744 A | 4/2001 |
| JP | 2002-078650 A | 3/2002 |
| JP | 2002-204769 A | 7/2002 |
| JP | 2002-369778 A | 12/2002 |
| JP | 2003 310489 | 11/2003 |
| JP | 2007-244467 A | 9/2007 |
| JP | 2007-244711 A | 9/2007 |
| JP | 2008-301878 | 12/2008 |
| JP | 2009-254603 | 11/2009 |
| JP | 2012-200461 | 10/2012 |
| WO | 95/30887 | 11/1995 |
| WO | 2007137234 | 11/2007 |

* cited by examiner

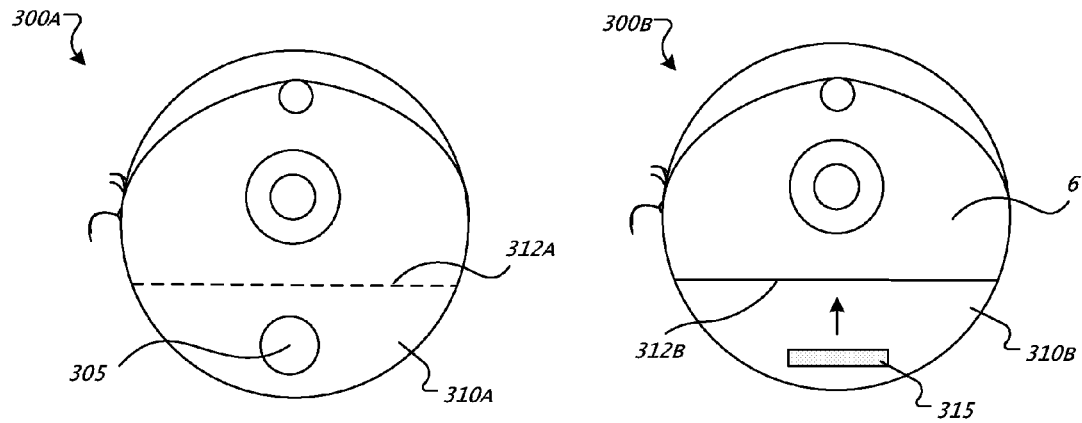
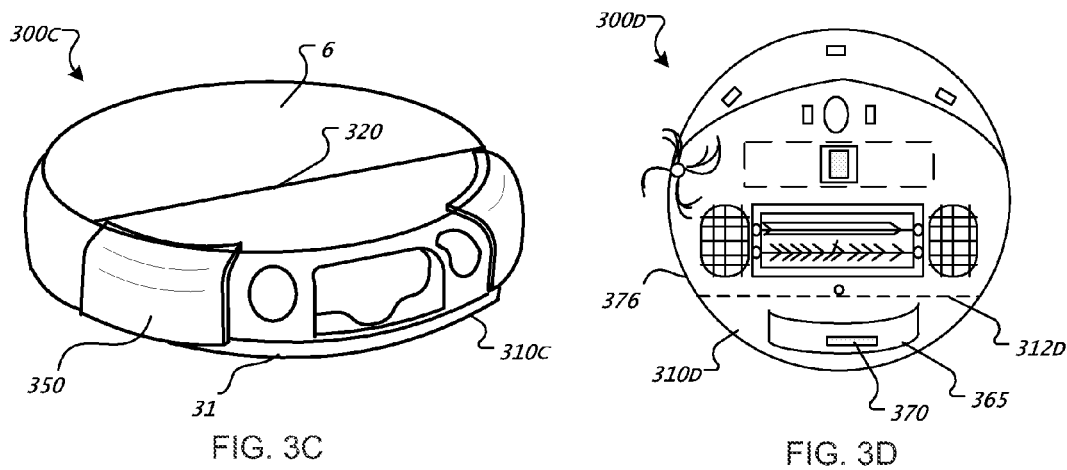
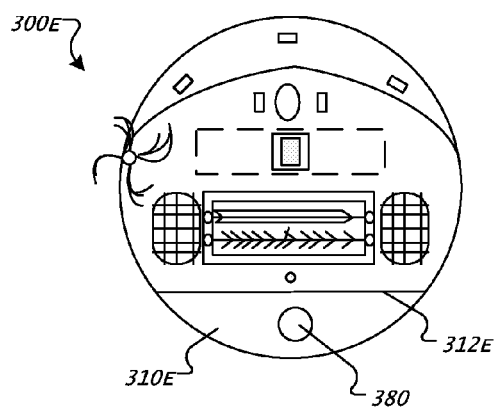

DEBRIS MONITORING

CLAIM OF PRIORITY

This U.S. patent application is a continuation of and claims priority to U.S. patent application Ser. No. 13/340,784, filed on Dec. 30, 2011 which claims priority under 35 U.S.C. §119(e) to U.S. Provisional Application 61/428,808, filed on Dec. 30, 2010, the disclosure of each of which are considered part of the disclosure of this application and are hereby incorporated by reference in its entirety.

TECHNICAL FIELD

This application relates to robots, and more particularly to autonomous coverage robots.

BACKGROUND

Autonomous robots can perform desired tasks in unstructured environments without continuous human guidance. Many kinds of robots are autonomous to some degree. Different robots can be autonomous in different ways. An autonomous coverage robot can traverse a work surface without continuous human guidance to perform one or more tasks. In the field of home, office and/or consumer-oriented robotics, mobile robots that perform household functions such as removing debris from a surface (e.g., vacuum cleaning and floor washing) have been widely adopted.

SUMMARY

In one aspect, a debris monitoring system includes a receptacle, a first and a second emitter, and a first receiver. The receptacle defines an opening to receive debris into the receptacle. The first and second emitter are each arranged to emit a signal across at least a portion of the opening. The first receiver is proximate to the first emitter to receive reflections of the signal emitted by the first emitter, and the first receiver is disposed toward the opening to receive an unreflected portion of the signal emitted by the second emitter across at least a portion of the opening.

In another aspect, a coverage robot includes a housing, a drive system, a cleaning assembly, a receptacle, a first and a second emitter, and a first receiver. The drive system is coupled to the housing and configured to maneuver the robot across a cleaning surface. The cleaning assembly is coupled to the housing. The receptacle is disposed substantially within the housing, and the receptacle defines an opening to receive debris into the receptacle from the cleaning assembly. The debris monitoring system is disposed substantially within the housing. The debris monitoring system includes a first and a second emitter and a first receiver. The first and second emitter are each arranged to emit a signal across at least a portion of the opening. The first receiver proximate to the first emitter to receive reflections of the signal emitted by the first emitter and the first receiver disposed toward the opening to receive an unreflected portion of the signal emitted by the second emitter across at least a portion of the opening.

Implementations of one or more of these aspects of the disclosure may include one or more of the following features. In some implementations, the first receiver and the second emitter are disposed substantially opposite one another across the largest dimension of the opening. The opening can be substantially rectangular. Additionally or alternatively, the first receiver and the second receiver can be substantially diagonally opposed to one another across the opening. In certain implementations, the first and second emitters are arranged relative to one another such that the respective signals emitted by the first and second emitters intersect along at least a portion of the opening. The opening can be defined in a substantially vertical plane as debris is received into the receptacle.

In certain implementations, the opening has a top portion and a bottom portion, the top portion above the bottom portion as debris is received into the receptacle, and the first and second emitters and the first receiver each disposed toward a top portion of the opening, with the first receiver disposed above the first and second emitters.

In some implementations, the first receiver is arranged about 0.5 inches to about 30 inches from the second emitter. The first receiver can be less than about 5 inches from the first emitter. Additionally or alternatively, the ratio of the distance between the first receiver and the second emitter to the distance between the first receiver and the first emitter is about 0.1 to about 600.

In certain implementations, the receptacle is releasably engageable with a housing configured to support the receptacle as debris is received through the opening of the receptacle. The first and second emitters and the first receiver can each be supported on the housing and the receptacle can be movable relative to the first and second emitters and the first receiver. The first and second emitters and the first receiver can each be supported on the receptacle. A controller can be supported on the housing. The first and second emitters and the first receiver can each be in wireless communication (e.g., infrared communication) with the controller.

In some implementations, the receptacle is removable from a side portion of the coverage robot when the robot is on the cleaning surface and/or removable from a side portion of the housing. Additionally or alternatively, the receptacle is removable from a top portion of the coverage robot when the robot is on the cleaning surface and/or removable from a top portion of the housing.

In another aspect, a debris monitoring system includes a receptacle, a plurality of first emitters and a plurality of second emitters, a first receiver, and a second receiver. The receptacle defines an opening to receive debris into the receptacle. Each emitter of each plurality of emitters is arranged to emit a signal across at least a portion of the opening. The first receiver is proximate to the plurality of first emitters to receive reflections of the signal emitted by each of the plurality of first emitters and the first receiver is disposed toward the opening to receive an unreflected portion of the signal emitted by each of the plurality of second emitters across at least a portion of the opening. The second receiver is proximate to the plurality of second emitters to receive reflections of the signal emitted by each of the plurality of second emitters and the second receiver disposed toward the opening to receive an unreflected portion of the signal emitted by each of the plurality of first emitters across at least a portion of the opening.

Implementations of this aspect of the disclosure may include one or more of the following features. In some implementations, a controller is configured to pulse the plurality of first emitters on and off and to pulse the plurality of second emitters on and off. The controller can be configured to sample each of the first and second receivers synchronously such that a first sample of each receiver is taken when the plurality of first emitters and the plurality of second emitters are off, a second sample of each receiver is taken when the plurality of first emitters is on and the plurality of second emitters is off, and a third sample of each receiver is taken when the plurality of first emitters is off and the plurality of second emitters is on.

In certain implementations, the plurality of first emitters and the plurality of second emitters are arranged relative to one another such that the signals emitted by the plurality of first emitters intersect the signals emitted by the plurality of second emitters. The intersection can be along at least a portion of the opening. The plurality of first emitters and the plurality of second emitters can be arranged relative to one another such that the signals emitted by the plurality of first emitters intersect the signals emitted by the plurality of second emitters along a line substantially bisecting the opening.

In some implementations, the plurality of first emitters and the plurality of second emitters are spaced relative to one another such that the signals emitted by the plurality of first emitters and the plurality of second emitters span substantially all (e.g., more than 50 percent) of the area of the opening when all of the emitters from each of the plurality of first and second emitters are on.

In yet another aspect, a debris monitoring method includes activating and deactivating a first emitter and a second emitter, measuring a first receiver disposed proximate to the first emitter, and detecting movement of debris through the opening. The first emitter and the second emitter are activated to emit respective signals at a substantially constant frequency across an opening defined by a receptacle. The first receiver is disposed proximate to the first emitter to receive a reflected portion of the signal from the first emitter and disposed relative to the second emitter to receive an unreflected portion of the signal from the second emitter. The detection of movement of debris through the opening is based at least in part on a first measurement obtained when the first and second emitters are each deactivated, a second measurement obtained when the first emitter is activated and the second emitter is deactivated, and a third measurement is obtained when the first emitter is deactivated and the second emitter is activated.

Implementations of this aspect of the disclosure may include one or more of the following features. In some implementations, detecting movement of debris through the opening includes processing the first, second, and third measurements as a function of time and detecting changes in at least one of the processed second and third measurements. In certain implementations, detecting movement of debris through the opening includes filtering ambient light from the second and third measurements based at least in part on the first measurement. The first, second, and third measurements can be processed as a function of time (e.g., by low pass filtering at least one of the second and third measurements). In some implementations, detecting changes in at least one of the processed second and third measurements includes comparing the instantaneous change to an average value of the respective processed measurement.

In certain implementations, the debris monitoring method includes determining the amount of light blocked by debris passing through the opening and periodically assigning a score to the debris based at least in part on the determined amount of light blocked by the debris. Determining the amount of light blocked by debris passing through the opening can be based at least on in part the second or third measurement.

In some implementations, the debris monitoring method includes summing consecutive debris scores and providing a dirt detection signal if the sum of the debris scores exceeds a threshold value. The sum of the debris score can be decremented over time. The amount of the decrement can be based at least in part on a running average value of the debris scores.

In still another aspect, a debris monitoring method including activating and deactivating a first emitter and a second emitter to emit respective signals across an opening defined by a receptacle, measuring a first receiver, and determining whether a receptacle is full of debris. The first receiver is disposed proximate to the first emitter to receive a reflected portion of the signal from the first emitter and disposed relative to the second emitter to receive an unreflected portion of the signal from the second emitter. The determination of whether the receptacle is full of debris is based at least in part on comparing a first reflective signal to a first transmissive signal. The first reflective signal is derived from a measurement by the first receiver when the first emitter is activated and the second emitter is deactivated and first transmissive signal derived from a measurement by the first receiver when the first emitter is deactivated and the second emitter is activated.

Implementations of this aspect of the disclosure may include one or more of the following features. In some implementations, determining whether a receptacle is full of debris includes setting a first threshold based at least in part on a comparison of the first reflective signal to the first transmissive signal. The first threshold can be set based in part on the first reflective signal and the first transmissive signal reaching a first crossover point at which the first reflective signal changes from being less than the first transmissive signal to being greater than or equal to the first transmissive signal. The first threshold can be set to a value greater than the value of the first reflective signal at the first crossover point. Additionally or alternatively, the first threshold value can be based at least in part on one or more of the following: the value of the first crossover point and the rate at which the first reflective signal reached the first crossover point. The first threshold can be reset if the first reflective signal falls below the first crossover point after the threshold has been set.

In some implementations, the debris monitoring method includes decrementing the threshold over time until the first reflective signal is greater than the first threshold. In certain implementations, the debris monitoring method includes generating a receptacle-full signal if the first reflective signal and the first transmissive signal are each about zero.

In some implementations, the debris monitoring method includes measuring a second receiver disposed proximate to the second emitter to receive a reflected portion of the signal from the second emitter and disposed relative to the first emitter to receive an unreflected portion of the signal from the second emitter. Determining whether a receptacle is full of debris can include comparing a second reflective signal, derived from a measurement by the second receiver when the second emitter is activated and the first emitter is deactivated, to a second transmissive signal, derived from a measurement by the second receiver when the second emitter is deactivated and the first emitter is activated. Determining whether a receptacle is full of debris can include setting a second threshold based at least in part on a comparison of the second reflective signal to the second transmissive signal. Additionally or alternatively, the debris monitoring method includes generating a receptacle-full signal if the first and second reflective signals each exceed the respective first and second thresholds.

In yet another aspect, a debris monitoring method includes maneuvering an autonomous coverage robot across a cleaning surface, activating and deactivating a first emitter and a second emitter, measuring a first receiver, receiving a signal from the first receiver, detecting movement of the debris through the opening based at least in part on the received signal, and determining whether a receptacle is full of debris based at least in part on the received signal. The robot carries a cleaning assembly and the receptacle arranged relative to the cleaning assembly to receive debris removed from the cleaning surface by the cleaning assembly. The first and second emitter are activated and deactivated to emit respective signals across an opening defined by the receptacle. The first receiver is disposed proximate to the first emitter to receive a reflected portion of the signal from the first emitter and disposed relative to the second emitter to receive an unreflected portion of the signal from the second emitter. Receiving the signal from the first receiver includes receiving a dark signal derived from a measurement by the first receiver when the first emitter is deactivated and the second emitter is deactivated, receiving a reflective signal derived from a measurement by the first receiver when the first emitter is activated and the second emitter is deactivated, and receiving a transmissive signal derived from a measurement by the first receiver when the first emitter is deactivated and the second emitter is activated. Detecting movement of debris through the opening is based at least in part on the dark signal, the reflective signal, and the transmissive signal, and determining whether a receptacle is full of debris is based at least in part on the reflective signal and the transmissive signal.

Implementations of this aspect of the disclosure may include one or more of the following features. In some implementations, movement of the robot is altered based at least in part upon detecting movement of debris through the opening. Altering movement of the robot can include initiating a spot coverage cleaning pattern. For example, initiating a spot coverage cleaning pattern can include immediately altering the direction of travel of the robot toward the detected debris. The spot coverage pattern can include one or more of the following: a spiral pattern, a star pattern, and a cornrow pattern. In some implementations, at least one dimension of the spot coverage pattern is at least partly based on a change in detected movement of debris through the opening. Additionally or alternatively, altering movement of the robot includes changing at least one of the following: direction of travel of the robot and speed of travel of the robot.

In certain implementations, the debris monitoring method includes altering movement of the robot based at least in part upon determining that the receptacle is full of debris. Altering movement of the robot can include moving the robot toward an evacuation station configured to engage the receptacle. In some implementations, the debris monitoring method includes deactivating the cleaning assembly based at least in part upon determining that the receptacle is full of debris.

In still another aspect, an autonomous coverage robot includes a robot body having a forward portion and a rear portion, right and left driven wheels, a debris agitator carried by the robot body, a first and a second cliff sensor, and a controller in communication with the right and left driven wheels and the first and second cliff sensors. The right and left driven wheels define a transverse axis between the forward portion and the rear portion of the robot body and each driven wheel is rotatable about the transverse axis. The debris agitator is configured to remove debris from the cleaning surface. The first cliff sensor is disposed forward of the transverse axis and the second cliff sensor is disposed rear of the transverse axis. The controller is configured to alter the direction of travel of the robot based at least in part on signals received from the first and second cliff sensors.

Implementations of this aspect of the disclosure may include one or more of the following features. In some implementations, comprising a waste receptacle carried by the robot body and in fluid communication with the debris agitator to receive the debris removed from the cleaning surface. At least a portion of the waste receptacle can be disposed within the robot body. Additionally or alternatively, the waste receptacle can be carried on the rear portion of the robot body.

In certain implementations, the waste receptacle is releasably engageable with the robot body and the second cliff sensor is disposed on the waste receptacle. The controller can be in wireless communication with the second cliff sensor, and this wireless communication can include one or more of the following: optical communication, electromagnetic communication, and radiofrequency communication.

In some implementations, a first electrical contact is disposed on the waste receptacle and a second electrical contact is carried on the robot body, wherein the first electrical contact is releasably engageable with the second electrical contact to establish electrical communication between the second cliff sensor and the controller. The controller can be configured to disable the right and left driven wheels if communication with the second cliff sensor is interrupted.

In certain implementations, the autonomous coverage robot includes a third cliff sensor disposed rear of the transverse axis. The third cliff sensor can be proximate to the waste receptacle. Additionally or alternatively, the second cliff sensor is proximate to the waste receptacle.

In some implementations, the first cliff sensor and the second cliff sensor define a fore-aft axis substantially perpendicular to the transverse axis. In certain implementations, the debris agitator extends substantially parallel to the transverse axis.

In another aspect, a waste receptacle for an autonomous coverage robot for removing debris from a cleaning surface includes a housing releasably engageable with a robot body of the autonomous coverage robot and a cliff sensor supported on the housing. The housing defines a volume for containing debris, and the housing defines an opening for receiving debris removed from the cleaning surface. The cliff sensor is arranged to detect a potential cliff while the housing is releasably engaged with the robot body and the robot removes debris from the cleaning surface.

Implementations of this aspect of the disclosure may include one or more of the following features. In some implementations, at least a portion of the housing defines at least a portion of a perimeter of the autonomous coverage robot while the housing is releasably engaged with the robot body. Additionally or alternatively, at least a portion of the housing defines at least a portion of a surface of the autonomous coverage robot substantially opposite the cleaning surface when the robot removes debris from the cleaning surface. In some implementations, at least a portion of the housing defines at least a portion of a surface of the autonomous coverage robot substantially perpendicular to the cleaning while the robot removes debris from the cleaning surface.

In certain implementations, the cliff sensor is supported on the portion of the housing defining at least a portion of the perimeter of the autonomous coverage robot. The housing can have a substantially arcuate portion and the cliff sensor can be disposed along the substantially arcuate portion. The substantially arcuate portion can be opposite the opening for receiving debris removed from the cleaning surface.

In some implementations, the housing has a dimension of less than about ten inches in a direction substantially perpendicular to the cleaning surface when the housing is releasably engaged with the robot body and the robot removes debris from the cleaning surface.

In certain implementations, an electrical contact is supported on the housing and in electrical communication with the cliff sensor, the electrical contact configured for releasable engagement with an electrical contact supported on the robot body. In some implementations, an optical emitter supported on the housing and in electrical communication with the cliff sensor, the optical emitter configured for optical communication with an optical receiver supported on the robot body.

In another aspect, a method of maneuvering an autonomous coverage robot includes receiving a signal from a first cliff sensor, receiving a signal from a second cliff sensor, and driving the right and left driven wheels to move the robot in a direction substantially opposite a detected potential cliff. The first cliff sensor is arranged to detect a potential cliff forward of a transverse axis defined by right and left driven wheels of the robot. The transverse axis is substantially perpendicular to the fore-aft direction of travel of the robot. The second cliff sensor is arranged to detect a potential cliff aft of the transverse axis.

Implementations of this aspect of the disclosure may include one or more of the following features. In some implementations, receiving the signal from the second cliff sensor includes receiving a wireless signal from the second cliff sensor. Additionally or alternatively, receiving the signal from the second cliff sensor includes receiving at least a portion of the signal through a releasably engageable electrical contact.

In certain implementations, the first cliff sensor is disposed along the substantially forward-most portion of the robot and the second cliff sensor is disposed along the substantially rear-most portion of the robot. In some implementations, whether the second cliff sensor is present is determined and the right and left driven wheels are disabled if the second cliff detector is not present. In certain implementations, driving the right and left driven wheels to move the robot in a direction substantially opposite a detected potential cliff includes moving the robot a distance greater than the distance between the right and left drive wheels along the transverse axis.

In yet another aspect, a method of operating an autonomous cleaning apparatus includes controlling a drive system of the cleaning apparatus to move the cleaning apparatus over a cleaning surface, receiving a signal from a debris sensor of the cleaning apparatus, and moving the cleaning apparatus through a pattern of movement based at least in part on the received debris signal. The signal from the debris sensor indicates that the cleaning apparatus is collecting debris. The pattern of movement includes a plurality of swaths.

Implementations of this aspect of the disclosure may include one or more of the following features. In some implementations, each of the plurality of swaths is substantially parallel to one another. In certain implementations, each of the plurality of swaths extends from a central region in a star pattern. The central region can be an area of the cleaning surface corresponding substantially to a local maximum of the received debris signal. The star pattern can radiate through an angle of about 360 degrees.

In certain implementations, at least a portion of at least some of the plurality of swaths overlap one another. In some implementations, the amount of overlap between swaths can be adjusted based at least in part on the magnitude of the debris signal. Additionally or alternatively, the number of swaths can be based at least in part on the signal from the debris sensor. In certain implementations, adjusting the number of swaths includes adjusting the number of swaths in proportion to the magnitude of the debris signal.

In some implementations, the length of each swath is adjusted based at least in part on the signal from the debris sensor. Additionally or alternatively, each swath can be terminated when the debris signal falls below a threshold. In certain implementations, the debris sensor is an optical sensor disposed in a cleaning pathway of the cleaning apparatus. The debris sensor can include an optical sensor disposed on a waste receptacle releasably engageable with the cleaning apparatus. Additionally or alternatively, debris sensor comprises a piezoelectric sensor element.

In another aspect, a method of operating an autonomous cleaning apparatus includes controlling a drive system of the cleaning apparatus to move the cleaning apparatus over a cleaning surface, receiving a signal from a debris sensor of the cleaning apparatus, moving the cleaning apparatus along the heading in the direction of the detected debris. The signal corresponds to a heading in the direction of detected debris.

Implementations of this aspect of the disclosure may include one or more of the following features. In some implementations, the debris sensor includes a camera directed substantially forward of the cleaning apparatus. In certain implementations, the camera is movable to scan an area substantially forward of the cleaning apparatus. Additionally or alternatively, the size of the debris is determined and the cleaning apparatus is moved away from debris larger than a threshold size.

In another aspect, a method of navigating an autonomous coverage robot includes maneuvering an autonomous coverage robot over a surface, detecting a first change in a signal emitted from a maintenance station configured to receive the autonomous coverage robot, detecting a second change in the signal from the maintenance station, and determining the probability that the robot will find the maintenance station in a period of time. The determined probability is based at least in part on an elapsed time between the detected first change in the signal and the detected second change in the signal.

Implementations of this aspect of the disclosure may include one or more of the following features. In some implementations, determining the probability that the robot will find the maintenance station in the period of time includes updating a probability distribution based at least in part on the elapsed time. The probability distribution can be a non-parametric model (e.g., a histogram). Additionally or alternatively, the probability distribution can be a parametric model, such as a Poisson distribution in which the mean of the Poisson distribution is estimated (e.g., as an average).

In some implementations, the method of navigating an autonomous coverage robot further includes determining the probability that power available from a battery carried by the robot will be depleted before the robot can find the maintenance station. In certain implementations, a period of time is allotted for finding the maintenance station. The allotted period of time can be based at least in part on the determined probability that the robot will find the maintenance station in the allotted period of time. In some examples, the power to the robot is reduced during the allotted period of time. For example, reducing the power can include reducing power to a cleaning assembly carried by the robot.

In certain implementations, the method of navigating an autonomous coverage robot further includes detecting whether the robot has been removed from the surface and ignoring the detected first change in the signal occurring just prior to detection that the robot has been removed from the surface and ignoring the detected second change in the signal occurring just after detection that the robot has been removed from the surface. For example, detecting that the robot has been removed from the surface can include receiving a signal from one or more sensors (e.g., wheel drop sensors and/or cliff detectors) carried by the robot.

In certain implementations, releasable contact between the robot and the maintenance station is established. Upon establishing releasable contact between the robot and the maintenance station, a battery carried by the robot can be charged.

In yet another aspect, a method of navigating an autonomous coverage robot includes maneuvering an autonomous coverage robot over a surface, detecting a first structure disposed along the surface, detecting a second structure disposed along the surface, determining the probability that the robot will find the first structure in a period of time, wherein the determined probability is based at least in part on detecting the second structure and an elapsed time between the detecting the first structure and detecting the second structure.

Implementations of this aspect of the disclosure may include one or more of the following features. The first structure can be a maintenance station configured to receive the robot and the second structure is a lighthouse. Additionally or alternatively, the first structure can be a first lighthouse and the second structure is a second lighthouse.

In still another aspect, a system includes a maintenance station and an autonomous coverage robot. The maintenance station includes an emitter for emitting a signal. The autonomous coverage robot is configured to maneuver over a surface and includes at least one receiver for receiving the emitted signal and a controller. The controller configured to maneuver the robot across the surface, detect a first change in a signal emitted from the maintenance station and received by the at least one receiver, detect a second change in the signal from the maintenance station and received by the at least one receiver and determine the probability that the robot will find the maintenance station in a period of time. The determined probability is based at least in part on an elapsed time between the detected first change in the signal and the detected second change in the signal.

Implementations of this aspect of the disclosure may include one or more of the following features. The emitter can include an infrared emitter and the at least one receiver comprises an infrared receiver. In some implementations, the autonomous coverage robot further includes a battery. The maintenance station can be configured to releasably engage the autonomous coverage robot to transfer power to the battery.

In yet another aspect, a method of calibrating a debris monitoring system of a waste receptacle includes detecting an initiation condition, applying a first pulse width modulation duty cycle to an emitter array, measuring a first signal at a receiver in response to the first pulse width modulation cycle, applying a second pulse width modulation duty cycle to an emitter array, measuring a second signal at the receiver in response to the second pulse width modulation duty cycle, determining whether the difference between the measured first signal and the measured signal is greater than the threshold, and setting the measured second signal as a base brightness based at least in part on the determination of whether the difference between the measured first signal and the measured second signal is greater than the threshold. The second pulse width modulation duty cycle is less than the first pulse width modulation duty cycle.

Implementations of this aspect of the disclosure may include one or more of the following features. Detecting the initiation condition can include detecting insertion of the waste receptacle into the body of a debris collection device (e.g., an autonomous cleaning robot). Additionally or alternatively, detecting the initiation condition can include detecting applied power (e.g., detecting insertion of a battery and/or the position of a power switch). In some implementations, an indicator is activated based at least in part on detecting the initiation condition.

In certain implementations, the indicator is deactivated based at least in part on whether the difference between the measured first signal and the measured second signal is greater than the threshold.

In some implementations, activating and/or deactivating the indicator includes activating and/or deactivating one or more light-emitting diodes.

In certain implementations, applying the first pulse width modulation duty cycle to the emitter array includes applying a maximum pulse width modulation duty cycle to the emitter array.

In some implementations, the waste receptacle defines an opening to receive debris into the waste receptacle. The first emitter array can be arranged to emit a signal across at least a portion of the opening. Measuring the first and second signals at the receiver can each include receiving an unreflected portion of the signal emitted by the first emitter. Additionally or alternatively, measuring the first and second signals at the receiver can each include receiving a reflected portion of the signal emitted by the first emitter.

In certain implementations, applying the second pulse width modulation duty cycle to the emitter array includes determining whether the applied second pulse width modulation is greater than a limit value.

In still another aspect, a debris monitoring system includes a receptacle, a plurality of first emitters and a plurality of second emitters, a first receiver, and a second receiver. The receptacle includes a barrier extending horizontally across a width of the receptacle and extending vertically along at least a portion of a height of the receptacle, the barrier defining at least a portion of an opening to receive debris into the receptacle. The first emitters are vertically spaced apart from one another on a first side of the opening, and the second emitters are vertically spaced apart from one another on a second side of the opening. The emitters of the first and second emitters are arranged to emit a signals span the horizontal and vertical dimensions of the opening. The first receiver is proximate to the plurality of first emitters. The second receiver is proximate to the plurality of second emitters.

In some implementations, the at least a portion of the barrier is a door movable to allow access to debris stored in the receptacle. For example, the barrier can include a hinged door. Additionally or alternatively, the barrier can include a slidable door.

In certain implementations, a vertical dimension of the opening is substantially ½ or less of the combined height of the receptacle (e.g., substantially ½ or less of the combined height of the barrier and a vertical dimension of the opening).

In some implementations, a width of the opening can be about ⅔ or less of a width of the receptacle. In these implementations, the barrier can extend substantially across the entire width of the receptacle. Thus, for example, the width of the barrier can be at least ⅓ greater than the width of the opening.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3A-3B are top views of autonomous robotic cleaners.

FIG. 3C is a rear perspective view of an autonomous robotic cleaner.

FIGS. 3D-3E are bottom views of autonomous robotic cleaners.

Like reference symbols in the various drawings indicate like elements.

DETAILED DESCRIPTION

Figure 1A:
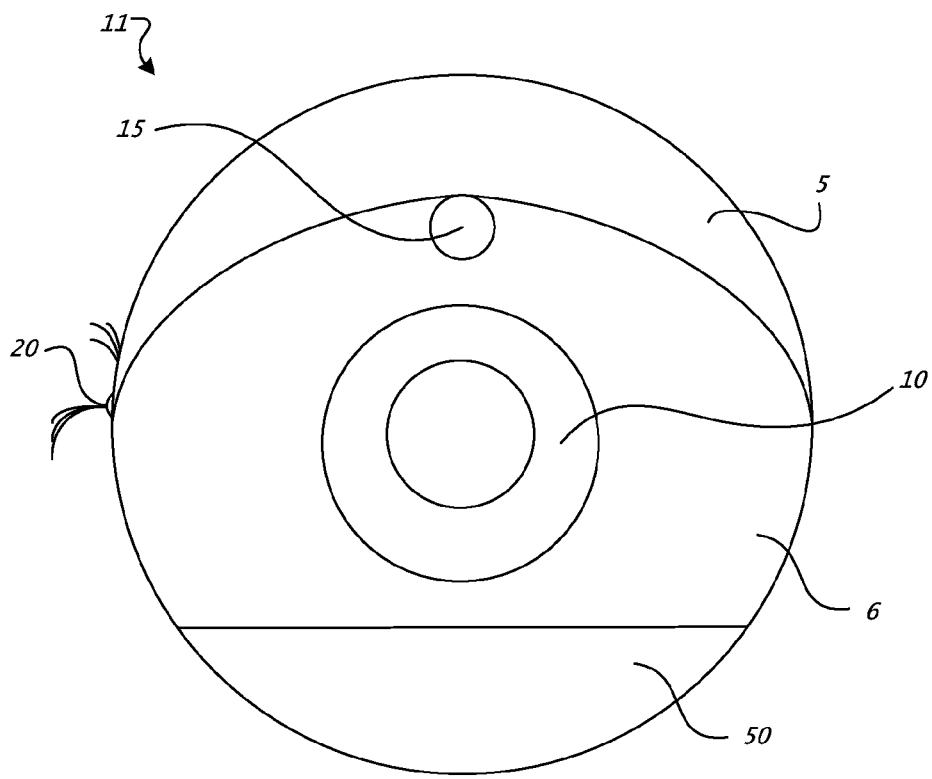
FIG. 1A is a top view of an autonomous robotic cleaner.
Figure 1B:
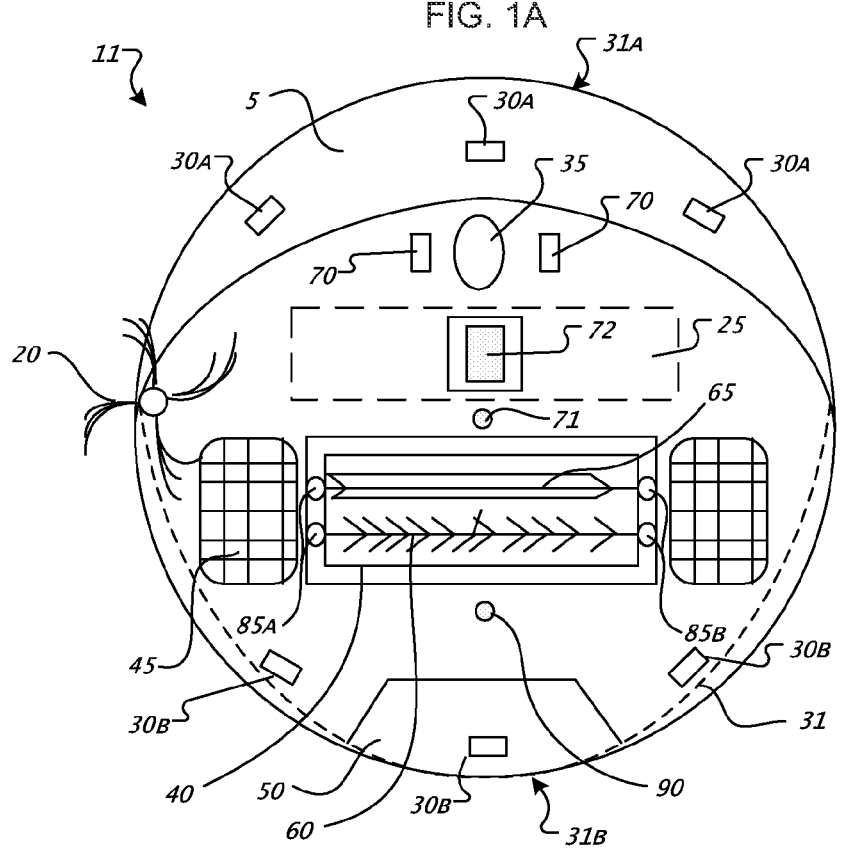
FIG. 1B is a bottom view of an autonomous robotic cleaner.
Figure 1C:
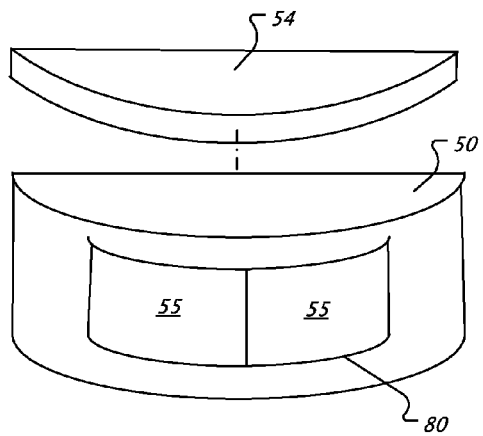
FIG. 1C is a side view of an autonomous robotic cleaner.

Referring to FIGS. 1A-1C, an autonomous robotic cleaner 11 includes a robot body 31 (e.g., a chassis and/or housing) which carries an outer shell 6 connected to a bumper 5. The robot body 31 also carries a control panel 10 and an omnidirectional receiver 15, which has a 360 degree line of vision for detection of signals emitted towards the robot 11 from substantially all directions.

Referring to FIG. 1B, installed along either side of the robot body 31 are differentially driven wheels 45, each rotatable about a transverse axis, to mobilize the robot 11 and provide two points of support. The differentially driven wheels 45 may move the robot 11 in forward and reverse drive directions such that the robot body 31 has a corresponding forward portion 31A forward of the differentially driven wheels 45 and a rear portion 31B rear of the differentially driven wheels 45.

Cliff sensors 30A (e.g., infrared sensors) are installed on the underside of the robot 11, along the forward portion 31A of the robot body 31, to detect a potential cliff forward of the robot 11 as the robot 11 moves in the forward drive direction. Cliff sensors 30B are installed on the underside of the robot 11, along the rear portion 31B of the robot body 31, to detect a potential cliff rear of the robot 11 as the robot 11 moves in the reverse drive direction. At least one of the cliff sensors 30B is disposed on a debris bin 50 in fluid communication with a cleaning head 40 to receive debris removed from a cleaning surface. The cliff sensor 30B disposed on the cleaning bin 50 can be in communication with one or more components on the robot body 31 and/or powered by a source on the robot body 31 through a communication and/or power channel, each described below, established between the cleaning bin 50 and the robot body 31. The cliff sensors 30A,B are configured to detect sudden changes in floor characteristics indicative of an edge or cliff of the floor (e.g. an edge of a stair). As described in further detail below, cliff sensors 30A and 30B can facilitate execution of a cleaning pattern including back and forth motion of the robot 11 over an area containing debris. For example, cliff sensors 30A,B disposed forward and rear of the robot 11 can reduce the likelihood that the robot 11 would move over a cliff forward or rearward of the robot 11 as the robot moves back and forth during execution of a cleaning pattern.

The forward portion 31A of the chassis 31 includes a caster wheel 35 which provides additional support for the robot 11 as a third point of contact with the floor and does not hinder robot mobility. Located proximate to and on either side of the caster wheel 35 are two wheel-floor proximity sensors 70. The wheel-floor proximity sensors 70 are configured to detect sudden changes in floor characteristics indicative of an edge or cliff of the floor (e.g. an edge of a stair). The wheel-floor proximity sensors 70 provide redundancy should the primary cliff sensors 30A fail to detect an edge or cliff. In some implementations, the wheel-floor proximity sensors 70 are not included, while the primary cliff sensors 30A remain installed along the bottom forward portion 31A of the chassis 31. In certain implementations, the caster wheel 35 is not included and additional support for the robot 11 is provided by at least a portion of the cleaning head assembly described in detail below.

A cleaning head assembly 40 is disposed generally between the forward portion 31A and the rear portion 31B of the robot 11, with at least a portion of the cleaning head assembly disposed within the robot body 31. The cleaning head assembly 40 includes a main 65 brush and a secondary brush 60. A battery 25 is carried on the robot body 31 and, in some implementations, is proximate the cleaning head assembly 40. In some examples, the main 65 and/or the secondary brush 60 are removable. In other examples, the cleaning head assembly 40 includes a fixed main brush 65 and/or secondary brush 60, where fixed refers to a brush permanently installed on the robot body 31.

A side brush 20 is supported on one side of the robot body 31 such at least a portion of the side brush 20 extends beyond the robot body 31. In some implementations, the side brush 20 is configured to rotate 360 degrees, about an axis substantially perpendicular to the cleaning surface, when the robot 11 is operational. The rotation of the side brush 20 may improve cleaning in areas adjacent the robot's side, and areas (e.g., corners) otherwise unreachable by the more centrally located cleaning head assembly 40.

A removable cleaning bin 50 is supported towards the back end 31B of the robot 11, with at least a portion of the removable cleaning bin disposed within the outer shell 6. In certain implementations, the cleaning bin 50 is removable from the chassis 31 to provide access to bin contents and an internal filter 54. Additionally or alternatively, access to the cleaning bin 50 may be provided via an evacuation port 80, as shown in FIG. 1C. In some implementations, the evacuation port 80 includes a set of sliding side panels 55 which slide along a side wall of the chassis 31 and under side panels of the outer shell 6 to open the evacuation port 80. The evacuation port 80 is configured to mate with corresponding evacuation ports on a maintenance station or other device configured to evacuate debris from the bin 50. In other implementations, the evacuation port 80 is installed along an edge of the outer shell 6, on a top most portion of the outer shell 6, on the bottom of the robot body 31, or other similar placements where the evacuation port 80 has ready access to the contents of the cleaning bin 50.

Figure 2:
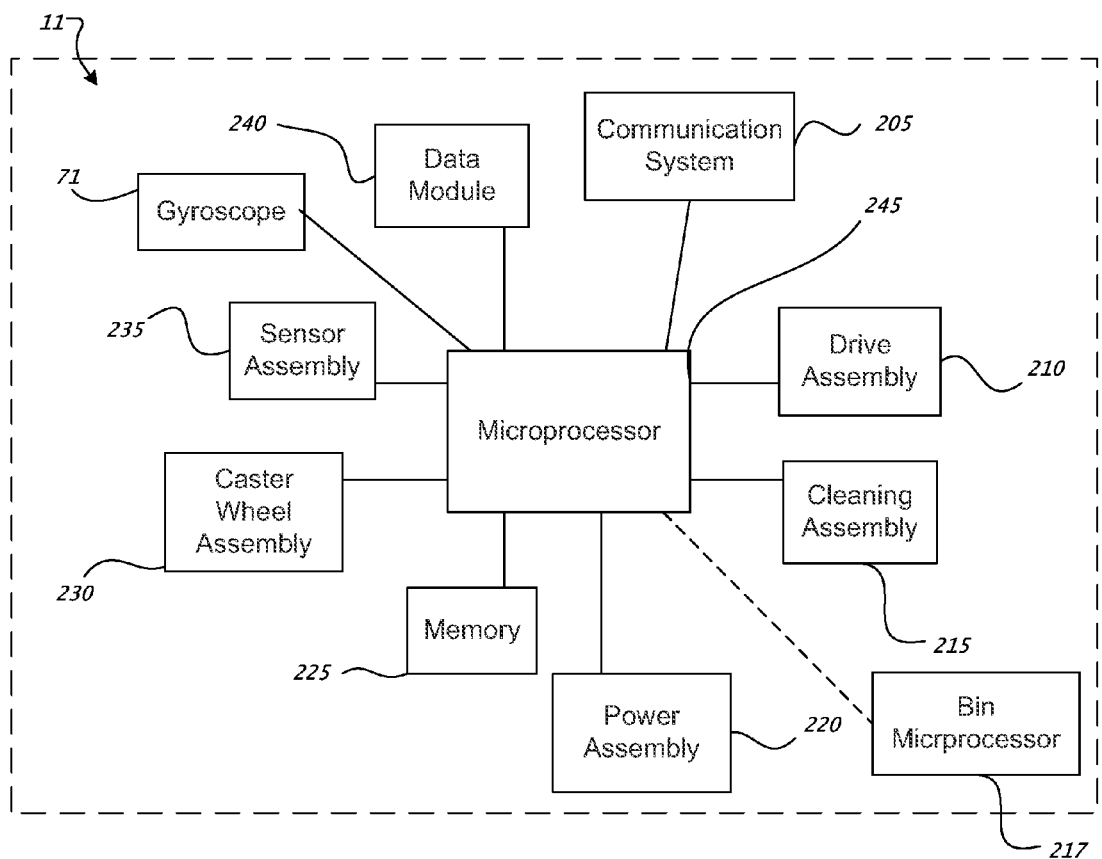
FIG. 2 is a block diagram of systems of an autonomous robotic cleaner.

FIG. 2 is a block diagram of systems included within the robot 11. The robot 11 includes a microprocessor 245 capable of executing routines and generating and sending control signals to actuators within the robot 11. Connected to the microprocessor 245 is memory 225 for storing routines and sensor input and output, a power assembly 220 (e.g., a battery and/or a plurality of amplifiers able to generate and distribute power to the microprocessor 245), and other components included within the robot 11. A data module 240 is connected to the microprocessor 245 which may include ROM, RAM, an EEPROM or Flash memory. The data module 240 may store values generated within the robot 11 or to upload new software routines or values to the robot 11.

The microprocessor 245 is connected to a plurality of assemblies and systems, one of which is the communication system 205 including an RS-232 transceiver, radio, Ethernet, and wireless communicators. The drive assembly 210 is connected to the microprocessor 245 and includes right and left differentially driven wheels 45, right and left wheel motors, and wheel encoders. The drive assembly 210 is operable to receive commands from the microprocessor 245 and generate sensor data transmitted back to the microprocessor 245 via the communication system 205. A separate caster wheel assembly 230 is connected to the microprocessor 245 and includes a caster wheel 35 and a wheel encoder. The cleaning assembly 215 is connected to the microprocessor 245 and includes a primary brush 65, a secondary brush 60, a side brush 20, and brush motors associated with each brush. Also connected to the microprocessor is the sensor assembly 235 which may include infrared proximity sensors 75, an omnidirectional detector 15, mechanical switches installed in the bumper 5, wheel-floor proximity sensors 70, stasis sensors, a gyroscope 71, and infrared cliff sensors 30.

Referring to FIGS. 3A-3E, example locations of the cleaning bin 50 and a filter 54 disposed on the chassis 31 and the outer shell 6 are shown. FIG. 3A displays a robot 300A with an evacuation port 305 disposed on the top of the robot 300A, and more specifically installed on the top of a cleaning bin 310A. The cleaning bin 310A may or may not be removable from the chassis 31 and outer shell 6, and if removable, is removable such that the bin 310A separates from (e.g., is releasably engageable with) a back portion 312A of the robot 300A.

Referring to FIG. 3B, a cleaning bin 310B is installed towards the rear portion of a robot 300B and includes a latch 315. In some implementations, a portion of the cleaning bin 310B slides toward the forward portion of the robot 310B when the latch 315 is manipulated, providing access to the contents of the cleaning bin 310B for removal. Additionally or alternatively, the cleaning bin 310B is removable from a back portion 312B of the robot 310B to provide access to the contents of the cleaning bin 310B for removal and/or to provide access to a filter (e.g., filter 54) disposed substantially within the cleaning bin 310B. In this implementation, the cleaning bin latch 315 may be manipulated manually by the operator or autonomously by a robotically driven manipulator.

Referring to FIG. 3C, a robot 300C including a cleaning bin 310C located on a rearmost side wall 320 of the outer shell 6. The cleaning bin 310C has a set of movable doors 350, each slidable along the side of the robot body 31 and each recessable under the outer shell 6. In some implementations, with the doors 350 recessed under the outer shell 6, the cleaning bin 310C is configured to accept and mate with an external evacuation port.

FIG. 3D provides a bottom view of a robot 300D and the bottom of the cleaning bin 310D located on the bottom, rear portion of the robot 300D. The cleaning bin 310D has a latch 370 allowing a door 365 located on the bottom of cleaning bin 310D to slide towards the forward portion of the robot 300D so that contents of the cleaning bin 310D may be removed. In certain implementations, the cleaning bin 310D supports a filter (e.g., filter 54 shown in FIG. 1C) and the cleaning bin 310D is removable from a back portion 312D of the robot 300D to facilitate cleaning and/or replacing the filter. The cleaning bin 310D and latch 370 may be manipulated manually by an operator or autonomously by a robotically driven manipulator.

FIG. 3E provides a bottom view of a robot 300E and the floor of the cleaning bin 310E located on the bottom, rear portion of the robot 300E. The cleaning bin 310E includes a port 380 for accessing contents of the cleaning bin 310E. An evacuation hose may be attached to the port 380 to evacuate the cleaning bin 310E. In certain implementations, the cleaning bin 310E is removable from a back portion 312E of the robot 300D to access and clean a filter disposed within the cleaning bin 310 (e.g., filter 54 shown in FIG. 1C).

Figure 3F:
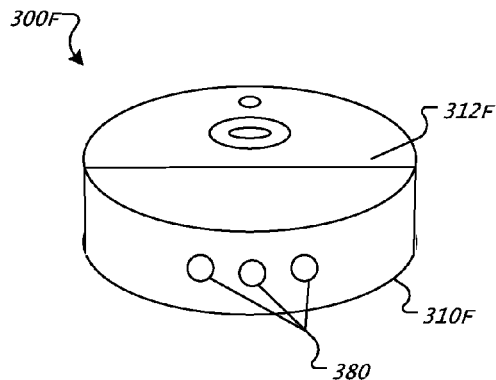
FIGS. 3F-3G are perspective views of an autonomous robotic cleaner.

Referring to FIG. 3F, a robot 300F includes a cleaning bin 310F disposed along a rear robot portion 312F. In some implementations, the cleaning bin 310F includes at least one evacuation port 380 on a rear side (three are shown). The evacuation ports 380 may be configured to receive an evacuation hose for removing debris from the bin 310F. Additionally or alternatively, the evacuation ports 380 may be configured to facilitate manual removal of debris (e.g., by holding the bin 310F to allow debris within the bin to fall out of the bin under the force of gravity).

Figure 3G:
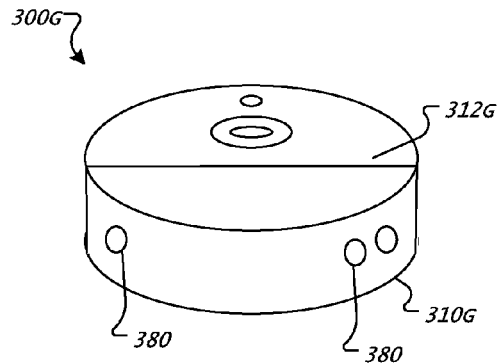

Referring to FIG. 3G, a robot 300G includes a cleaning bin 310G located on a rear robot portion 312G. The cleaning bin 310G includes one or more evacuation ports 380 on a side portion (e.g. left and/or right sides). The evacuation ports 380 are configured to receive an evacuation hose for removing debris from the bin 310G.

Figure 4A:
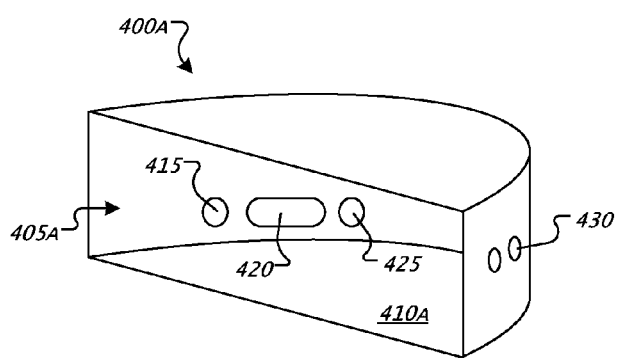
FIGS. 4A-4B are perspective views of removable cleaning bins.

The robotic cleaner 11 may receive a number of different cleaning bins 50. For example, referring to FIG. 4A, a cleaning bin 400A is configured to mate with external vacuum evacuation ports. The vacuum bin 400A defines a main chamber 405A having a sloped floor 410A that aids movement of debris towards evacuation ports 415, 420, 425. A first side evacuation port 415 is located adjacent a center evacuation port 420 which is located between the first side evacuation port 415 and a second side evacuation port 425. Located on the side walls of the bin 400A are two evacuation outlets 430 that are installed to further aid a vacuum in its evacuation operation.

Figure 4B:
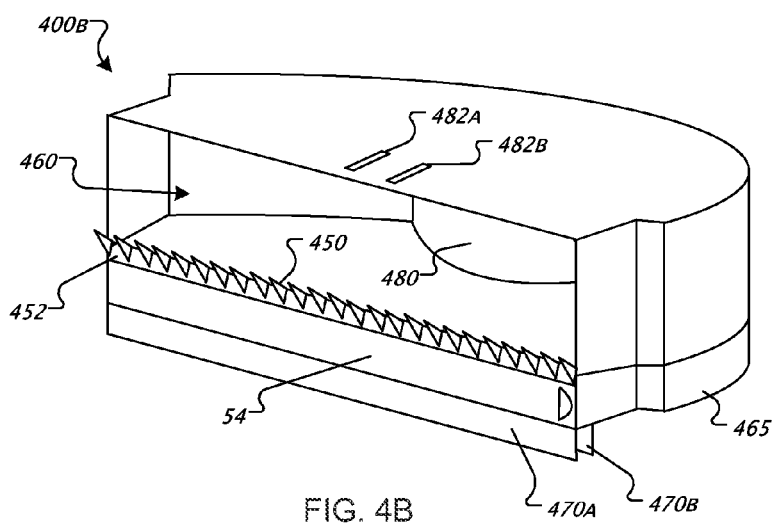
Figure 4C:
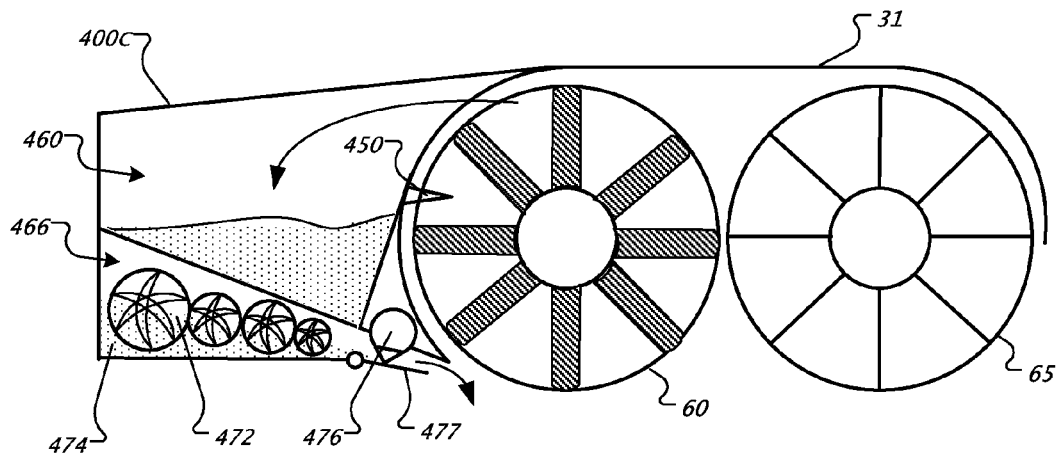
FIGS. 4C-4E are schematic views an autonomous robotic cleaner.
Figure 4D:
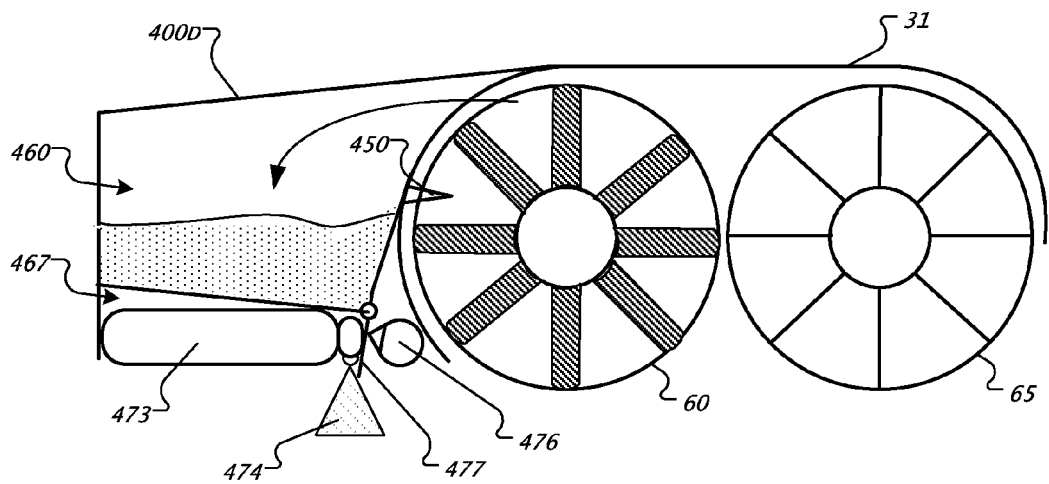
Figure 4E:
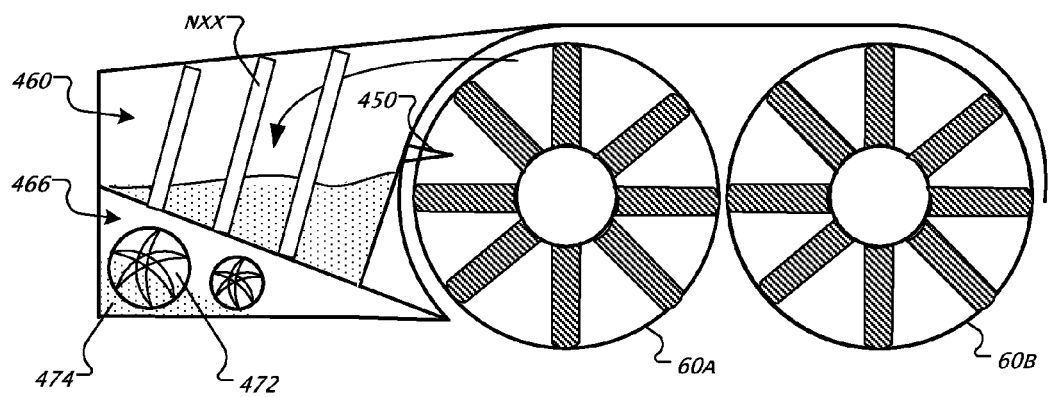

Referring to FIG. 4B, a bin 400B includes teeth 450 along a mouth edge 452 of the bin 400B. The teeth 450 reduce the amount of filament build up on the main brush 60 and/or the secondary brush 65 (see FIG. 1B) by placing the bin 400B close enough to the brush 60, 65 such that the teeth 450 slide under filament build up on the brush 60, 65 and pull off filament build up as the brush 60, 65 rotates. In some examples, the bin 400B includes between about 24-36 teeth. In the example shown, the bin 400B defines a sweeper bin portion 460 and a vacuum bin portion 465. The comb or teeth 450 are positioned between the sweeper bin portion 460 and the vacuum bin portion 465 and arranged to lightly comb the sweeper brush 60 as the sweeper brush 60 rotates. The comb or teeth 450 remove errant filaments from the sweeper brush 60 that accumulate either on the teeth 450 or in the sweeper bin portion 460. The vacuum bin portion 465 and the teeth 450 above it do not interfere with each other. The bin 400B carries a vacuum assembly 480 (e.g. a vacuum motor/fan) configured to draw debris through a channel such as the channel defined a pair of squeegees 470A and 470B in the vacuum bin portion 460.

The bin 400B includes electrical contacts 482A, 482B, which are releasably engageable with corresponding electrical contacts on the robot body 31 such that power is supplied to the bin 400B when the bin 400B is engaged with the robot body 31. In some implementations, the power is provided to the vacuum assembly 480. In certain implementations, the electrical contacts 482A, 482B can provide communication to a bin microprocessor 217. The filter 54 (shown in FIG. 1C) can separate the vacuum bin portion 460 from the vacuum assembly 480. In some examples, the filter 54 pivots open along a side, top, or bottom edge for servicing. In other examples, the filter 54 slides out of the vacuum bin portion 460.

Figure 5A:
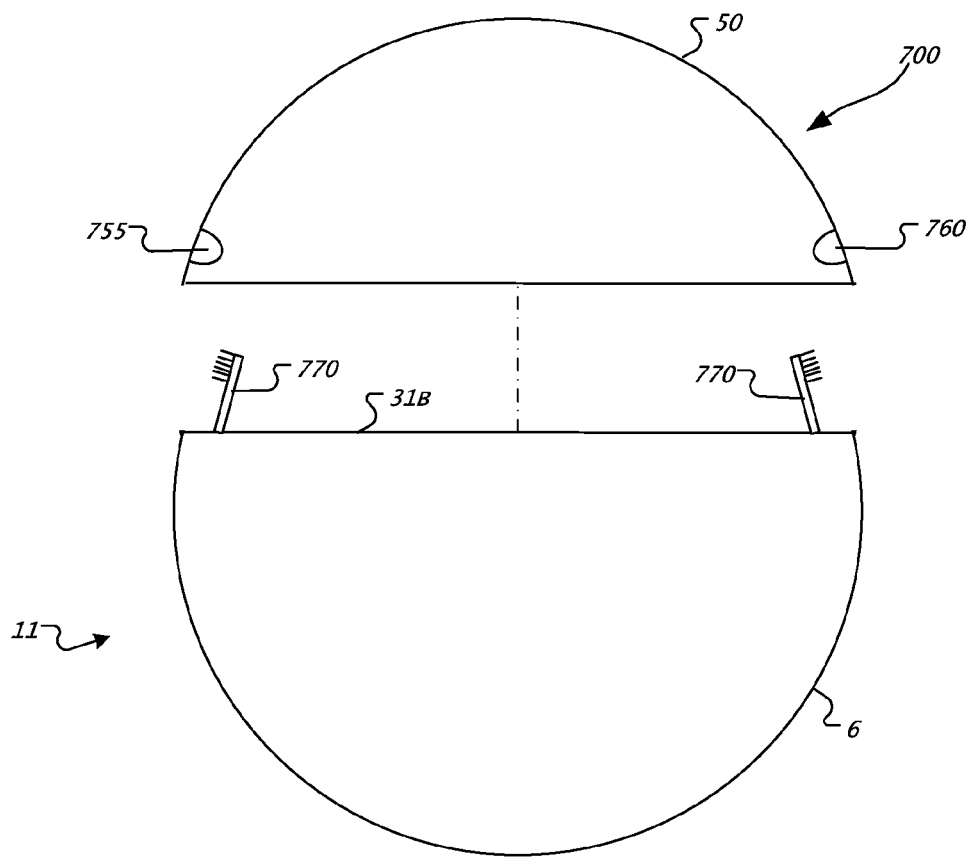
FIG. 5A is a top view of an autonomous robotic cleaner.
Figure 5B:
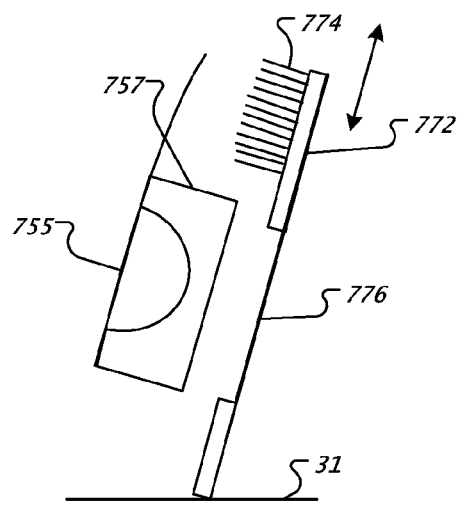
FIG. 5B is a top view of a bin sensor brush.

In some instances, the bin 50 includes a bin-full detection system for sensing an amount of debris present in the bin 50. For example, referring to FIGS. 5A-5B, the bin-full detection system includes an emitter 755 and a detector 760 housed in the bin 50. A housing 757 surrounds each of the emitter 755 and the detector 760 and is substantially free from debris when the bin 50 is also free of debris. In one implementation, the bin 50 is detachably connected to the robotic cleaner 11 and includes a brush assembly 770 for removing debris and soot from the surface of the emitter/detector housing 757. The brush assembly 770 includes a brush 772 mounted on the robot body 31 and configured to sweep against the emitter/detector housing 757 when the bin 50 is removed from or attached to the robot 11. The brush 772 includes a cleaning head 774 (e.g. bristles or sponge) at a distal end farthest from the robot 11 and a window section 776 positioned toward a base of the brush 772 and aligned with the emitter 755 or detector 760 when the bin 50 is attached to the robot 11. The emitter 755 transmits and the detector 760 receives light through the window 776. In addition to brushing debris away from the emitter 755 and detector 760, the cleaning head 774 reduces the amount of debris or dust reaching the emitter 755 and detector 760 when the bin 50 is attached to the robot 11. In some examples, the window 776 comprises a transparent or translucent material and is formed integrally with the cleaning head 774. In some examples, the emitter 755 and the detector 760 are mounted on the chassis 31 of the robot 11 and the cleaning head 774 and/or window 776 are mounted on the bin 50.

Figure 6A:
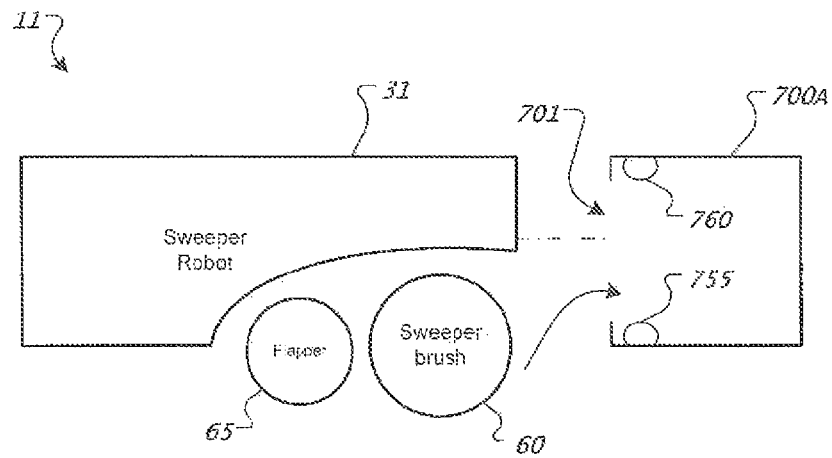
FIGS. 6A-6C are schematic views of autonomous robotic cleaners.

Referring to FIG. 6A, in some implementations a sweeper robot 11 includes a brush 60 and a flap 65 that sweep or otherwise agitate debris from the cleaning surface for movement into a bin 700A having an emitter 755 and a detector 760, each positioned near a bin mouth 701 (e.g., an opening defined by the bin 700A).

Figure 6B:
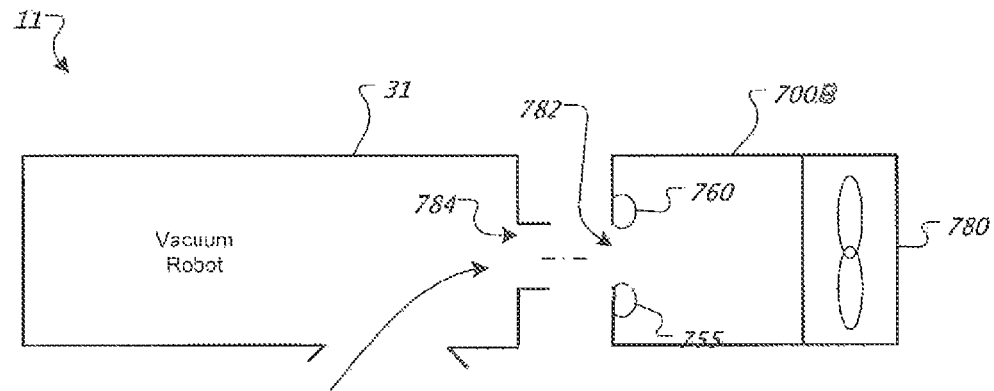

Referring to FIG. 6B, in certain implementations a bin 700B includes a vacuum/blower motor 780, and an emitter 755 and a detector 760 located near an inlet 782 of a vacuum flow path into the bin 700B. The robot body 31 of the robot 11 includes a robot vacuum outlet 784 that engages (e.g., fits flush with) the vacuum inlet 782 of the bin 700B. By placing the emitter 755 and the detector 760 near the debris inlet 782, debris can be detected along the intake flow path rather than within the debris chamber 785. Therefore, a bin-full condition may be triggered when either the amount of debris swept or vacuumed along the flow path is extremely high (which may typically be a rare scenario), or when the debris chamber 785 is full (e.g. debris is no longer deposited therein, but instead backs up along the intake flow path near the inlet 782).

Figure 6C:
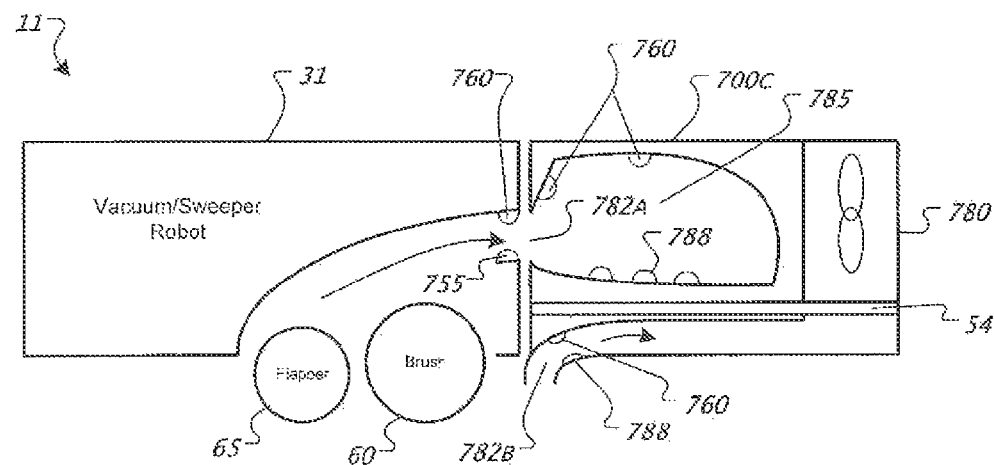

Referring to FIG. 6C, in some implementations, a combined vacuum/sweeper bin 700C includes an emitter 755 and a detector 760 pair positioned near a sweeper bin inlet 782A and a vacuum bin inlet 782B. The emitter 755 and detector 760 mounted near the sweeper bin inlet 782A are supported on the robot body 31 of the robot 11. Additionally or alternatively, the inlet sensors 755, 760, several emitter arrays 788 are positioned on an interior surface of the bin 700C (e.g., a bottom interior surface of the bin 700C) and one more detectors 760 are positioned on a substantially opposite interior surface of the bin 700C (e.g., a top interior surface of the bin 700C). As described in further detail below, signals from the detectors 760 located along the intake flow path, as well as the container of the bin 700C, may be compared for detecting the presence of debris and/or for determining bin fullness. For example, when a heavy volume of debris is pulled into the bin 700C by the brush 60, flapper 65, and/or vacuum motor 780, the detectors 760 located along the flow path may generate a low detection signal. However, detectors 760 located on the top interior surface of the bin 700D will not detect a full bin 700C, if it is not yet full. Comparison of the detector signals avoids a false bin-full condition.

Figure 7A:
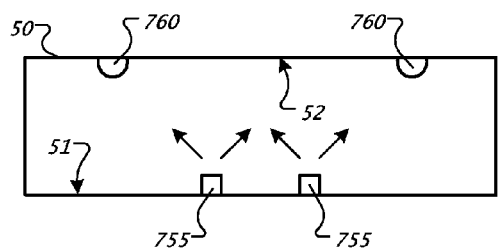
FIGS. 7A-7B are front views of removable cleaning bins.

FIGS. 7A-7E illustrate a transmissive optical debris-sensing system for detecting debris within the bin 50. As shown in FIG. 7A, in some examples, the bin 50 includes emitters 755 located on a bottom interior surface 51 of the bin 50 and detectors 760 located on an upper interior surface 52 of the bin 50. The emitters 755 emit light that traverses the interior of the bin 50 and which may be detected by the detectors 760. When the interior of the bin 50 is clear of debris, the transmitted light from the emitters 755 produces a relatively high signal strength in the detectors 760, because very little of the transmitted light is diverted or deflected away from the detectors 760 as the transmitted light passes through the empty interior of the bin 50. By contrast, when the interior of the bin 50 contains debris, at least some of the light transmitted from the emitters 755 is absorbed, reflected, or diverted as the light strikes the debris, such that a lower proportion of the emitted light reaches the detectors 760. The degree of diversion or deflection caused by the debris in the interior of the bin 50 correlates positively with the amount of debris within the bin 50.

By comparing the signals generated by the detectors 760 when the bin 50 does not contain debris to subsequent signal readings obtained by the detectors 760 as the robot 11 sweeps and vacuums debris into the bin 50 during a cleaning cycle, the presence of debris within the bin 50 may be determined. For example, when the subsequently polled detector signals are compared to initial detector signals (e.g., signals taken when the bin 50 is substantially empty), a determination can be made whether the debris accumulated within the bin 50 has reached a level sufficient to trigger a bin-full condition.

One example bin configuration includes one emitter 755 and two detectors 760. Another configuration includes positioning one or more emitters 755 and detectors 760 in the bin 51 and cross-directed in mutually orthogonal directions. The robot 11 may determine that heavy debris has accumulated on the bottom of the bin 50 but has not filled the bin 50, when signals generated by a first detector 760 on the inner top surface 52 is relatively low and signals generated by a second detector 760 on an inner side wall (which detects horizontally-transmitted light) does not meet a bin-full threshold. Additionally or alternatively, when both detectors 760 report a relatively low received-light signal, it may be determined that the bin 50 is full.

Figure 7B:
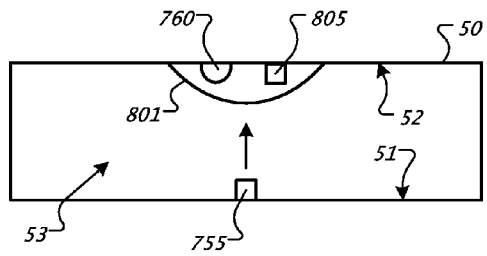

Referring to FIG. 7B, in some implementations, the bin 50 includes a detector 760 proximate a calibration emitter 805, both disposed behind a shield 801 on the top interior surface 52 of the bin 50. An emitter 755 is disposed on the bottom interior surface 51 of the bin 50. A calibration signal reading is obtained by emitting light from the calibration emitter 805 which is then detected by the detector 760 as a first reading. The translucent or transparent shield 801 prevents emission interference between the transmission of light from the calibration emitter 805 to the detector 760 with dust or debris from the bin 50. The emitter 755 then transmits light across the interior of the bin 50 and the detector 760 takes a second reading of received light. By comparing the second reading to the first reading, a determination may be made whether the bin 50 is full of debris. In some examples, the robot 11 includes sensors 755, 760 positioned along a debris flow path prior to a mouth 53 of the bin 50. The bin full sensors 755, 760 may detect debris tending to escape from the bin 50.

Figure 7C:
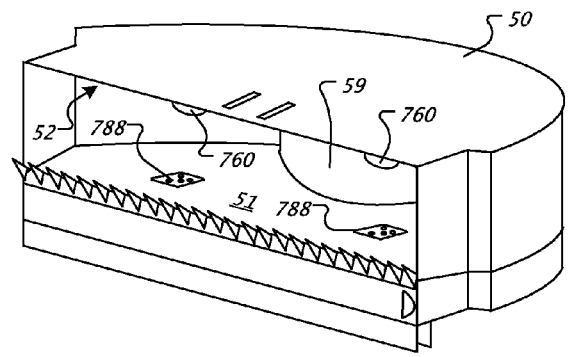
FIGS. 7C-7E are perspective views of removable cleaning bins.

Referring to FIG. 7C, in some implementations, the bin 50 includes two emitter arrays 788 and two detectors 760. Each emitter array 788 may include several light sources. The light sources may each emit light frequencies that differ from one another within the same emitter arrays 788. For example, varying frequencies of light emitted by the light sources exhibit various levels of absorption by debris of different sizes. A first sub-emitter within the emitter array 788 may emit light at a first frequency, which is absorbed by debris of very small particle size, while a second sub-emitter within the emitter arrays 788 may emit light at a second frequency which is not absorbed by small-sized debris particles. The robot 11 may determine whether the bin 50 is full even when the particle size of the debris varies by measuring and comparing the received light signals from the first and second sub-emitters. Undesirable interference with the optical transmissive detection system may be avoided by employing sub-emitters emitting light at different frequencies.

Multiple emitter arrays 788 and detectors 760 may provide more accurate and reliable bin fullness detection as compared to, for example, a single emitter and detector pair. In the example shown, the multiple emitter arrays 788 provide cross-bin signals to detect potential bin blockages. One possible blockage location is near an intruding vacuum holding bulkhead 59, which partially divides the bin 50 into two lateral compartments. Additionally or alternatively, a blockage may occur when received debris of a large enough size (e.g. paper or hairball) blocks and compartmentalizes the bin 50 at least temporarily. In certain implementations, a blockage occurs when shifting, clumping, moving, vibrated, or pushed debris within the bin creates one or more compartments in the bin 50 (e.g., via systematic patterns of accumulation). If debris accumulates in one lateral compartment, but not another, a single detector pair may not detect such accumulation. A single detector pair may also provide a false-positive signal from a large debris item or clump (e.g., indicating that the bin 50 is full when it is not). Multiple emitter arrays 788 located on the bottom interior surface 51 of the bin 50 and multiple detectors 760 located on the top interior surface 52 of the bin 50 in two different lateral or front-to-back locations covers more potential volume of the bin 50 for more accurate and reliable bin fullness detection as compared to a single detector pair in the same or similar orientation. A histogram or averaging of the bin detector signals or using XOR or AND on the results of more than one break-beam may be used to get more true positives (even depending on the time since accumulation began).

Figure 7D:
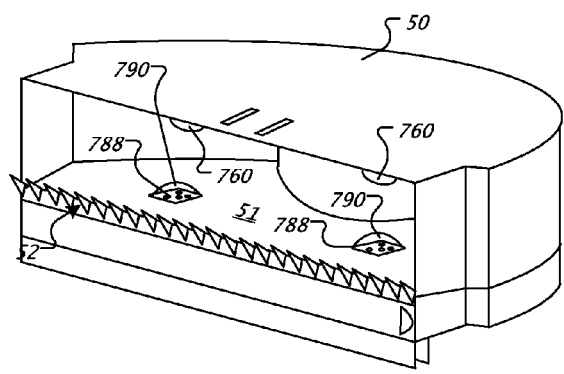

Referring to FIG. 7D, in certain implementations, the bin 50 includes a transmissive optical detection system including two emitter arrays 788, each having a diffuser 790 diffusing emitted infrared light. The diffuse light transmitted to the interior of the bin 50 provides a steadier detection signal generated by the detectors 760 relative to a detection signal generated from a concentrated beam of light from a non-diffuse light source at least because the diffuse light provides a type of physical averaging of the emitted signal. The detectors 760 receiving diffused infrared light signals can measure an overall blockage amount versus interruption of only a line-of-sight break beam from one emitter.

Figure 7E:
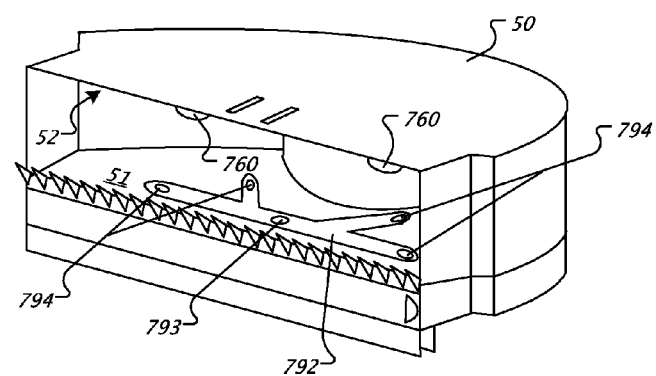

Referring to FIG. 7E, in certain implementations, the bin 50 includes a light pipe or fiber-optic pathway 792 disposed on the bottom interior surface 51 of the bin 50. Light from a light source 793 in the bin 50 travels along the fiber-optic pathway 792 and is emitted from distributor terminals 794. This bin configuration centralizes light production to the single light source 793, rather than supplying power to several independent light sources, while distributing light across the bin 50. The distributor terminals 794 may also include a diffuser 790, as discussed above with respect to FIG. 7D.

Figure 7F:
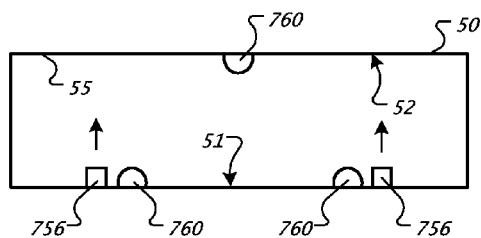
FIGS. 7F-7H are front views of removable cleaning bins.
Figure 7G:
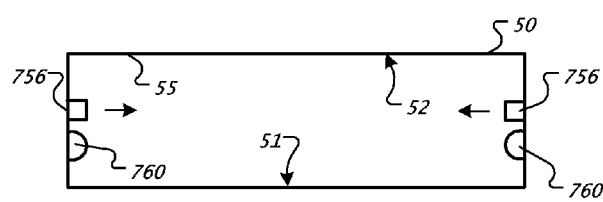
Figure 7H:
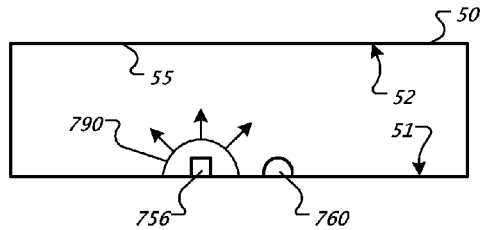

Referring to FIGS. 7F-7H, in some implementations, the bin 50 includes optical debris detection by reflective light transmission. In one example, as shown in FIG. 7F, the bin 50 includes a shielded emitter 756 located near a detector 760. Light emitted by the shielded emitter 756 does not travel directly to the detector 760 because of the shielding. However, light emitted from the emitter 756 is reflected by the interior surface 55 of the bin 50, and traverses an indirect path to the detectors 760. The attenuation of the reflected light caused by debris within the bin 50 may be comparatively greater than in a direct transmissive configuration, because the path the reflected light must travel within the bin 50 is effectively doubled, for example. Although the shielded emitter 756 and detector 760 are illustrated as being proximate to each other, they may be additionally or alternatively spaced apart from each other. The emitter 756 and detector 760 may be positioned on the same surface, or on different surfaces.

Referring to FIG. 7G, in certain implementations, two sets of shielded emitters 756 and detectors 760, each located on opposite horizontal sides of the interior of the bin 50. In this configuration, light received by each detector 760 may be a combination of light directly transmitted from the shielded emitter 756 located on the opposite side of the bin 50, as well as light reflected off the interior surface 55 by the proximal shielded emitter 756. In some examples, a first set of shielded emitters 756 and detectors 760 is located on a bin surface adjacent to a second set of shielded emitters 756 and detectors 760. In one example, a single shielded emitter 756 and detector 760 pair is located on a bottom surface 51 of the bin 50.

FIG. 7H illustrates a configuration in which the bin 50 includes a diffusive screen 790 placed along the transmission path of the shielded emitter 756 disposed on a bottom Surface 51 of the bin 50. The diffusive screen 790 diffuses light emitted from the shielded emitter 756 that reflects off various surfaces of the interior 55 of the bin 50 before reaching the detector 760, thereby providing a detection signal that reflects a broad area of the interior of the bin 50.

Referring to FIGS. 8A-8E, in some implementations, the bin 50 includes an optical detection system 800 that detects debris moving through a combination of reflective and transmissive signals in the bin 50. The optical detection system 800 includes a first receiver 802A, a second receiver 802B, a first emitter array 804A, and a second emitter array 804B. During use, debris 48 enters the bin 50 through the mouth 53 and forms an accumulation 49 extending from the bottom surface 51 of the bin. As debris 48 continues to enter the bin 50, the accumulation 49 can increase in size in a direction defined from the bottom surface 51 to the top interior surface 52 (compare FIGS. 8A, 8B, and 8C). As described in further detail below, the emitter arrays 804A,B are sequentially enabled and disabled (e.g., pulsed at a substantially constant frequency) while the receivers 802A,B are synchronously sampled to measure reflected and transmissive signals and further processed to detect the debris 48 moving past the optical detection system 800 and to determine whether the bin 50 is full of debris (e.g., whether accumulation 49 of the debris 48 has size and/or density characteristics indicative of a "bin full" condition).

Figure 8A:
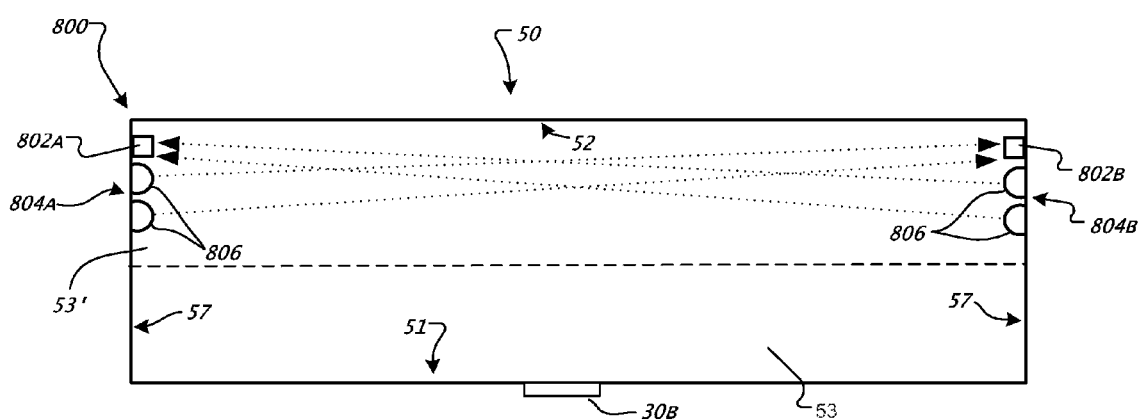
FIGS. 8A-8E are front views of removable cleaning bins.
Figure 8B:
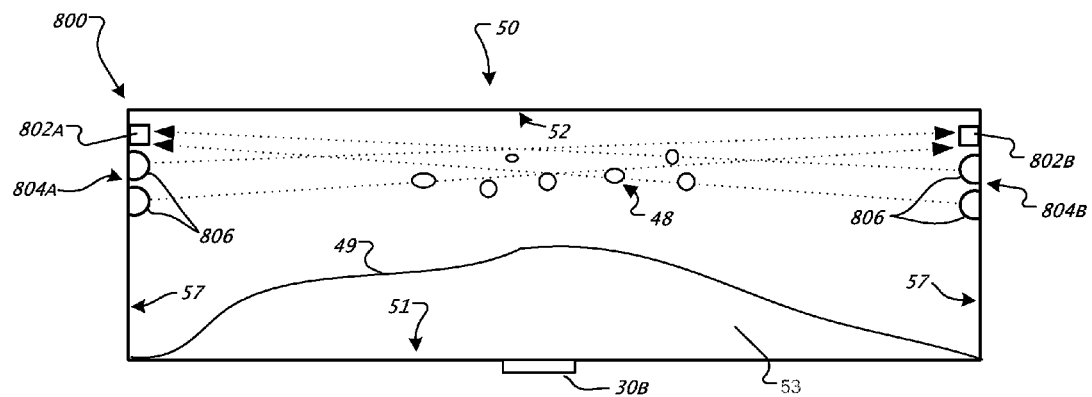
Figure 8C:
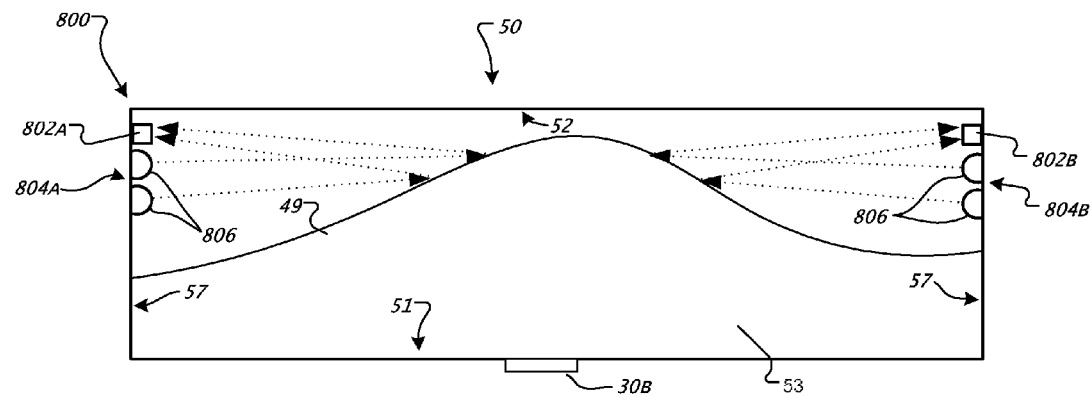
Figure 8D:
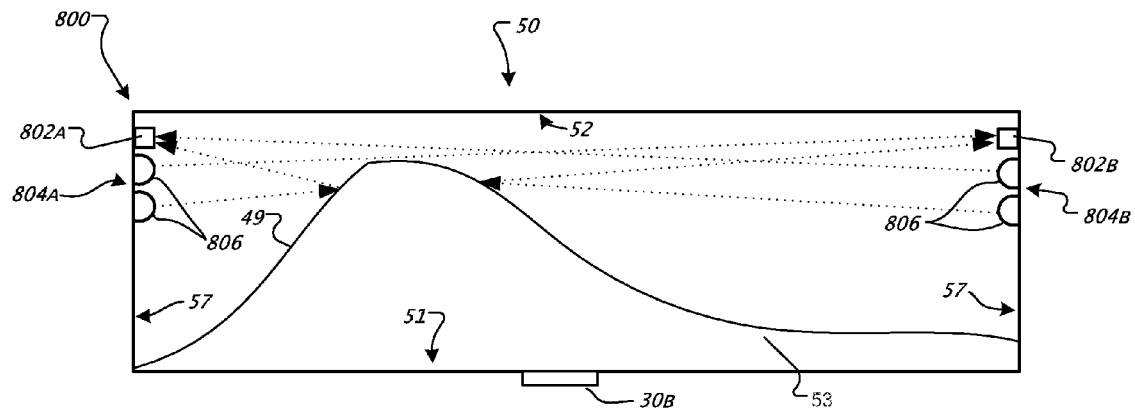
Figure 8E:
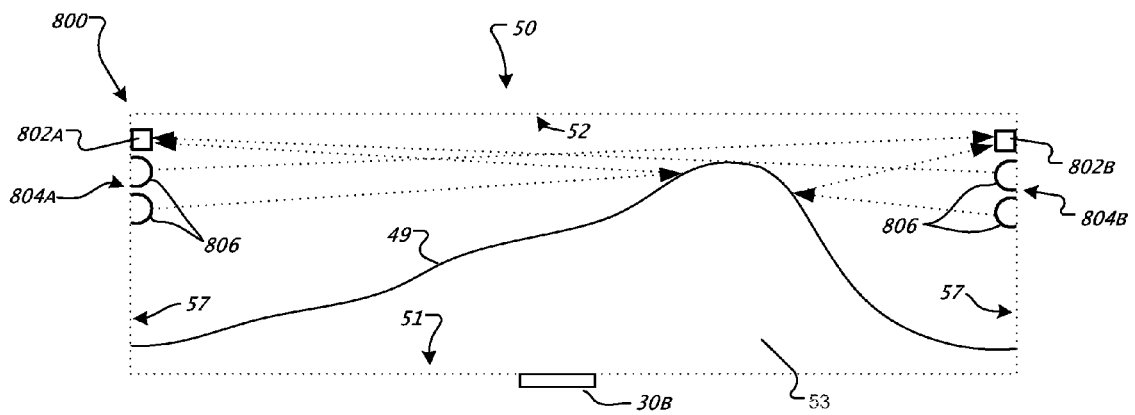

When the bin 50 is empty (as shown in FIG. 8A) or contain an accumulation 49 of debris below the receivers 802A,B and emitters 804A,B (as shown in FIG. 8B), the transmissive signal received at each receiver 802A,B is greater than (e.g., substantially greater than) the reflected signal received at the respective receiver. As the bin 50 fills with debris 48 (e.g., during operation), the magnitude of the reflected signal can increase relative to the magnitude of the transmissive signal measured by each respective receiver 802A,B. When the accumulation 49 of debris has filled the bin 50 (as shown, for example, in FIG. 8C), the reflective signal is about equal to or greater than the transmissive signal measured at the respective receiver 802A,B. As discussed in further detail below, a comparison of the reflected signal measured at the receiver 802A with the reflected signal measured at the receiver 802B can provide an indication of whether the accumulation 49 of debris in the bin 50 is symmetrical (FIG. 8C) or axisymmetrical (FIGS. 8D and 8E).

The first and second receivers 802A,B are disposed on substantially opposite sides of the mouth 53 of the bin and separated from one another along the largest dimension of the mouth 53. The first and second receivers 802A,B are generally directed toward one another such that each receiver may measure light originating from a source proximate to the other receiver, as described in further detail below. In some implementations, the first and second receivers 802A,B are supported on substantially opposing side walls 57 of the bin 50. The mouth 53 can be an opening in a substantially vertical plane perpendicular to the cleaning surface when the bin 50 is mounted on the robot body 31. For example, the mouth 53 can be a substantially rectangular opening, with the side walls 57 define the short sides of the substantially rectangular opening and the bottom surface 51 and the top portion 52 define the long sides of the substantially rectangular opening.

In some implementations, the first and second receivers 802A,B supported on substantially opposing side walls 57 of the bin 50 can reduce the likelihood of false positive signals by providing redundant measurements that may be compared to one another to determine a bin-full condition or an anomaly in debris accumulation in the bin. For example, if the reflected signals received by the first and second receivers 802A,B are substantially similar, this can be an indication that the bin is full. Additionally or alternatively, if the reflected signal received by the first receiver 802A is larger (e.g., substantially larger) than the reflected signal received by the second receiver 802B, this can be an indication of axisymmetric debris accumulation in the portion of the bin closest to the first receiver 802A (as shown, for example, in FIG. 8D). Similarly, if the reflected signal received by the second receiver 802B is larger (e.g., substantially larger) than the reflected signal received by the first receiver 802A, this can be an indication of axisymmetric debris accumulation in the portion of the bin closest to the second receiver 802B (as shown, for example, in FIG. 8E). In certain implementations, the redundant measurements afforded by the first and second receivers 802A,B can detect an anomaly such as a piece of paper or other obstruction in the area of a respective one of the first and second receivers 802A,B.

The first and second receivers 802A,B and the first and second emitter arrays 804A,B are disposed toward the top interior surface 52 of the bin 50 to bias the sensing area toward the top of the bin 50, where most of the debris enters the bin 50 in certain implementations. Additionally or alternatively, positioning the first and second receivers 802A,B and the first and second emitter arrays 804A,B toward the top interior surface 52 of the bin 50 facilitates bin-full detection (e.g., reduces the likelihood of false positive signals) in implementations in which the bin 50 fills from the bottom surface 51 to the top surface 52. In certain implementations, positioning the receivers 802A,B and emitter arrays 804A,B toward the top interior surface 52 can reduce deterioration of the receivers 802A,B and emitter arrays 804A,B resulting from the accumulation of debris on the receivers 802A,B at least because the top portion of the bin 50 is typically the position of least debris accumulation.

The first and second emitter arrays 804A,B are disposed proximate to and below the respective first and second receivers 802A,B such that each emitter array 804A,B emits a signal substantially diagonally across at least a portion of the mouth 53. Each emitter array 804A,B is oriented to emit a signal across the mouth 53 of the bin 50, toward a respective opposing receiver 802A,B. For example, the first emitter array 804A emits a signal toward the second receiver 802B such that the second receiver 802B receives a transmissive (e.g., unreflected) portion of a signal from the first emitter array 804A and the first receiver 802A receives a reflected portion of a signal from the first emitter array 804A when there is no debris in the bin 50. The second emitter array 804B and the first receiver 802A are arranged relative to one another in an analogous manner.

Each emitter array 804A,B is substantially unshielded and may include one or more light sources 806 (e.g., two light sources). In implementations in which the emitter arrays 804A,B include more than one light source 806, light sources 806 of each array are arranged one above the other and spaced apart from one another. In these implementations, such spacing of multiple light sources 806 can facilitate emission of signals that cover all or a substantial portion of the mouth 53 without requiring custom lensing of the light sources 806. The light sources 806 may be arranged to emit signals substantially covering the mouth 53 (e.g., covering more than about 50% of the area of the mouth 53) when all of the light sources 806 emit a signal. In certain implementations, the first receiver 802A and the first emitter array 804A is substantially identically arranged as the second receiver 802A and the second emitter array 804B such that, for example, the signals emitted by the first emitter array 804A intersect (e.g., crisscross) the signals emitted by the second emitter array 804 along an axis substantially bisecting the mouth 53.

In some implementations, the receivers 802A,B and the emitter arrays 804A,B are supported on the robot body 31, just upstream of the mouth 53 of the bin 50 such that the receivers 802A,B and the emitter arrays 804A,B remain disposed on the robot body 31 when the bin 50 is disengaged from the robot body 11. In some implementations, at least some of the receivers 802A,B and the emitter arrays 804A,B are mechanically coupled to the bin 50 and, thus, move with the bin 50 when the bin 50 is disengaged from the robot body 11. The receivers 802A,B and the emitter arrays 804A,B may be in wireless communication with the microprocessor 245 and/or the bin microprocessor 217 (see FIG. 2). The wireless communication between the microprocessor 245 and/or bin microprocessor 217 and the optical detection system 800 can include one or more of the following: infrared communication, electromagnetic communication, and radiofrequency communication.

Figure 9A:
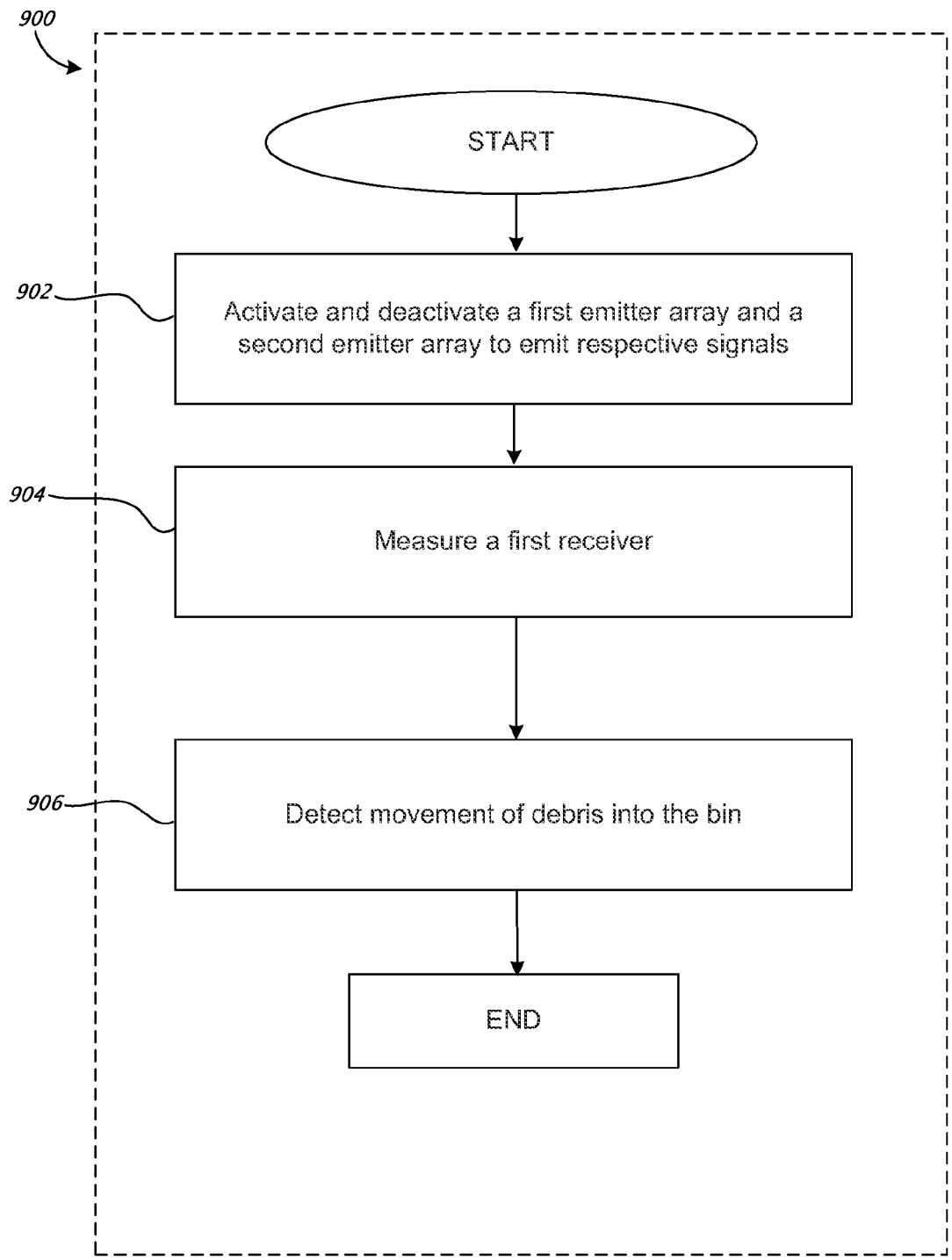
FIG. 9A is process flow chart of a debris monitoring routine.

Referring to FIG. 9A, the optical detection system 800 includes a debris monitoring routine 900 to monitor passage of debris into the bin. The debris monitoring routine 900 may be implemented through communication between the optical detection system 800 and one or more of the bin microprocessor 217 and the microprocessor 245.

The first emitter array 804A and the second emitter array 804B are activated and deactivated 902 to emit respective signals across the mouth 53 of the bin 51. The activation and deactivation 902 is done sequentially such that the first emitter array 804A and the second emitter array 804B are each deactivated during a first time step, the first emitter array 804A is activated and the second emitter array 804B is deactivated during a second time step, and the first emitter array 804A is deactivated and the second emitter array 804B is activated during a third time step. In some implementations, the activation and deactivation 902 of the first and second emitter arrays 804A,B is cycled at a substantially constant frequency of about 0.5 kHz to about 20 kHz (e.g., about 1 kHz).

The first receiver 802A is measured 904. The measurement can be taken at a substantially constant rate of about 0.25 kHz to about 10 kHz (e.g., about 4 kHz). In some implementations, the second receiver 802B is measured in an analogous manner. The measured signals from the first receiver 802A and the second receiver 802B can reduce the likelihood of false positive measurements by, for example, comparing the measured signals from the first receiver 802A and the second receiver 802B. Additionally or alternatively, the measured signals from the first receiver 802A and the second receiver 802B can be used to determine whether the debris is entering the bin 50 from the right side or from the left side.

The movement of debris through the mouth 53 is detected 906 based at least in part on a first measurement obtained when the first and second emitter arrays 804A,B are each deactivated, a second measurement obtained when the first emitter array 804A is activated and the second emitter array 804B is deactivated, and a third measurement obtained when the first emitter array 804A is deactivated and the second emitter array 804B is activated. For example, detecting 906 the movement of debris through the mouth 53 can include comparing an instantaneous value of a measurement to its respective average value. The impact of ambient light can be filtered out by adjusting the magnitudes of second and third measurements based at least in part on the first measurement, taken with both emitter arrays 804A,B deactivated. Additionally or alternatively, as described in further detail below, a base brightness can be determined through a dynamic calibration routine initiated, for example, based at least in part upon detection of an initiation condition.

In some implementations, the first, second, and third measurements are processed as a function of time and changes in at least one of the processed measurements (e.g., at least one of the processed second and third measurements) are detected. For example, processing as a function of time may include a low pass filter to baseline the measured value to an average value. Such low pass filtering can reduce sensor-to-sensor variation and, thus, for example, improve the robustness of the debris detection using the optical debris detection system 800.

The detected 906 debris through the mouth 53 of the bin 51 can include generating a signal to initiate a spot coverage routine to move the robot 11 over an area corresponding to the detected debris, as described in detail below. In certain implementations, the initiation of such a spot coverage routine is based at least in part on a quantified amount of debris. For example, the spot coverage routine can be initiated and/or adjusted if a large amount of debris is detected in a given area.

For the sake of clarity of description, the debris monitoring routine 900 has been described as monitoring passage of debris into a debris bin based on measuring signals at the first receiver 802A. However, it should be noted that the debris monitoring routine 900 can additionally or alternatively include analogous measurements of signals at the second receiver 802B.

Figure 9B:
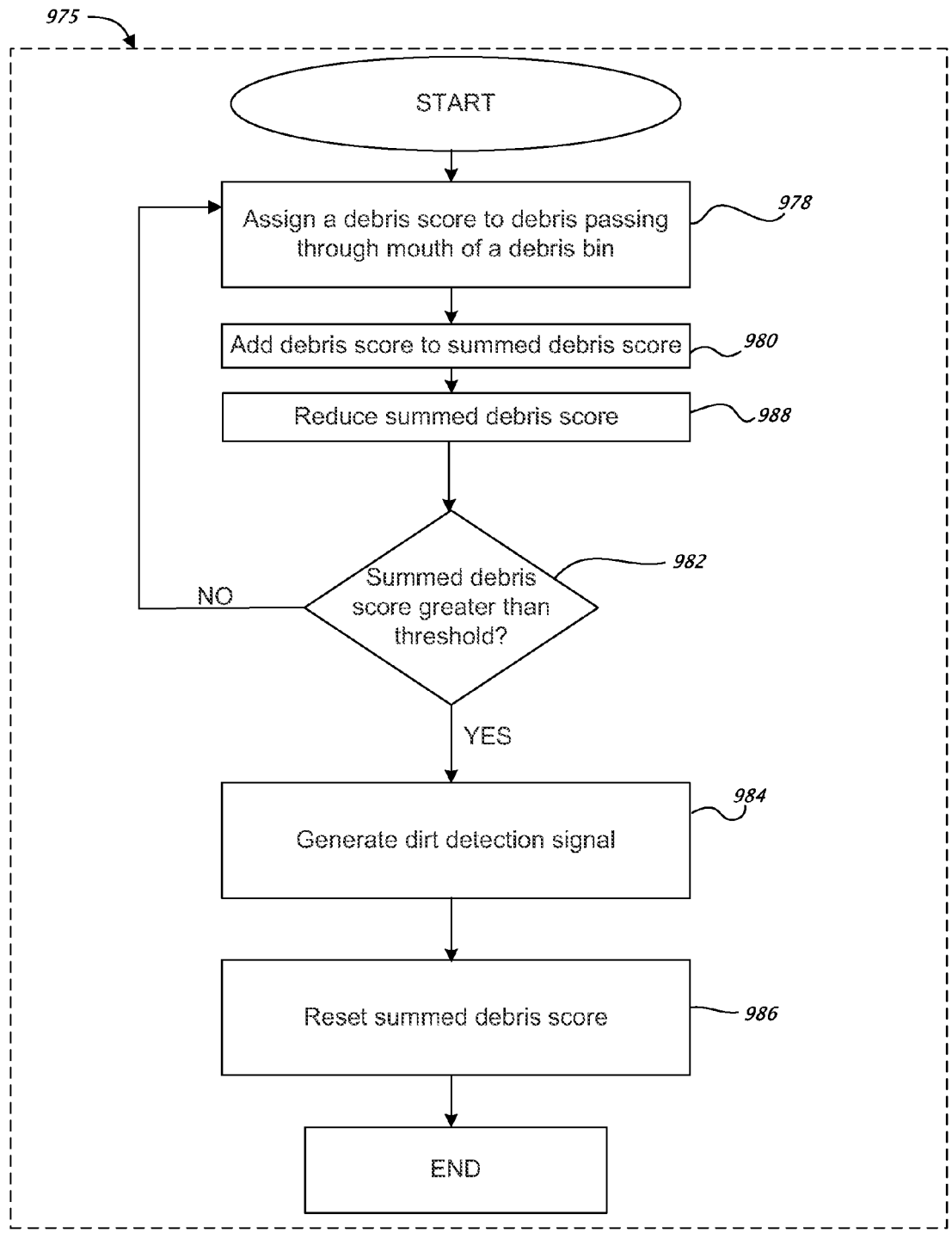
FIG. 9B is a process flow chart of a debris quantifying routine.

In some implementations, referring to FIG. 9B, the optical detection system 800 includes a debris quantifying routine 975. The debris quantifying routine 975 may be implemented through communication between the optical detection system 800 and one or more of the bin microprocessor 217 and the microprocessor 245.

The debris quantifying routine 975 includes periodically assigning 978 a score to the debris passing through the mouth 53. The score can be based, at least in part, on the amount of light determined to be blocked by the debris, which can be substantially quantified based on one or more of the following: the magnitude of the measured debris signal (indicative of the size of the debris) and the duration of the measured debris signal (indicative of the concentration of debris). The assigned debris score is added 980 to previous debris scores. The adding 980 of the present debris score to the previous debris scores can include regularly decrementing 988 the running sum of the debris scores by a fixed amount. Such regular decrementation is sometimes referred to as "leaky" integration and can reduce the likelihood that small and light debris (e.g., loose carpet fibers or other "ambient" debris that is part of the surface being cleaned) will be detected as debris while still allowing large pieces of debris and high concentrations of small debris to be detected. The amount of decrementation can be a fixed value. Additionally or alternatively, the amount of decrementation can be adjusted (e.g., manually adjusted) based on the surface being cleaned such that surfaces that shed (e.g., carpet) will have a generally higher decrement than surfaces that do not shed (e.g., hardwood floors).

If the summed debris score is greater than a threshold 982, a dirt detection signal is generated 984 and the summed debris score is reset 986 (e.g., reset to zero). If the summed debris score is not greater than the threshold 982, periodic debris scores will continue to be assigned 978 and added 980 to previous debris scores. The threshold for determining the generation of the debris signal can be a fixed value stored in the bin microprocessor 217. In certain implementations, the threshold can be lower at the beginning of the cleaning cycle (e.g., when the detected debris signal is more likely to be indicative of debris on the floor) than at the end of the cleaning cycle. Additionally or alternatively, the threshold can increase the more often debris is detected. This can reduce the likelihood that the robot 11 will run a spot coverage pattern too many times.

Figure 9C:
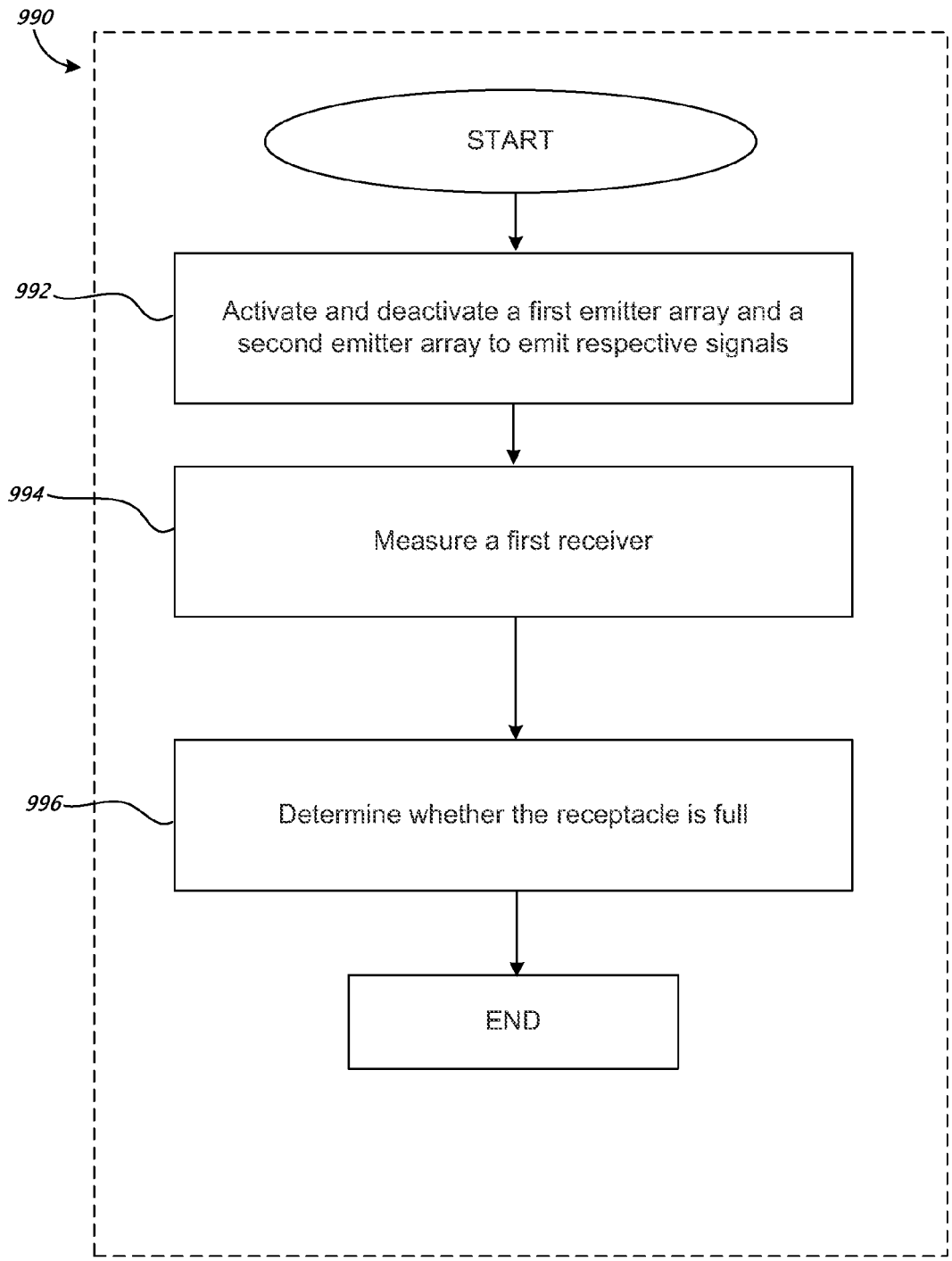
FIG. 9C is a process flow chart of a bin-full detection routine.

Referring to FIG. 9C, in some implementations, the optical detection system 800 includes a bin-full detection routine 990 to determine whether the bin 50 is full of debris. The bin-full detection routine 990 may be implemented through communication between the optical detection system 800 and one or more of the bin microprocessor 217 and the microprocessor 245.

The first emitter array 804A and the second emitter array 804B are activated and deactivated 992 to emit respective signals across the mouth 53 of the bin 51, and the first receiver 802A is measured 994. The activation and deactivation 992 and the measurement 994 is analogous to the activation and deactivation and measurement described above with respect to the debris monitoring routine 900 such that, in some implementations, the same set of measurements is used as part of the debris monitoring routine 900 and the bin-full detection routine 990.

The amount of debris in the bin is determined 996 based at least in part on comparing a first reflective signal to a first transmissive signal, where the reflective signal is derived from a measurement by the first receiver 802A when the first emitter array 804A is activated and the second emitter array 804B is deactivated and the transmissive signal is derived from a measurement by the first receiver 802A when the first emitter array 804A is deactivated and the second emitter array 804B is activated.

For the sake of clarity of description, the bin-full detection routine 990 has been described as determining whether the bin is full based on measuring signals at the first receiver 802A. However, it should be noted that the debris monitoring routine 900 can additionally or alternatively include analogous measurements of signals at the second receiver 802B.

Figure 9D:
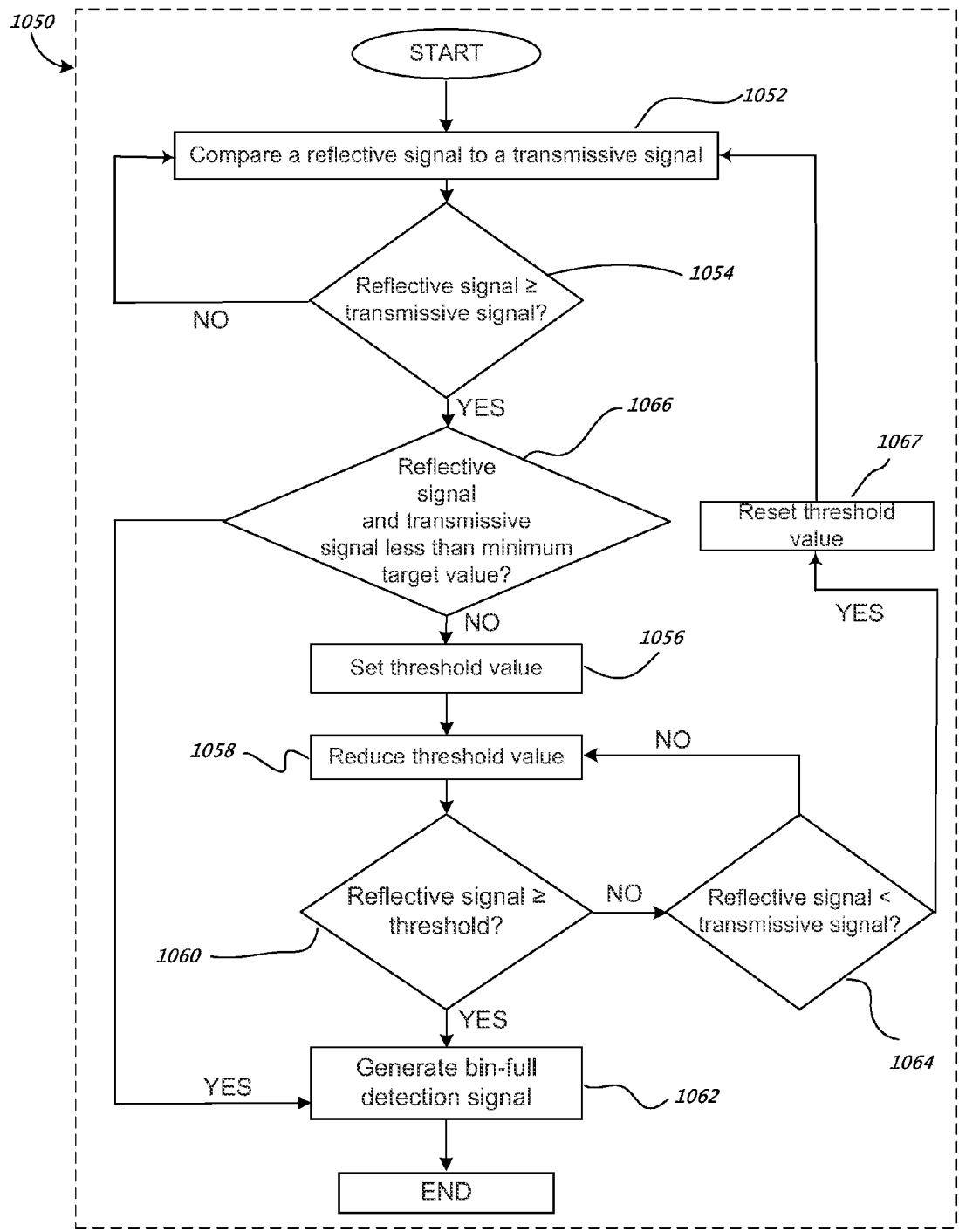
FIG. 9D is a process flow chart of a threshold setting routine.

Referring to FIG. 9D, determining 996 whether the bin 50 is full of debris may include a threshold setting routine 1050. The threshold setting routine 105 may be implemented through communication between the optical detection system 800 and one or more of the bin microprocessor 217 and the microprocessor 245.

The threshold setting routine 1050 includes comparing 1052 a measured reflective signal to a measured transmissive signal (e.g., the reflective and transmissive signals measured by the first receiver 802A and/or the second receiver 802B). In some implementations, the comparison 1052 of the measured reflective signal to the measured transmissive signal is based on an average (e.g., time-averaged) value of each signal. Such averaging can reduce the likelihood of false positive bin-full results by, for example, reducing the impact of spurious and/or transient conditions on bin-full detection. In certain implementations, the measured reflective signal and the measured transmissive signal are compared 1052 at a rate of 1 Hz to 100 Hz (e.g., about 60 Hz).

If the measured reflective signal is less than the measured transmissive signal 1054, the threshold setting routine 1050 continues to compare the measured reflective signal to the measured transmissive signal. Such a condition represents a bin that is relatively empty since light emitted by an emitter array (e.g., emitter arrays 804A,B) generally reaches a receiver (e.g., receivers 802A,B) disposed across the mouth 53 of the bin. If the measured reflective signal is greater than or equal to the measured transmissive signal 1054, the reflective signal is compared to the transmissive signal to determine 1066 whether both signals are less than a minimum target value (e.g., equal to zero or about equal to zero). This reflects an anomalous condition, such as extremely rapid filling of the bin. If both signals are equal to zero, a bin-full signal is generated 1062.

The value at which the reflective signal becomes greater than or equal to the transmissive signal is referred to as the crossover value and generally represents an indication that the bin is becoming full since light emitted by an emitter array is transmitted and scattered in approximately equal amounts as it is directed across the mouth 53 of the bin. In general, setting the threshold value as a function of the crossover value of the receiver can serve to self-calibrate the bin-full detection.

In some implementations, setting 1056 the threshold includes multiplying the crossover value by a fixed multiple (e.g., doubling the crossover value). In certain implementations, setting 1056 the threshold includes multiplying the crossover value by a value proportional (e.g., directly proportional, inversely proportional) to the value of the crossover point. Additionally or alternatively, setting 1056 the threshold can include multiplying the crossover value by a value proportional (e.g., directly proportional, inversely proportional) to the amount of time in which the crossover point was reached and/or to the peak transmissive signal.

The set threshold value can be reduced 1058 in a regular decrement over time. This can ensure that a bin-full condition will eventually be reached and, thus, reduces the likelihood that the robot 11 will continue to attempt to clean in the event of an error or an anomalous condition.

The reflective signal is compared 1060 to the set threshold. Given that the bin-filling process is generally slow, this comparison can be done at a relatively low frequency of about 1 Hz to about 100 Hz (e.g., about 60 Hz).

If the reflective signal is greater than or equal to the set threshold, a bin-full signal is generated 1062. In some implementations, the threshold value is set as an average of the signals measured by the first and second receivers 802A,B. Additionally or alternatively, the generation 1062 of a bin full signal can be based at least upon a comparison of the threshold to an average of the reflected signals measured by the first and second receivers 802A,B. As described in further detail below, this bin-full signal can be used to alert the user to the bin-full condition. In certain implementations, the bin-full signal is used to initiate a navigation routine to find a docking station (e.g., maintenance station 1250). Additionally or alternatively, the generation 1062 of the bin-full signal can disable at least a portion of the cleaning head 40 such that additional debris is not drawn into the bin 50.

The reflective signal continues to be compared to the transmissive signal to determine 1064 whether the reflective signal has become less than or equal to the transmissive signal after having been greater than the transmissive signal (this is sometimes referred to as becoming "uncrossed"). If the reflective signal is greater than or equal to the transmissive signal and the threshold value is set, the threshold value continues to be reduced 1058 until the reflective signal is greater than or equal to the threshold. If the reflective signal becomes less than the transmissive signal after the threshold value has been set, the threshold value is reset 1067 (e.g., set to a large value and/or resetting a flag) and the reflective signal continues to be compared to the transmissive signal 1054 to determine 1054 a new crossover point and set 1056 a new threshold. Such dynamic resetting of the threshold reduces the likelihood of false-positive bin full detection resulting from, for example, debris becomes lodged and then dislodged in the debris bin 50.

Although the optical detection system 800 has been described as being implemented in an autonomous, robot cleaning device, the optical detection system 800 can be additionally or alternatively incorporated into a non-autonomous cleaning device (e.g. a conventional vacuum cleaner).

The debris signal from a debris detection system (e.g., an optical detection system such as the optical detection system 800 or a piezoelectric debris detection system) can be used to alter operation of the robot 11, including selecting a behavioral mode (such as entering into a spot cleaning mode), changing an operational condition (such as speed, power or other), steering in the direction of debris (particularly when spaced-apart left and right debris sensors are used to create a differential signal), or taking other actions. For example, based at least on a detected debris signal, the robot 11 can substantially immediately begin movement through a spot coverage pattern, including the spot coverage patterns described in further detail below. The microprocessor 25 can move the robot 11 through one or more of the spot coverage patterns below by controlling the drive assembly 210 based at least in part on a signal received from the gyroscope 71. For example, the signal received from the gyroscope 71 can allow the robot 11 to move in a direction relative to the sensed debris and/or to return to the position of the sensed debris.

Figure 9E:
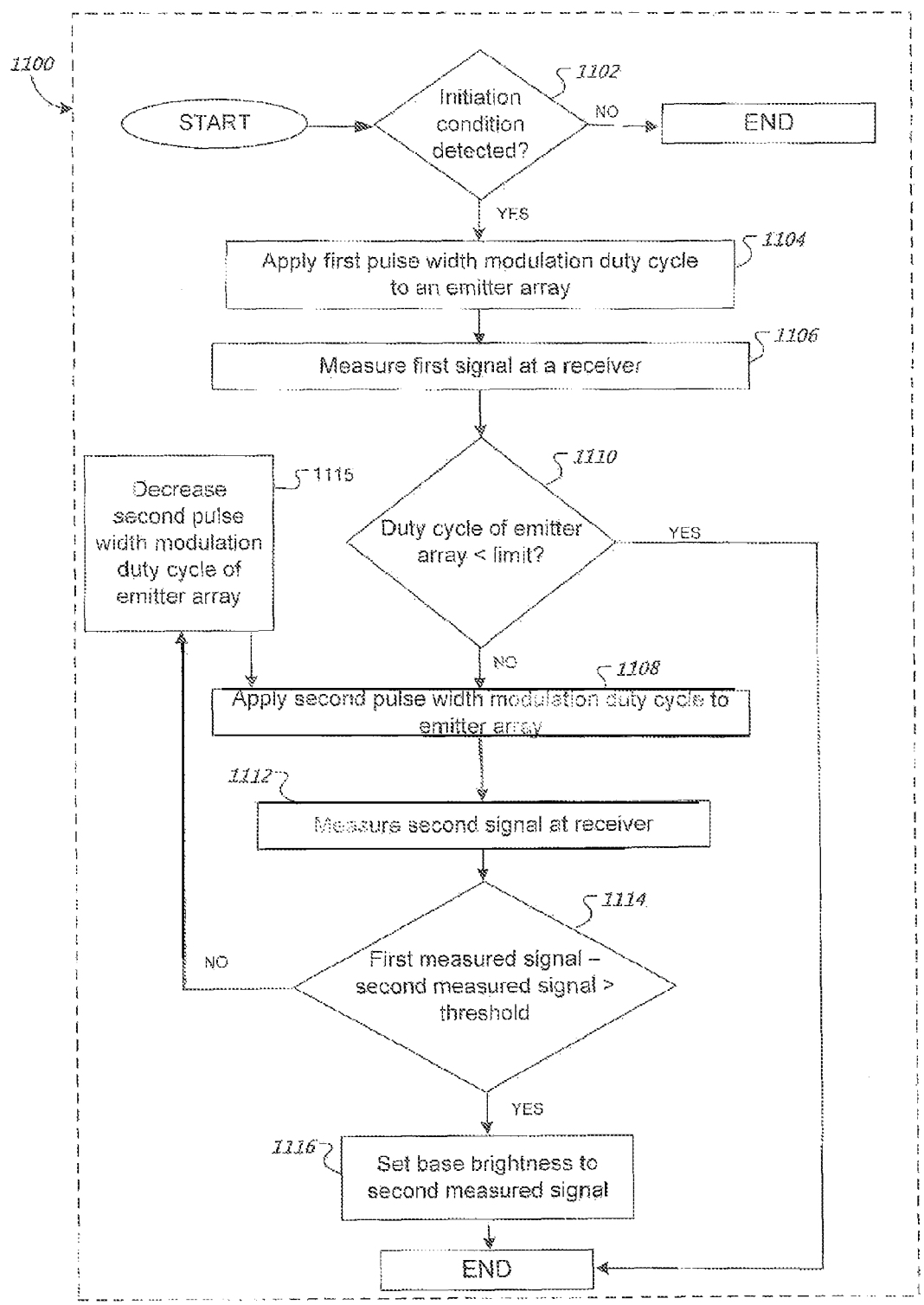
FIG. 9E is a process flow chart of a calibration routine.

Referring to FIG. 9E, in some implementations, the optical detection system 800 includes a dynamic calibration routine 1100 to set 1116 base brightness used for debris detection (e.g., through the debris monitoring routine 900 shown in FIG. 9A and described above). As indicated above, the base brightness can be subtracted from subsequent signals received at receivers 802A,B to improve, for example, the accuracy of debris detection. In some implementations, the calibration routine 1100 can activate and/or deactivate a bin-full indicator (e.g., bin full indicator 1015 in FIG. 12A) based at least in part on determining whether the bin is full. The dynamic calibration routine 1100 may be implemented through communication between the optical detection system 800 and one or more of the bin microprocessor 217 and the microprocessor 245.

The dynamic calibration routine 1100 includes applying 1104 a first pulse width modulation duty cycle to the first emitter array 804A if an initiation condition is detected 1102 and measuring 1106 the signal from the first emitter array 804A at the second receiver 802B. If the duty cycle of the first emitter array 804A is determined 1110 to be greater than a limit, a second pulse width modulation duty cycle is applied 1108 to the first emitter array 804A and a second signal is measured 1112 at the second receiver 802B. If the difference between the first measured signal and the second measured signal is greater than a threshold, the measured 1112 second signal is set 1116 as the base brightness. As used herein, a pulse width modulation refers to controlling the average value of power supplied to a load (e.g., the first emitter 804A) by turning the power to the load on and off at a fast pace, and the duty cycle describes the proportion of "on" time to the regular interval. Thus, as compared to a lower pulse width modulation duty cycle, a higher pulse width modulation duty cycle corresponds to higher power provided to the load since the power is "on" for a longer period of time.

Detecting 1102 the initiation condition can include detecting insertion of the bin 50 into the robot body 31. Additionally or alternatively, detecting 1102 an initiation condition can include detecting application of power (e.g., insertion of a battery 25 into robot body 31 and/or position of a power switch) to the autonomous robotic cleaner 11. In some implementations, detecting 1102 the initiation condition can include activating a bin-full indicator based at least in part on detecting the initiation condition. For example, upon detection 1102 of insertion of the bin 50 into the robot body 31 a bin full indicator can be activated. As used herein, a bin full indicator can include a visual indicator (e.g., a light emitting diode and/or a text message on a user interface) and/or an audible indicator (e.g., an alarm).

Applying 1104 the first pulse width modulation duty cycle to the first emitter 804A can include applying a maximum pulse width modulation duty cycle to the first emitter 804A.

Measuring 1106 the first signal at the second receiver 802B can include measuring the unreflected portion of the signal from the first emitter array 804A. For example, as described above, the first emitter array 804A can be arranged to emit a signal across at least a portion of the mouth 53 of the bin 50. Additionally or alternatively, measuring 1106 the first signal at the second receiver 802B can include measuring a reflected portion of the signal from the second emitter 804B proximate to the second receiver.

Applying 1108 the second pulse width modulation duty cycle to the first emitter array 804A includes lowering the pulse width modulation duty cycle from the first pulse width modulation duty cycle. In some implementations, the second pulse width modulation duty cycle is lowered by a fixed percentage from the previous pulse width modulation duty cycle. Additionally or alternatively, the second pulse width modulation duty cycle can be lowered by progressively larger percentages with each iteration of applying 1108 the second pulse width modulation duty cycle to the first emitter 804A.

Determining 1110 whether the pulse width modulation duty cycle of the first emitter array 804A is greater than a limit can include comparing the pulse width modulation duty cycle of the first emitter array 804A to a limit stored in one or more of the bin microprocessor 217 and the microprocessor 245. For example, the limit can be less than 90 percent (e.g., less than 50 percent, less than 40 percent) of the maximum pulse width modulation duty cycle of the first emitter array 804A. Additionally or alternatively, the limit can be any value greater than zero.

If the determination 1110 is that the pulse width modulation duty cycle of the first emitter array 804A is less than the limit while the difference between the first measured signal and the second measure signal is less than the threshold, the dynamic calibration routine 1100 can end. Such termination of the dynamic calibration routine 800 indicates that the measured signal at the first emitter array 804A is not changing sufficiently with a corresponding change in the first and second measured signals. This insufficient change in the measured signal at the first emitter array 804 can indicate that debris was present in the bin 50 during the initiation condition. For example, an insufficient change in the measured signal at the first emitter array 804A can indicate that debris was present in the bin 50 when the bin 50 was inserted in the robot body 31. Additionally or alternatively, an insufficient change in the measured signal at the first emitter array 804A can indicate that debris was present in the bin 50 when a battery was inserted into the robot body 31 and/or when power was provided to the optical detection system 800. Accordingly, in implementations in which the bin full indicator is activated based at least in part on the detection of the initiation 1102 condition, the bin full indicator can remain activated upon termination of the dynamic calibration routine 1100.

Measuring 1112 the second signal at the second receiver 802B can be analogous to measuring 1106 the first signal at the second receiver 802B.

Determining 1114 whether the difference between the first measured signal and the second measured signal is greater than a threshold can include comparing the first measured signal to the second measured signal after each signal has been processed. For example, each of the first and second measured signals can be processed through a low band pass filter. The threshold used in the determination 1114 can be a constant stored in one or more of the bin microprocessor 21 and the microprocessor 245.

If the determination 1114 is that the difference between the first measured signal and the second measured signal is less than or equal to the threshold, the second pulse width modulation duty cycle is decreased 1115 from the second pulse width modulation duty cycle from the previous iteration. In some implementations, the second pulse width modulation duty cycle is decreased 1115 by between about 1 percent to about 30 percent (e.g., about 10 percent) in each successive iteration. In certain implementations, the second pulse width modulation duty cycle is decreased 1115 by progressively larger amounts in each successive iteration.

If the determination 1114 is that the difference between the first measured signal and the second measured signal is greater than the threshold, the second measured signal is set to the base brightness (e.g., through storage in one or more of the bin microprocessor 21 and the microprocessor 245). Additionally or alternatively, a bin-full indicator can be deactivated based at least in part on the determination 1114 that the difference between the first measured signal and the second measured signal is greater than the threshold. For example, the determination 1114 of a difference greater than the threshold can be an indication that the bin 50 is not full upon the initiation condition and, thus, the bin-full indicator can be deactivated.

While the dynamic calibration routine 1100 is described herein as being based on signals emitted from the first emitter array 804A and received at the second receiver 802B, it should be appreciated that the dynamic calibration routine 1100 can additionally or alternatively be based on signals emitted from the second emitter array 804B and received at the first receiver 802A.

Figure 10A:
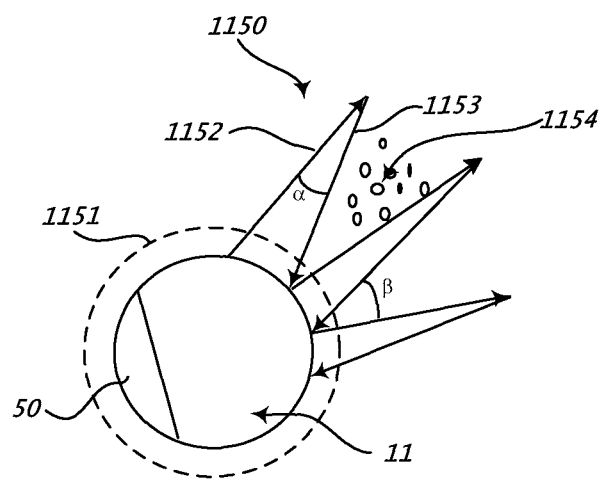
FIG. 10A is a schematic of a robot cleaning pattern.

Referring to FIG. 10A, the robot 11 can include a spot cleaning mode (sometimes referred to as a spot coverage mode) including a star pattern 1150 having pairs of outward swaths 1152 and inward swaths 1153 emanating from a central region 1151. Each pair of swaths 1152, 1153 defines an included angle α and is angularly stratified from an adjacent pair of swaths 1152, 1153 by an external angle β. The repeated back and forth pattern of the star pattern 1150 can approximately mimic the cleaning pattern commonly used by operators of handheld vacuum cleaners.

To maneuver through the star pattern, the robot 11 moves in a forward direction of travel from a central region 1151 along an outward swath 1152 and reverses direction to return to the central region 1151 along an inward swath 1153. This process can be repeated such that the robot 11 traces the star pattern 1150 corresponding to the plurality of pairs of swaths 1152, 1153. The star pattern 1150 can extend 180 degrees about the central region 1151. In certain implementations, the central region 1151 is substantially centrally oriented relative to an area of detected debris 1154. In some implementations, the central region 1151 is substantially peripherally oriented relative to an area of detected debris 1154.

The robot 11 can move through the star pattern 1150 in a clockwise or counterclockwise direction. For example, the direction of movement of the robot 11 through the star pattern 1150 can be at least partly based on a determination of the direction of debris (e.g., based on a comparison of measured signals at the first and second receivers 802A,B of the optical detection system 800).

The length of the outward swath 1152 can be a fixed length. For example, the length of the outward swath 1152 can be between 0.5 and 5 (e.g., 1) times a dimension of the robot 11 (e.g., the fore-aft dimension of the robot). As another example, the length of the outward swath 1152 can be a function of a quantity of debris detected by the debris detection system in the central region 1151 such that the length of the outward swath 1152 is inversely proportional to the quantity of debris detected by the debris detection system in the central region 1151 such that the robot 11 moves through a smaller star pattern 1150 in areas of higher debris concentration.

In certain implementations, the length of the outward swath 1152 can be a variable length. For example, the robot 11 can proceed along the outward swath 1152 until a detected quantity of debris falls below a threshold amount (e.g., indicating the perimeter of a high-debris area)

The included angle α between each outward swath 1152 and a corresponding inward swath 1153 is 0 to 45 degrees. In certain implementations, the included angle α is swept by turning the robot 11 (clockwise or counterclockwise) substantially in place at the end of the outward swath 1152 before reversing the direction of the robot 11 to move along the inward swath 1153. In some implementations, the value of the included angle α is at least partly based on a quantity of debris detected by the debris detection system (e.g., optical detection system 800). For example, the angle α can be at least partly determined by the amount of debris detected as the robot 11 moves from the central region 1151, along the outward swath 1152. In such an implementation, the detection of a relatively large amount of debris along the outward swath 1152 can result in a small included angle α such that there is significant overlap in the paths cleaned by the robot along the outward and inward swaths 1152, 1153.

In certain implementations, the external angle β between adjacent swath pairs 1155 is greater than 0 degrees and less than about 90 degrees. The external angle β can be fixed relative to the included angle α. For example, the external angle β can be substantially equal to the included angle α. Additionally or alternatively, the external angle β can be set according to one or more of the criteria described above with respect to the included angle α.

In some implementations, the external angle β is between about −90 degrees and about 90 degrees. In such implementations, the robot 11 can move along the star pattern 1150 by moving both clockwise and counterclockwise such that adjacent swath pairs 1155 can partially and, in some instances, completely overlap.

In certain implementations, cliff sensors 30A and 30B (shown in FIG. 1B) disposed along the respective forward and rear portions 31A,B of the robot 11 can reduce the likelihood that the robot 11 will maneuver over a cliff while executing the star pattern 1150 or another cleaning pattern including repeated backward and forward motion. For example, cliff sensors 30A disposed along the forward portion of the robot 31A can detect a potential cliff forward of the robot 11 as the robot moves in the forward direction and cliff sensors 30B disposed along the rear portion of the robot 31B can detect a potential cliff rear of the robot 11. In response to a potential cliff detected by the cliff sensors 30A and/or cliff sensors 30B, the robot 11 can abort the spot coverage pattern and, for example, initiate avoidance and/or an escape behavior. Thus, as compared to a robot with cliff sensors along only a forward portion, the robot 11 can execute a wider array of cleaning patterns including, for example, cleaning patterns that do not require the robot 11 to be in a specific forward orientation.

Figure 10B:
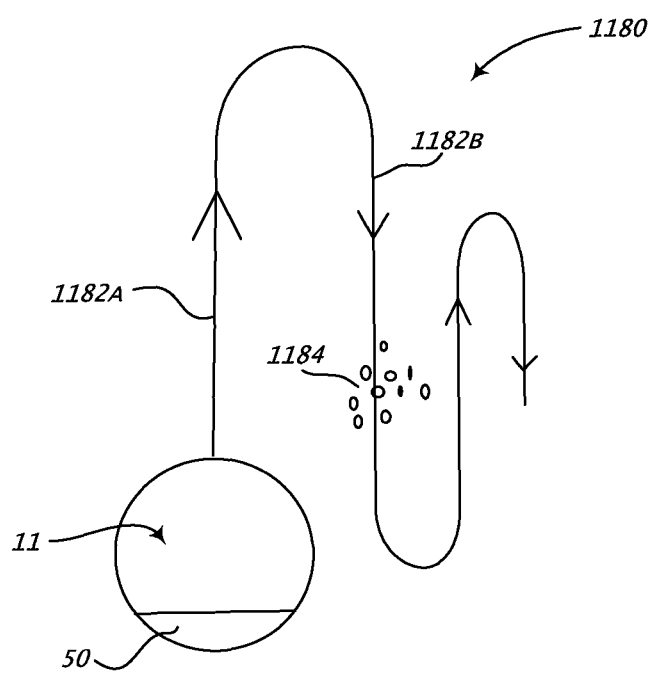
FIG. 10B is a schematic of a robot cleaning pattern.

In certain implementations, referring to FIG. 10B, the robot 11 includes a spot cleaning mode including a "cornrow" pattern 1180 having repeated adjacent rows 1182. The robot 11 can initiate movement through the cornrow pattern 1180 at least partially based on the detection of debris 1184 on the cleaning surface. Additionally or alternatively, each row 1182 can extend substantially perpendicular to a detected direction of debris 1184 (e.g., as detected by first and second receivers 802A,B of the optical detection system 800).

The robot 11 can move along the cornrow pattern 1180 by moving along a row 1182a until a quantity of detected debris (e.g., as determined by the optical detection system 800) falls below a threshold and then moving the robot 11 in a substantially opposite direction along an adjacent row 1182b and repeating this pattern for a set period of time or until the robot 11 moves through one or more rows without detecting a quantity of debris above the threshold.

In some implementations, the robot moves along the adjacent rows 1182a,b such that the adjacent rows 1182a,b overlap. The amount of overlap can be a fixed amount such as, for example, a fixed multiple (e.g., one half) of the size of the cleaning head. Additionally or alternative, the amount of overlap between certain adjacent rows 1182a,b can be based at least in part on the quantity of debris 1184 detected by the robot 11, with the degree of overlap being directly proportional to the quantity of debris 1184 detected.

While the robot 11 has been described as operating in a spot coverage mode to move through the star pattern 1150 and the cornrow pattern 1180 based at least in part on a detected debris signal, other types of patterns are additionally or alternatively possible. For example, the robot 11 can move through an inward spiral pattern, an outward spiral pattern, and/or a zig-zag pattern.

Figure 11:
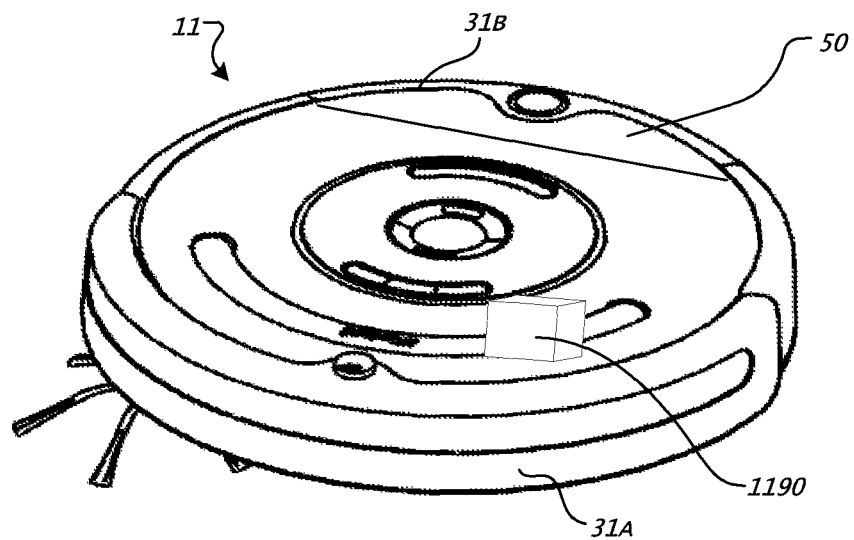
FIG. 11 is a perspective view of a robot.

Referring to FIG. 11, in some implementations, the robot 11 includes a camera 1190 disposed toward the forward portion of the robot 11, with a field of view beyond the perimeter of the robot 11. This camera 1190 can be in communication with the microprocessor 245 such that the movement of the robot 11 over the cleaning surface can be based at least in part on the detection of debris and/or an obstacle by the camera 1190. For example, the microprocessor 245 can process the signal from the camera 1190 to recognize debris on the cleaning surface and maneuver the robot 11 toward the debris.

Additionally or alternatively, the microprocessor 245 can process the signal from the camera 1190 to recognize obstacles and/or debris in the vicinity of the robot 11 and maneuver the robot 11 to avoid obstacles and/or debris larger than a specific size threshold (e.g., a value less than about the smallest opening defined by the cleaning head).

Figure 12A:
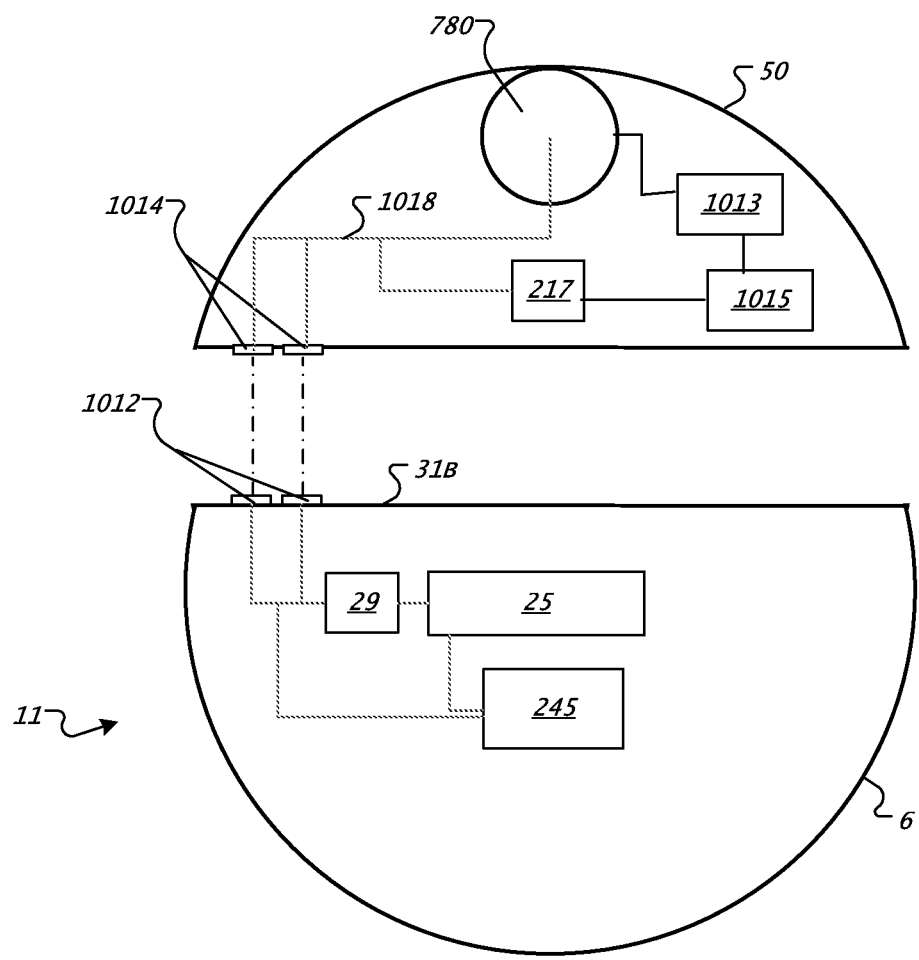
FIGS. 12A-12B are schematic views of autonomous robotic cleaners.
Figure 12B:
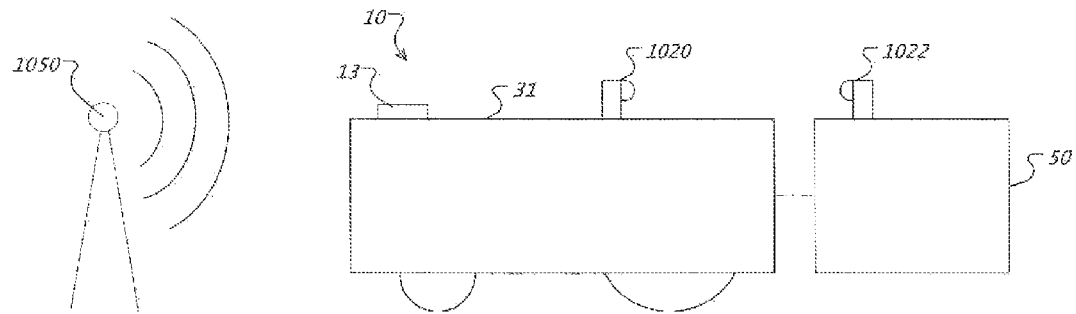

Referring to FIGS. 12A-12B, in some implementations, the robot 11 includes robot communication terminals 1012 and the bin 50 includes bin communication terminals 1014. Information regarding bin-full status is communicated from the bin 50 to the robot 11 via the communication terminals 1012, 1014, for example. Additionally or alternatively, a cliff detection signal from one or more rear cliff sensors 30B disposed on the bin 50 is communication from the bin to the robot 11 via the communication terminals 1012, 1014. In some implementations, the bin communication terminals 1014 contact the corresponding robot communication terminals 1012 when the bin 50 is attached to the robot 11. In some examples, the communication terminals 1012, 1014 include serial ports operating in accordance with an appropriate serial communication standard (e.g. RS-232, USB, or a proprietary protocol).

In some examples, the robot 11 includes a demodulator/decoder 29 through which power is routed from the battery 25 through the communication terminals 1012, 1014 and to the bin 50. Bin power/communication lines 1018 supply power to a vacuum motor 780, a bin microcontroller 217, and the rear cliff sensor 30B. The bin microcontroller 217 monitors the bin-full status reported by the debris detection system 700 in the bin 50, and piggybacks a reporting signal onto the power being transmitted over the bin-side lines 1018. The piggybacked reporting signal is then transmitted to the demodulator/decoder 29 of the robot 11. The microprocessor 245 of the robot 11 processes the bin full indication from the reporting signal piggybacked onto the power lines 1018, for example.

In certain implementations, the bin microcontroller 217 monitors the bin-full status reported by the debris detection system 700 in the bin 50 (e.g., independently of a robot controller), allowing the bin 50 to be used on robots without a debris detection system 700. A robot software update may be required for the bin upgrade.

In some implementations, as shown in FIG. 12A, the bin 50 includes a bin power source 1013 (e.g., a battery) in electrical communication with the bin microcontroller 217, the vacuum motor 780, a bin-full indicator 1015, and/or a rear cliff sensor 30B disposed on the bin 50. The bin microcontroller 217 may control power to the vacuum motor 780, based at least in part on the bin-full status reported by the debris detection system 700. For example, the bin microcontroller 217 may disable power to the vacuum motor 780 upon detection of a bin-full condition reported by the debris detection system 700. Additionally or alternatively, the bin microcontroller 217 may control the status of the bin-full indicator 1015 (e.g., an LED) to provide the user with a visual indication of the status of the bin (e.g., the bin is full if the bin-full indicator 1015 is illuminated). Powering the bin-full indicator 1015 with the bin power source 1013 allows the bin-full indicator 1015 to remain illuminated while the bin 50 is disengaged from the robot 11 (e.g., while the bin 50 is being emptied).

Figure 15A:
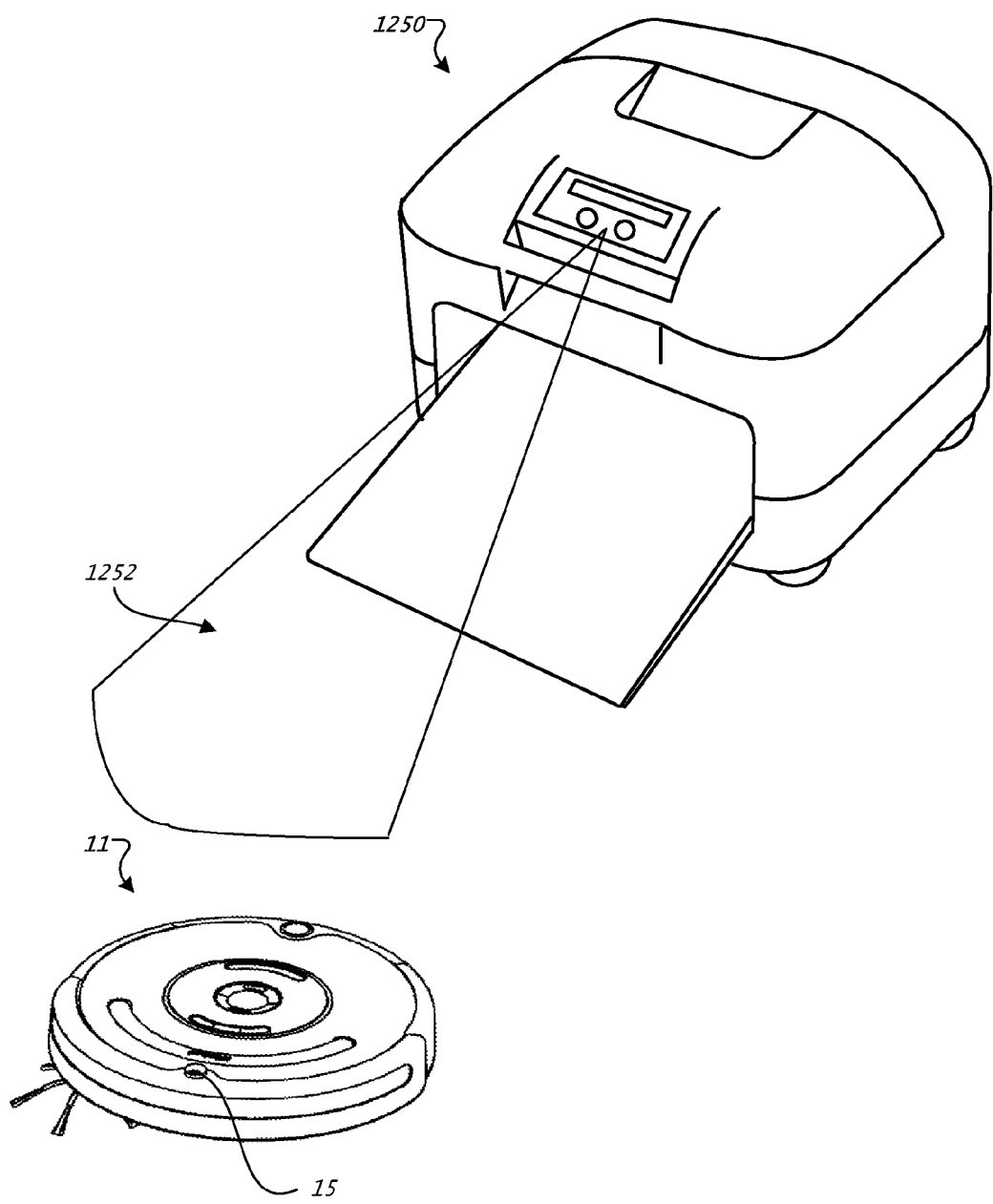
FIG. 15A is a schematic view of an autonomous robotic cleaner and an evacuation station.

Referring to FIG. 12B, in some implementations, the robot 11 includes a receiver 1020 (e.g., an infrared receiver) and the bin 50 includes a corresponding emitter 1022 (e.g., an infrared emitter). The emitter 1022 and receiver 1020 are positioned on the bin 50 and robot 11, respectively, such that a signal transmitted from the emitter 1022 reaches the receiver 1020 when the bin 50 is attached to the robot 11. For example, in implementations in which the receiver 1020 and the emitter 1022 are infrared, the emitter 1022 and the receiver 1020 are positioned relative to one another to facilitate line-of-sight communication between the emitter 1022 and the receiver 1020. In some examples, the emitter 1022 and the receiver 1020 both function as emitters and receivers, allowing bi-directional communication between the robot 11 to the bin 50. In some examples, the robot 11 includes an omni-directional receiver 13 on the chassis 31 and configured to interact with a remote virtual wall beacon 1050 that emits and receives infrared signals. A signal from the emitter 1022 on the bin 50 is receivable by the omni-directional receiver 13 and/or the remote virtual wall beacon 1050 to communicate a bin fullness signal. If the robot 11 was retrofitted with the bin 50 and received appropriate software, the retrofitted bin 50 can direct the robot 10 to return to a maintenance station (e.g., maintenance station 1250 in FIGS. 15A,B) for servicing when the bin 50 is full. While infrared communication between the robot 11 and the bin 50 has been described, one or more other types of wireless communication may additionally or alternatively be used to achieve such wireless communication. Examples of other types of wireless communication between the robot 11 and the bin 50 include electromagnetic communication and radiofrequency communication.

Figure 13A:
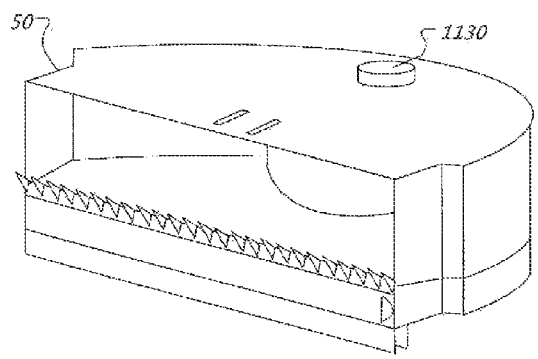
FIG. 13A is a perspective view of a cleaning bin.
Figure 13B:
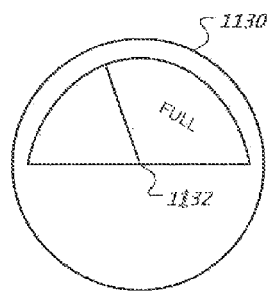
FIGS. 13B-13D are schematic views of cleaning bin indicators.
Figure 13C:
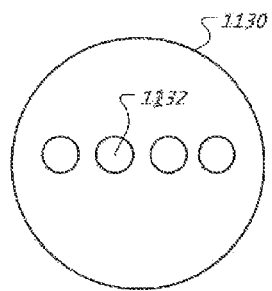
Figure 13D:
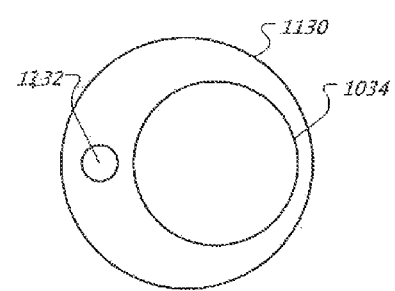

Referring to FIGS. 13A-13D, in some implementations, the bin 50 includes a bin-full indicator 1130. In some examples the bin-full indicator 1130 includes visual indicator 1132 such as an LED (FIG. 13B), LCD, a light bulb, a rotating message wheel (FIG. 13C) or a rotating color wheel, or any other suitable visual indicator. The visual indicator 1132 may steadily emit light, flash, pulse, cycle through various colors, or advance through a color spectrum in order to indicate to the user that the bin 50 is full of debris, inter alia. The indicator 30 may include an analog display for indicating the relative degree of fullness of the bin 50. For example, the bin 50 includes a translucent window over top of a rotatable color wheel. The translucent window permits the user to view a subsection of the color wheel rotated in accordance with a degree of fullness detected in the bin 50, for example, from green (empty) to red (full). In some examples, the indicator 30 includes two or more LEDs which light up in numbers proportional to bin fullness, e.g., in a bar pattern. Alternatively, the indicator 1030 may be an electrical and/or mechanical indicator, such as a flag, a pop up, or message strip, for example. In other examples, the bin-full indicator 1130 includes an audible indicator 1134 such as a speaker, a beeper, a voice synthesizer, a bell, a piezo-speaker, or any other suitable device for audibly indicating bin-full status to the user. The audible indicator 1134 emits a sound such as a steady tone, a ring tone, a trill, a buzzing, an intermittent sound, or any other suitable audible indication. The audible indicator 1134 modulates the volume in order to draw attention to the bin-full status (for example, by repeatedly increasing and decreasing the volume). In some examples, as shown in FIG. 13D, the indicator 1130 includes both visual and audible indicators, 1132 and 1134, respectively. The user may turn off the visual indicator 1132 or audible indicator 1134 without emptying the bin 50. In some implementations, the bin-full indicator 1130 is located on the robot body 31 or shell 6 of the robot 11.

Figure 14A:
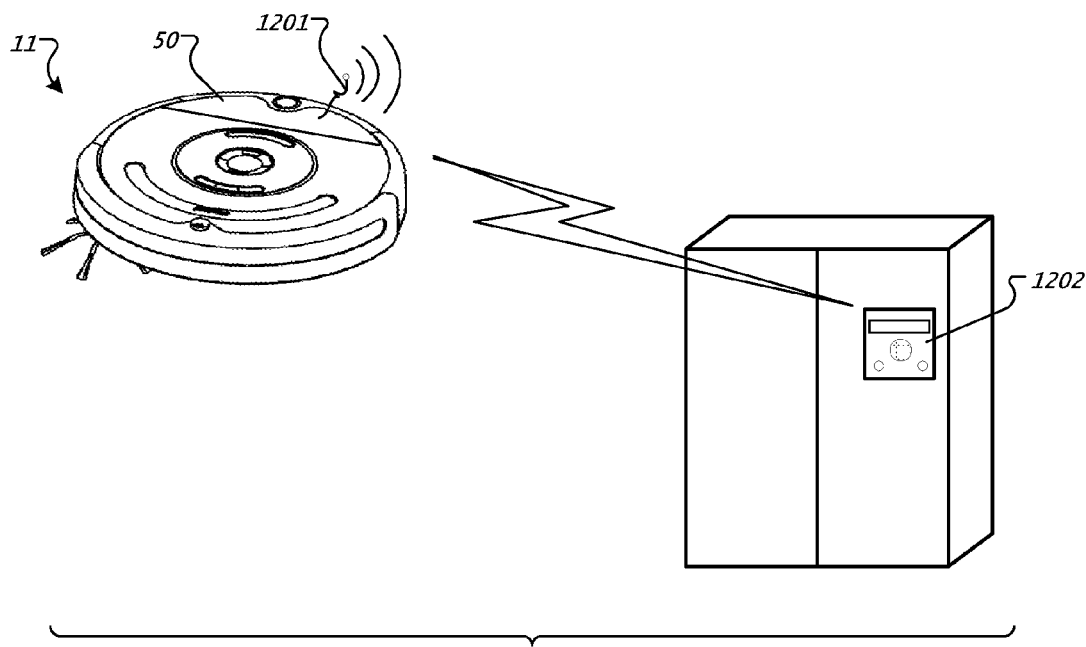
FIG. 14A is a schematic view of a cleaning bin indicator system.
Figure 14B:
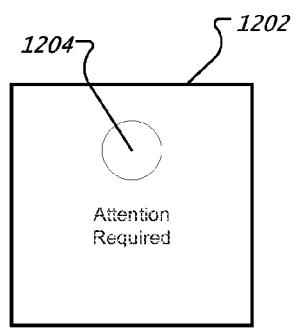
FIGS. 14B-14C are schematic views of remote cleaning bin indicators.

Referring to FIGS. 14A-14B, in some implementations, the bin 50 wirelessly transmits a signal to a remote indicator 1202 (via a transmitter 1201, for example), which then indicates to a user that the bin is full using optical (e.g. LED, LCD, CRT, light bulb, etc.) and/or audio output (such as a speaker 1208). In one example, the remote indicator 1202 includes an electronic device mounted to a kitchen magnet. The remote indicator 1202 may provide (1) generalized robot maintenance notifications (2) a cleaning routine done notification (3) an abort and go home instruction, and (4) other control interaction with the robot and/or bin 50.

An existing robot 11, which does not include any communication path or wiring for communicating with a bin-full sensor system 700 on the bin 50, is nonetheless retrofitted with a bin 50 including a bin-full sensor system 700 and a transmitter 1201. "Retrofitting" generally means associating the bin with an existing, in-service robot, but for the purposes of this disclosure, at least additionally includes forward fitting, i.e., associating the bin with a newly produced robot in a compatible manner. Although the robot 11 cannot communicate with the bin-full sensor system 700 and may possibly not include any program or behavioral routines for responding to a bin-full condition, the bin 50 may nonetheless indicate to a user that the bin 50 is full by transmitting an appropriate signal via the transmitter 1201 to a remote indicator 1202. The remote indicator 1202 may be located in a different room from the robot 11 and receives signals from the bin 50 wirelessly using any appropriate wireless communication method, such as IEEE 801.11/WiFi, BlueTooth, Zigbee, wireless USB, a frequency modulated signal, an amplitude modulated signal, or the like.

Figure 14C:
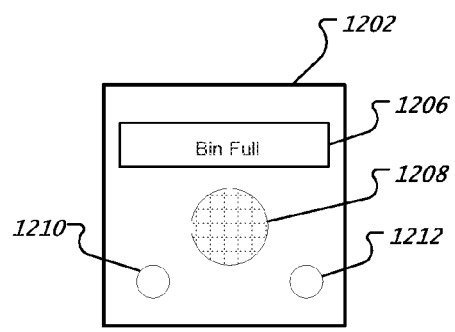

In some implementations, as shown in FIG. 14B, the remote indicator 1202 is a magnet-mounted unit including an LED 1204 that lights up or flashes when the bin 50 is full. In some examples, as shown in FIG. 14C, the remote indicator 1202 includes an LCD display 1206 for printing a message regarding the bin full condition and/or a speaker 1208 for emitting an audible signal to the user. The remote indicator 1202 may include a function button 1210, which transmits a command to the robot 11 when activated. In some examples, the remote indicator 1202 includes an acknowledge button 1212 that transmits an appropriate command signal to the mobile robot 20 when pushed. For example, when a bin-full signal is received, the LCD display 1206 may display a message indicating to the user that the bin is full. The user may then press the button 1212, causing a command to be transmitted to the robot 11 that in turn causes the robot 11 to navigate to a particular location. The user may then remove and empty the bin 50, for example.

In some examples, the remote indicator 1202 is a table-top device or a component of a computer system. The remote indicator 1202 may be provided with a mounting device such as a chain, a clip or magnet on a reverse side, permitting it to be kept in a kitchen, pendant, or on a belt. The transmitter 1201 may communicate using WiFi or other home radio frequency (RF) network to the remote indicator 1202 that is part of the computer system, which may in turn cause the computer system to display a window informing the user of the bin-full status.

Figure 14D:
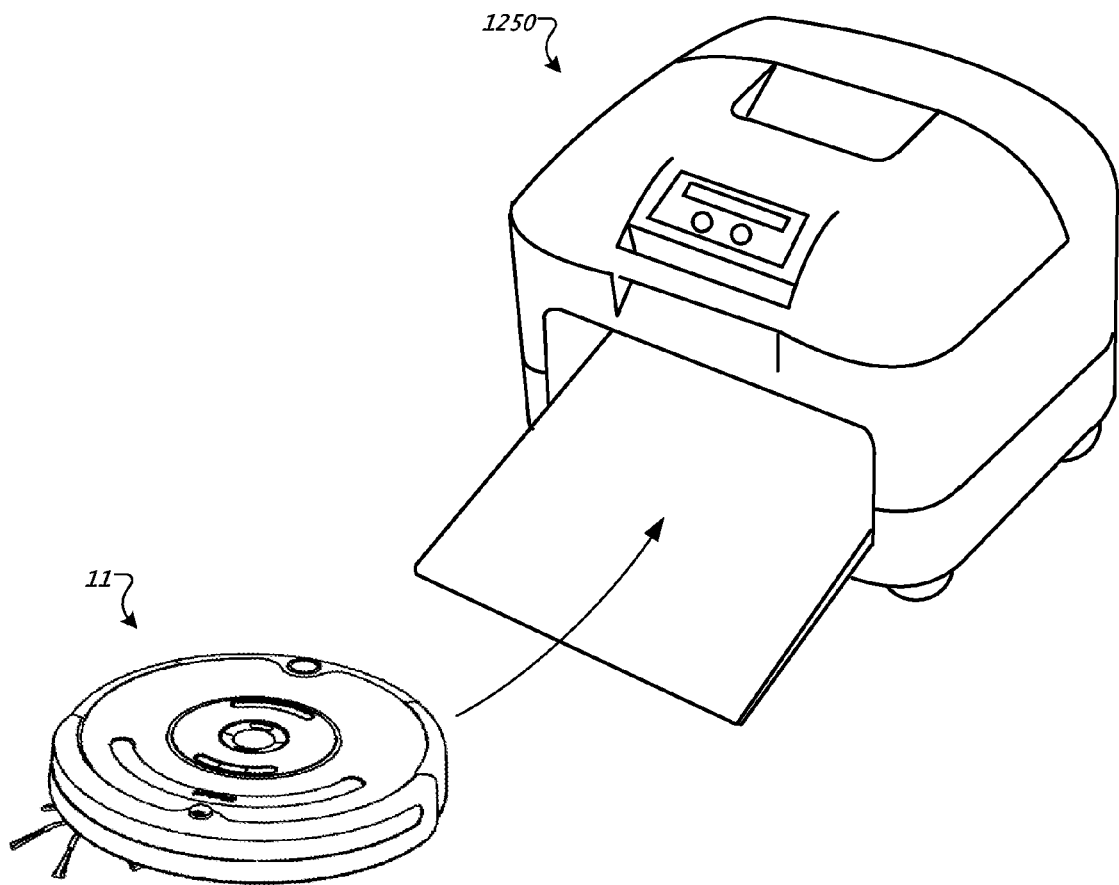
FIG. 14D is a schematic view of an autonomous robotic cleaner and an evacuation station.

Referring to FIG. 14D, when the optical detection system 800 determines that the bin 50 is full and/or when the microprocessor 245 determines that a state-of-charge of the battery 25 has fallen below a threshold, the robot 11, in some examples, maneuvers to a maintenance station 1250 (e.g., a dock) for servicing. Maneuvering the robot 11 to the maintenance station 1250 is described in further detail below.

The robot 11 releasably engages with the maintenance station 1250. In some examples, the maintenance station 1250 automatically evacuates the bin 50 (e.g. via a vacuum tube connecting to an evacuation port 80, 305, 380, 415, 420, 425, 430 of the bin 50). Additionally or alternatively, the maintenance station 1250 charges the battery 25. For example, the maintenance station 1250 can charge the battery 25 through releasable engagement with at least one charging terminal 72. In some examples, the charging terminal 72 is disposed along a bottom portion of the robot 11. Additionally or alternatively, the charging terminal 72 can be disposed along a top portion and/or a side portion of the robot 11. The at least one charging terminal 72 can be a contact terminal.

If the cleaning head 40 is full of filament build up, the robot 11 may automatically discharge the cleaning brush/flapper 60, 65 for either automatic or manual cleaning. The brush/flapper 60, 65 may be fed into the maintenance station 1250, either manually or automatically, which strips filament and debris from the brush/flapper 60, 65.

Figure 15B:
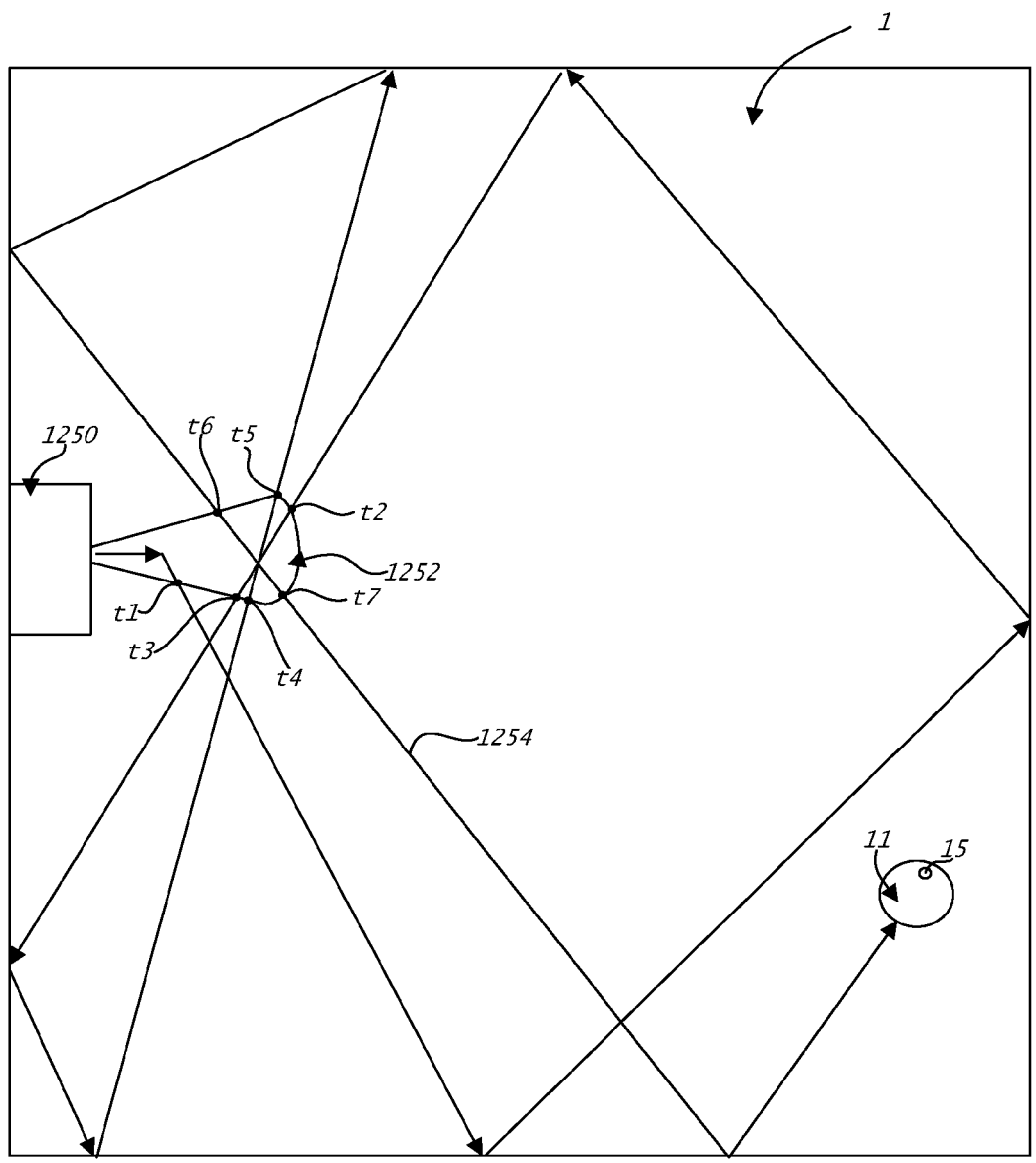
FIG. 15B is a schematic view of an autonomous robotic cleaner moving relative to an evacuation station.
Figure 16:
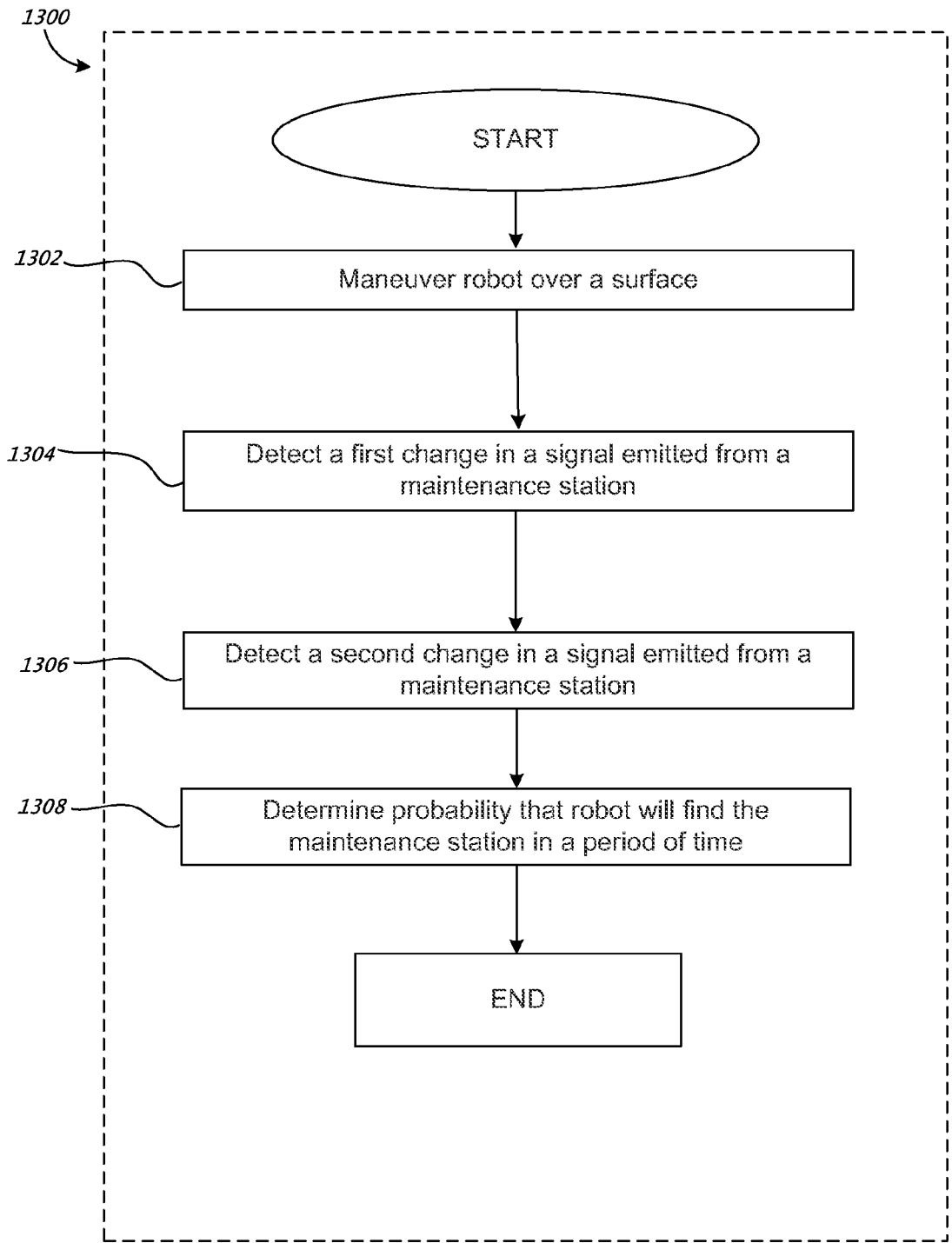
FIG. 16 is a process flow chart of a seeking routine.

Referring to FIGS. 15-16, in some examples, the maintenance station 1250 emits a signal 1252 (e.g., a single signal, multiple signals, or multiple overlapping signals). The signal 1252 can be, for example, one or more optical signals (e.g., infrared) and/or acoustic signals. The robot 11 includes a receiver 15 for receiving the signal 1252. Other details and features of signal emission by the maintenance station 1250 and signal reception by the robot 11 are disclosed in U.S. Pat. No. 7,332,890, entitled "Autonomous Robot Auto-Docking and Energy Management Systems and Methods," the entire contents of which are incorporated herein by reference.

As the robot 11 moves over a cleaning surface 1, the receiver 15 can receive the signal 1252 emitted by the maintenance station 1250 as the robot 11 moves along a path 1254 (e.g., in a bounce mode). The robot 11 can detect the time t1-t7 associated with each change in the signal 1252, with each change in the signal 1252 representing respective movement of the robot 11 into and out of the signal 1252. For example, the robot 11 detects movement out of the signal 1252 at t1 and detects movement into the signal 1252 at t2. Similarly, the robot 11 detects movement out of the signal 1252 at t3 and detects movement into the signal 1252 at t4. As described below, the microprocessor 245 of the robot 11 can seek the maintenance station 1250 based at least in part on the elapsed time between t1 and t2, t3 and t4, etc. For the sake of clarity of explanation, seven times associated with change in the signal 1252 are shown in FIG. 15B. However, it should be appreciated that the robot can detect any number of times.

In some implementations, seeking 1300 the maintenance station 1250 can include maneuvering 1302 the robot 11 over the cleaning surface 1 along path 1254, detecting 1304 a first change in a signal emitted from the maintenance station 1250, detecting 1306 a second change in the signal emitted from the maintenance station 1250, and determining 1308 the probability that the robot will find the dock in a period of time. The determination 1308 of the probability that the robot will find the dock in a period of time is based at least in part on the elapsed time between the detected 1304 first change in the signal and the detected 1306 second change in the signal. This determination 1308 can reduce, for example, the likelihood that the robot 11 will become stranded on the cleaning surface 1 without enough power to return to the maintenance station 1250. In certain implementations, the robot 11 seeks 1300 the maintenance station 1250 continuously. In some implementations, the robot 11 seeks 1300 the maintenance station 1250 periodically. Additionally or alternatively, the robot 11 can seek 1300 the maintenance station 1250 upon detection that a state-of-charge of the battery 25 is below a threshold (e.g., below about 50 percent).

Maneuvering 1302 the robot 11 over the cleaning surface can include maneuvering the robot 11 while one or more other behaviors are being executed. For example, maneuvering 1302 can include moving the robot 11 over the cleaning surface 1 in a bounce mode, a spot coverage mode, an escape mode, a migration mode, etc. Additionally or alternatively, maneuvering 1302 the robot 11 over the cleaning surface 1 can be determined by an arbiter. Details and features of such an arbiter are described in U.S. Pat. No. 7,388,343, entitled "Method and System for Multi-Mode Coverage for an Autonomous Robot," the entire contents of which are incorporated herein by reference.

Detecting 1304 the first change in the signal emitted from the maintenance station 1250 includes receiving (e.g., by receiver 15) the signal 1252 emitted from the maintenance station 1250. The detected 1304 first change in the signal can include detecting a change from receiving no signal to receipt of a signal and/or detecting a change from receipt of a signal to receipt of no signal. In some implementations, detecting 1304 the first change in the signal includes detecting an encoded signal. For example, the signal can be encoded to identify the maintenance station 1250 associated with the robot 11 such that the robot 11 does not seek a maintenance station 1250 that is not associated with the robot 11.

Detecting 1306 the second change in the signal emitted from the maintenance station 1250 includes receiving (e.g., by receiver 15) the signal 1252 emitted from the maintenance station 1250. Detecting 1306 the second change in the signal 1252 temporally follows detecting 1304 the first change in the signal such that there is an elapsed time between the detected 1304 first change in the signal and the detected 1306 second change in the signal.

Determining 1308 the probability that the robot will find the maintenance station 1250 is based at least in part on the elapsed time between detecting 1304 the first change in the signal and detecting 1306 the second change in the signal. The elapsed time between detecting 1304 the first change in the signal and detecting 1306 the second change in the signal represents the time between maintenance station 1250 sightings by the robot 11. In some implementations, the elapsed time is used to update a probability distribution based at least in part on the elapsed time and/or previously determined elapsed times. For example, the elapsed time between t6 and t5 can be used to update a probability distribution including the elapsed time between t4 and t3 and the elapsed time between t2 and t1.

The probability distribution can be used to estimate the probability that the robot 11 will reach the maintenance station 1250 within a period of time (e.g., a specified period of time or a variable period of time). For example, the probability distribution can be used to estimate the probability that the robot 11 will reach the maintenance station 1250 within five minutes.

Additionally or alternatively, the probability distribution can be used to determine the amount of time required for the robot 11 to reach the maintenance station 1250 with a certain probability. For example, the probability distribution can be used to estimate the amount of time required for the robot 11 to reach the maintenance station 1250 with greater than 75 percent probability. In some examples, the amount of time required for the robot 11 to reach the maintenance station 1250 with a certain probability can be the time allotted to allow the robot 11 to find the maintenance station 1250. Thus, in one example, if the estimated time required for the robot to reach the maintenance station 1250 with greater than 95 percent probability is five minutes and a 95 percent success rate in finding the maintenance station 1250 is desired, the robot 11 will begin attempting to find the maintenance station 1250 when the remaining battery life 25 is five minutes. To allow for a further margin of safety, the robot 11 can reduce power consumption of the battery 25 by reducing, for example, the amount of power to the cleaning head 40 during the allotted time.

In some implementations, the probability distribution of elapsed times is a non-parametric model. For example, the non-parametric model can be a probability distribution histogram of probability as a function of elapsed time. The elapsed time ranges used for resolution of the histogram can be fixed values (e.g., about 5 second to about two minute intervals).

In certain implementations, the probability distribution of elapsed times is a parametric model. For example, the parametric model can be a Poisson distribution in which a successful outcome is an outcome in which the robot 11 reaches the maintenance station 1250 within a period of time and a failure is an outcome in which the robot 11 does not reach the maintenance station 1250 within a period of time. The mean of the Poisson distribution can be estimated, for example, as the arithmetic mean of a plurality of elapsed time measurements. From the Poisson distribution, the probability that the robot 11 will reach the maintenance station 1250 within a period of time can be determined. For example, the Poisson distribution can be used to determine the probability that the robot 11 will reach the maintenance station 1250 within five minutes. As an additional or alternative example, the Poisson distribution can be used to determine the amount of time required for the robot 11 to reach the maintenance station 1250 with a certain probability (e.g., a probability of greater than 75 percent).

In some implementations, determining 1308 the probability that the robot 11 will find the maintenance station 1250 can include determining the probability that power available from the battery 25 carried by the robot 11 will be depleted before the robot 11 can find the maintenance station 1250. For example, the amount of time corresponding to the remaining power available from the battery 25 can be estimated based on the rate of power consumption of the robot 11 in the current mode of operation. The probability that the robot 11 will reach the maintenance station 1250 within the remaining battery time can be determined, for example, using the nonparametric and/or the parametric models discussed above.

If the robot 11 is removed from the cleaning surface 11, the elapsed times between successive sightings of the maintenance station 1250 may not be representative of the amount of time required for the robot 11 to find the maintenance station 1250. Thus, in some implementations, seeking 1300 the maintenance station 1250 includes ignoring a change in the detected signal following detection that the robot 11 was removed from the surface 1. For example, if the robot 11 was removed from the surface 1 between t1 and t2, the detected 1304 first change in the signal 1252 corresponding to t1 is ignored and the detected 1306 second change in the signal 1252 is also ignored such that the next elapsed time is determined as the difference between t4 and t3. In certain implementations, detecting that the robot has been removed from the surface includes receiving a signal from one or more sensors (e.g., cliff sensors 30A and 30B and/or proximity sensors 70) carried by the robot 11. Additionally or alternatively, wheels 45 can be biased-to-drop and detecting that the robot has been removed from the surface can include detecting that the wheels 45 have dropped. Details of such biased-to-drop wheels 45 and detection of dropped wheels is disclosed in U.S. Pat. No. 7,441,298, entitled "Coverage Robot Mobility," the entire contents of which are incorporated herein by reference.

Figure 17:
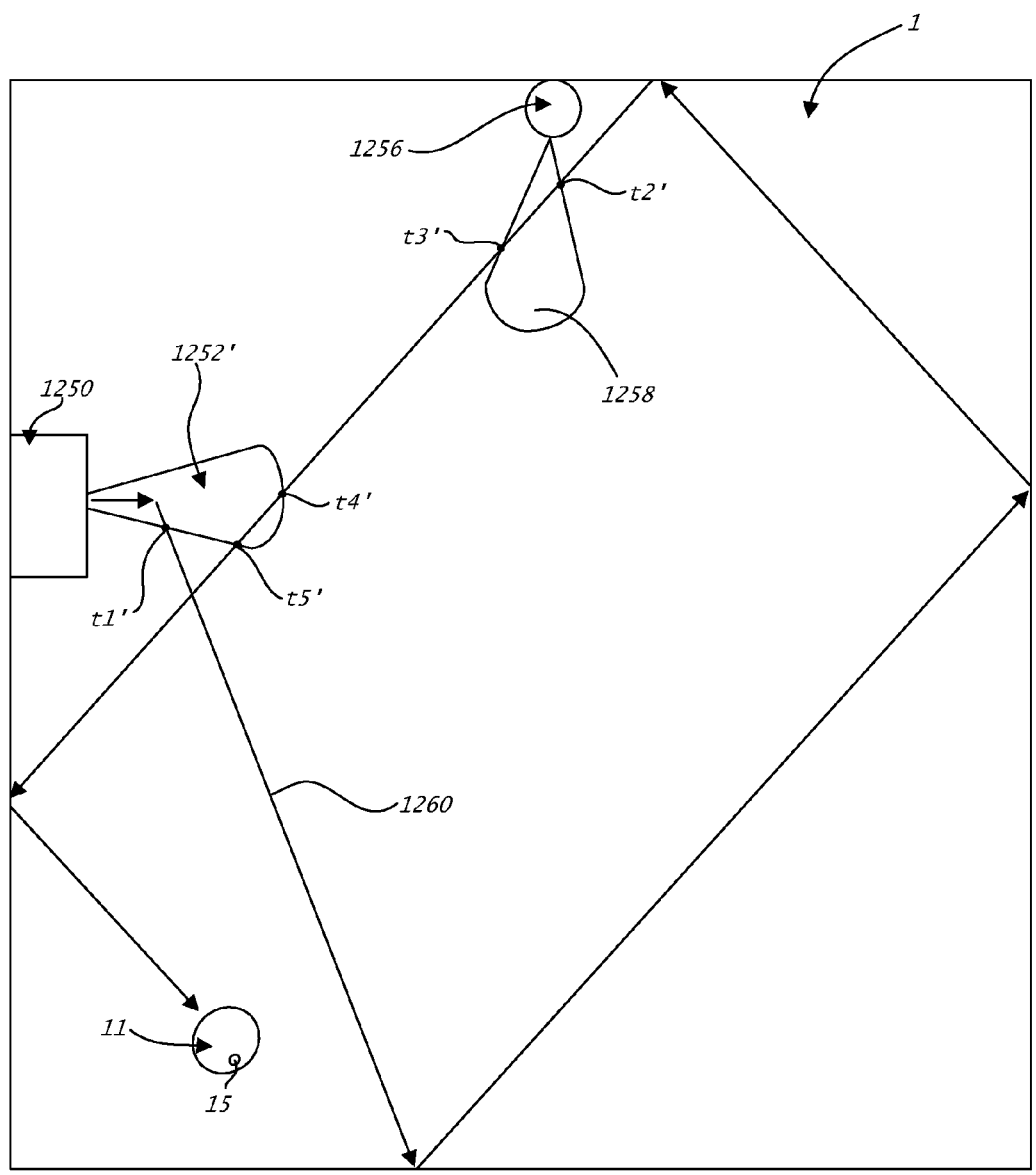
FIG. 17 is a schematic view of an autonomous robotic cleaner moving relative to an evacuation and a second structure.
Figure 18:
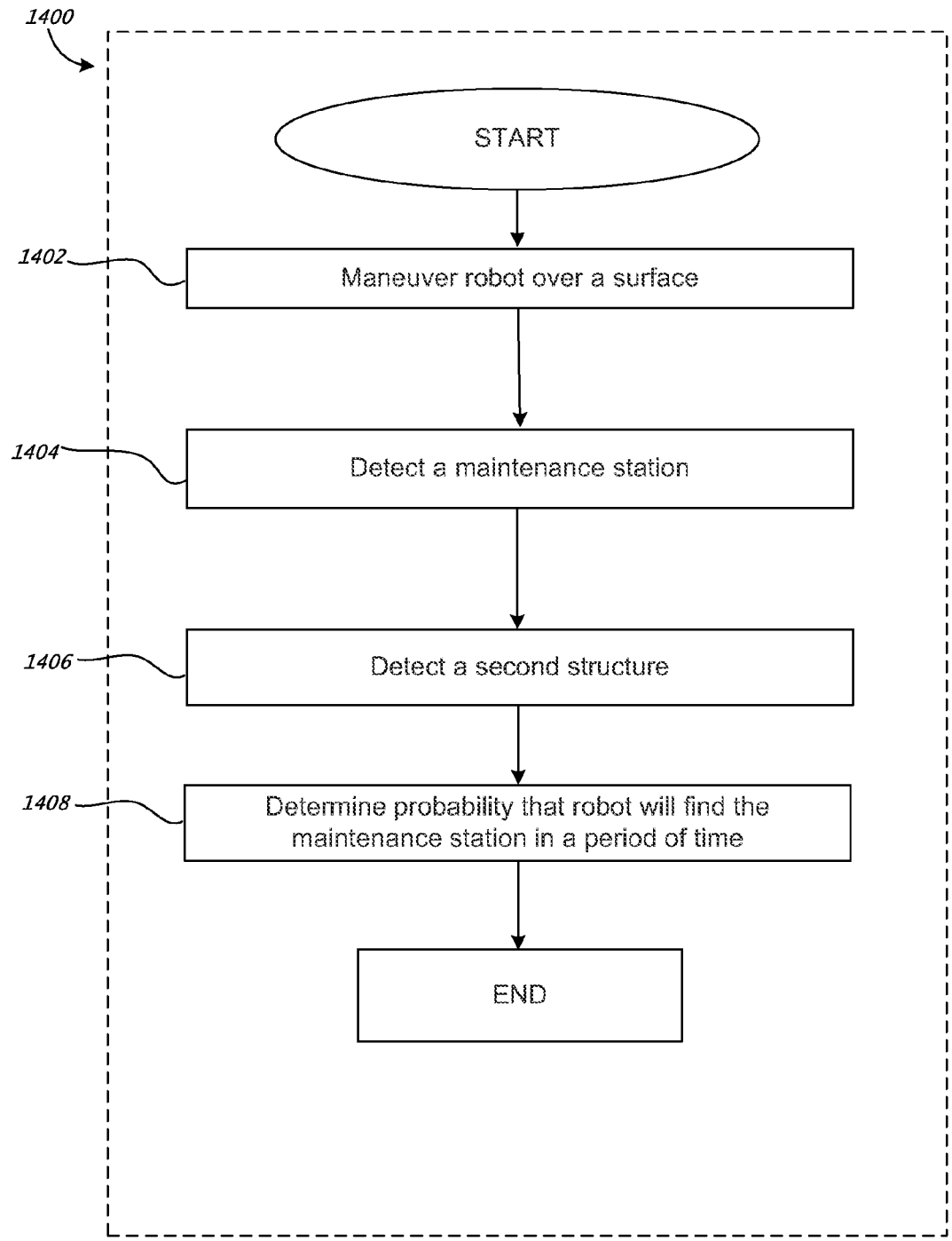
FIG. 18 is a process flow chart of a seeking routine.

Referring to FIGS. 17-18, the maintenance station 1250 emits a first signal 1252' (e.g., a single signal, multiple signals, or multiple overlapping signals) and a second structure 1258 emits a second signal 1258. The second structure 1256 can be a lighthouse (e.g., a navigation beacon), a gateway marker, a second maintenance station, etc. The robot 11 moves on the cleaning surface 1, along a path 1260 such that the robot 11 intersects the signal 1252' emitted by the maintenance station 1250 and intersects the signal 1258 emitted by the second structure 1256. The robot 11 intersects the signal 1252' at t1', t4', and t5', and the robot 11 intersects the signal 1258 at t2' and t3'. The second structure 1256 can act as a landmark to assist in the prediction of finding the maintenance station 1250. For example, as described below, the time between sighting the second structure 1256 and sighting the maintenance station 1250 can be used to predict the amount of time needed to find the dock given that the second structure 1256 was just seen.

In some implementations, seeking 1400 the maintenance station 1250 includes maneuvering 1402 the robot over the cleaning surface 1, detecting 1404 the maintenance station 1250, detecting 1406 the second structure 1256, and determining 1408 the probability that the robot will find the maintenance station 1250 within a period of time. In some implementations, the signal 1252' from the maintenance station 1250 differs from the signal 1258 emitted from the second structure 1256 (e.g., encoded differently and/or having different wavelengths). Seeking 1400 can allow the robot 11 to navigate by choosing actions that provide the best chance of moving from one landmark to the next, stringing together a path that ends at a goal location, such as the maintenance station 1250.

Detecting 1404 the maintenance station 1250 includes detecting a change in the received signal 1252' emitted by the maintenance station 1250. At time t1', for example, the change in the received signal 1252' is a change from receiving the signal 1252' to not receiving the signal 1252'. As another example, at time t4', the change in the received signal 1252' is a change from not receiving the signal 1252' to receiving the signal 1252'.

Detecting 1406 the second structure 1256 includes detecting a change in the received signal 1256 emitted by the second structure 1256. At time t2', for example, the change in the received signal 1258 is a change from not receiving the signal 1258 to receiving the signal 1258. As another example, at time t3', the change in the received signal 1258 is a change from receiving the signal 1258 to not receiving the signal 1258.

Determining 1408 the probability that the robot 11 will find the maintenance station 1250 within a period of time is based at least in part upon the elapsed time between detecting 1404 the maintenance station 1250 and detecting 1406 the second structure 1256. For example, the elapsed time is the difference between t2' and t1' and the probability determination is the probability that the robot 11 will find the maintenance station 1250 given that the second structure 1256 has just been detected. The determination 1408 of the probability that the robot 11 will find the maintenance station 1250 within a period of time can be analogous to the determination 1308 discussed above.

In some implementations, the maintenance station 1250 is a first lighthouse (e.g., when the battery 25 is fully charged) and the second structure 1256 is a second lighthouse such that the robot 11 moves along the cleaning surface 1 based on relative positioning to the maintenance station 1250 and/or to the second structure 1256.

FIGS. 19A-G show another implementation of an autonomous robotic cleaner. Features identified by reference symbols including a prime are analogous to features identified by corresponding unprimed reference symbols in the implementations described above, unless otherwise specified. Thus, for example, robot 11' is analogous to robot 11 and bin 50' is analogous to bin 50.

Figure 19A:
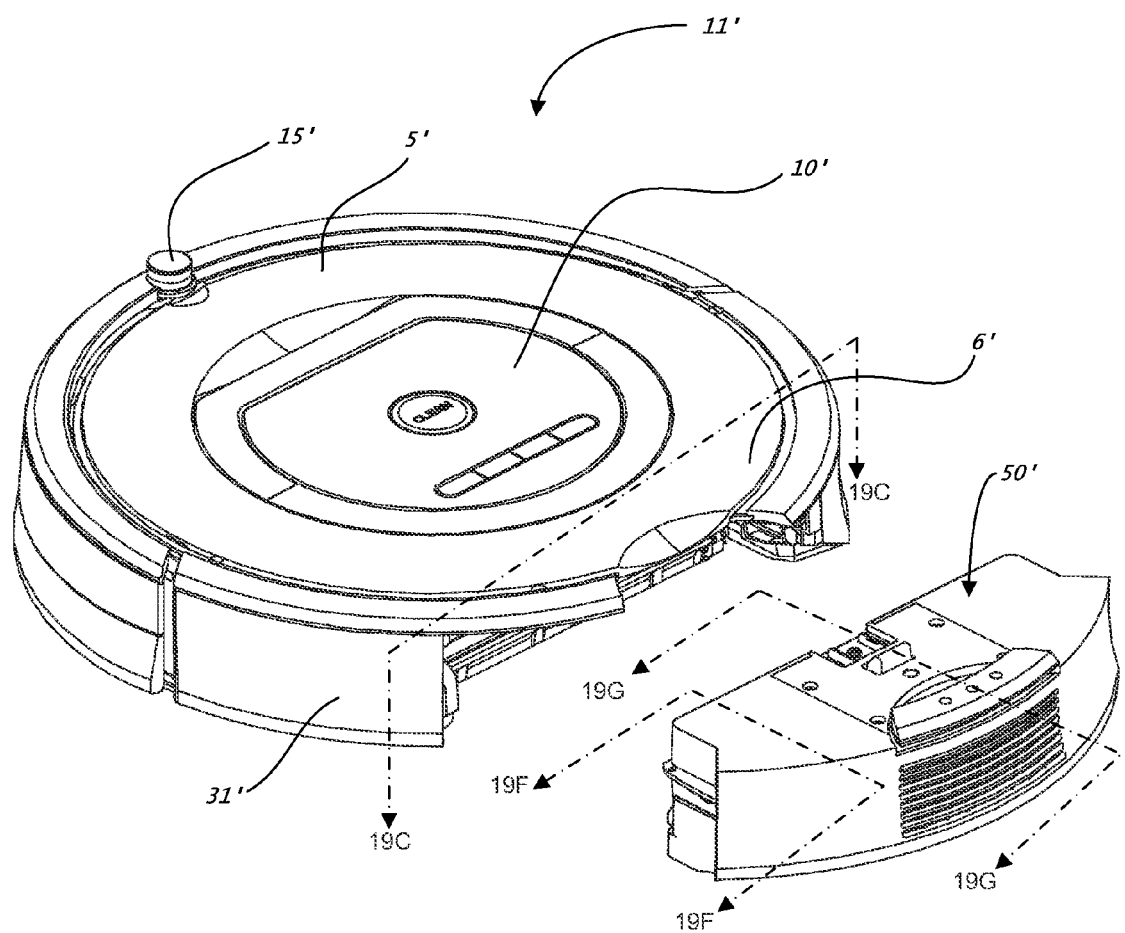
FIG. 19A is a partially exploded, top perspective view of an autonomous robotic cleaner.
Figure 19B:
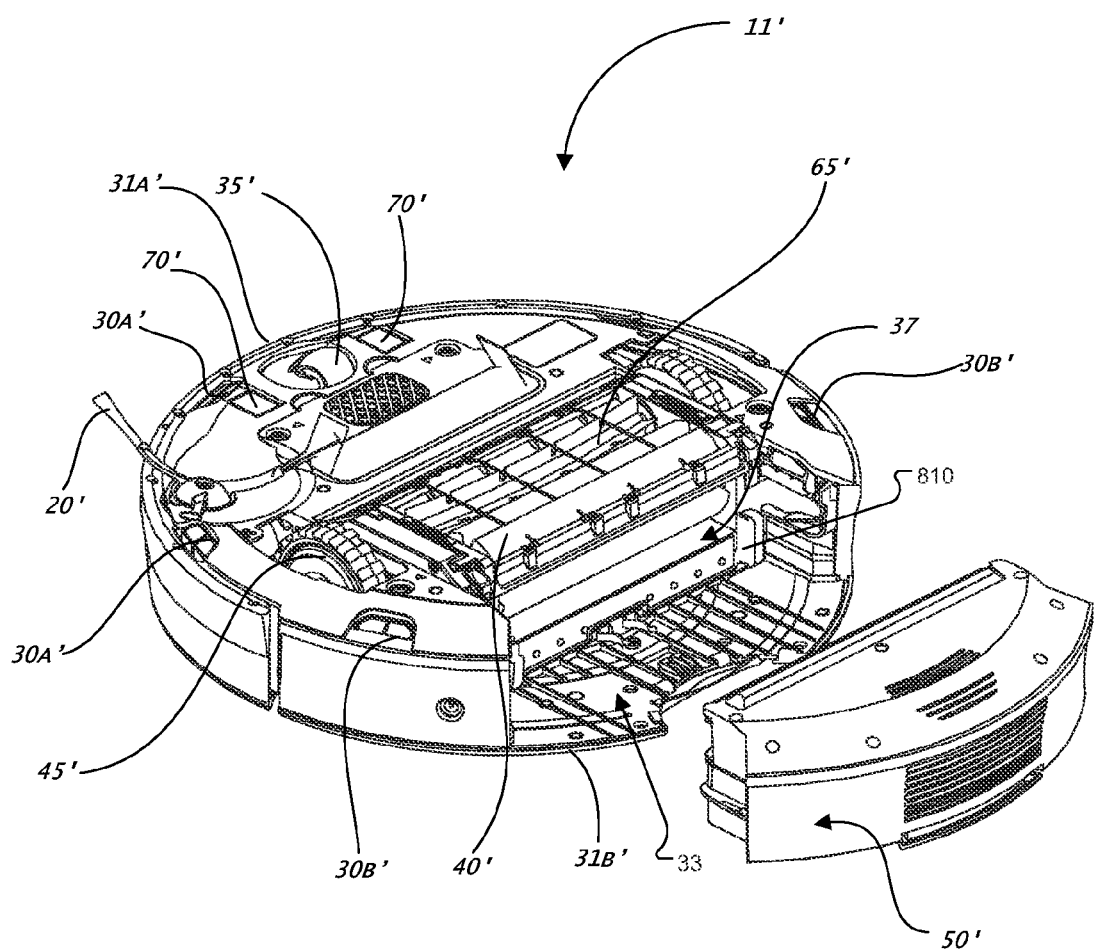
FIG. 19B is a partially exploded, bottom perspective view of the autonomous robotic cleaner of FIG. 19A.
Figure 19C:
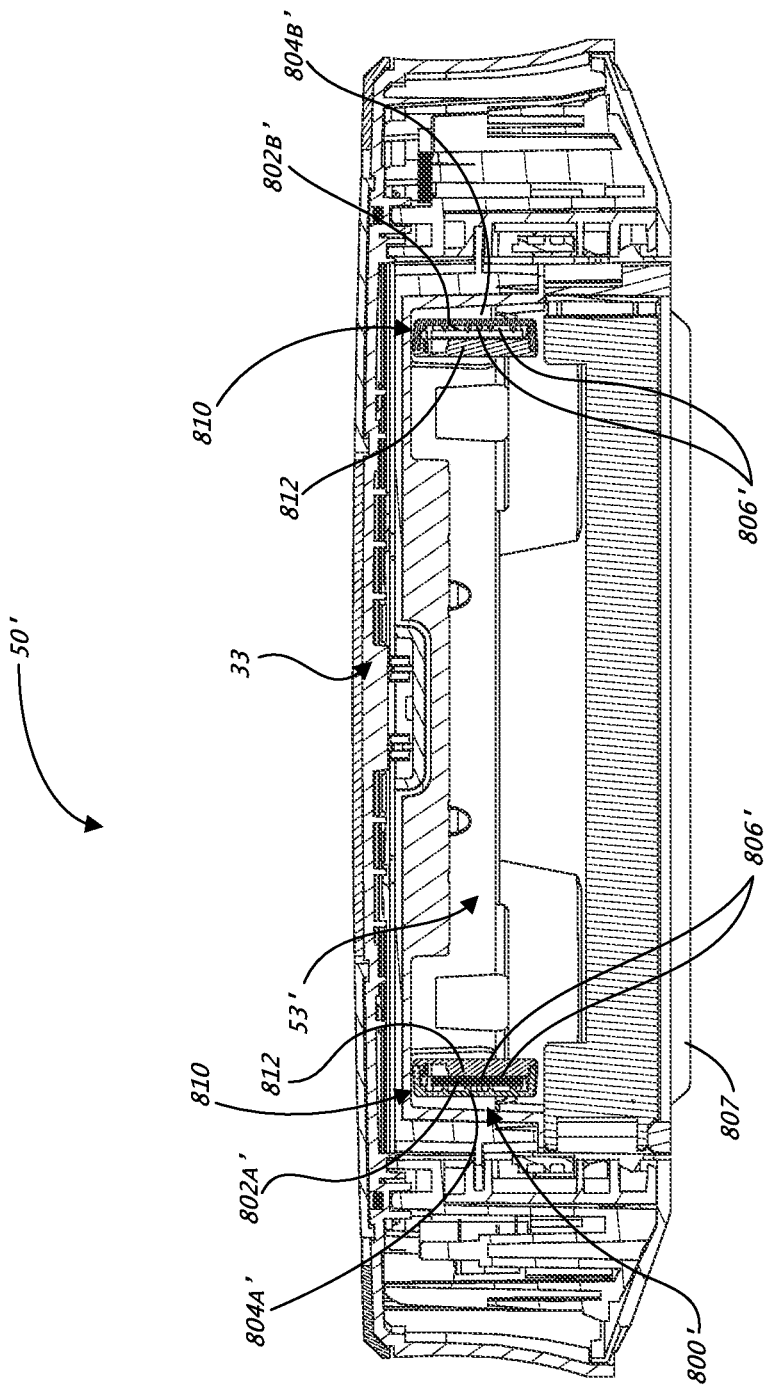
FIG. 19C is a cross-sectional front view of the autonomous robotic cleaner of FIG. 19A in an unexploded configuration, taken along the line 19C-19C.
Figure 19D:
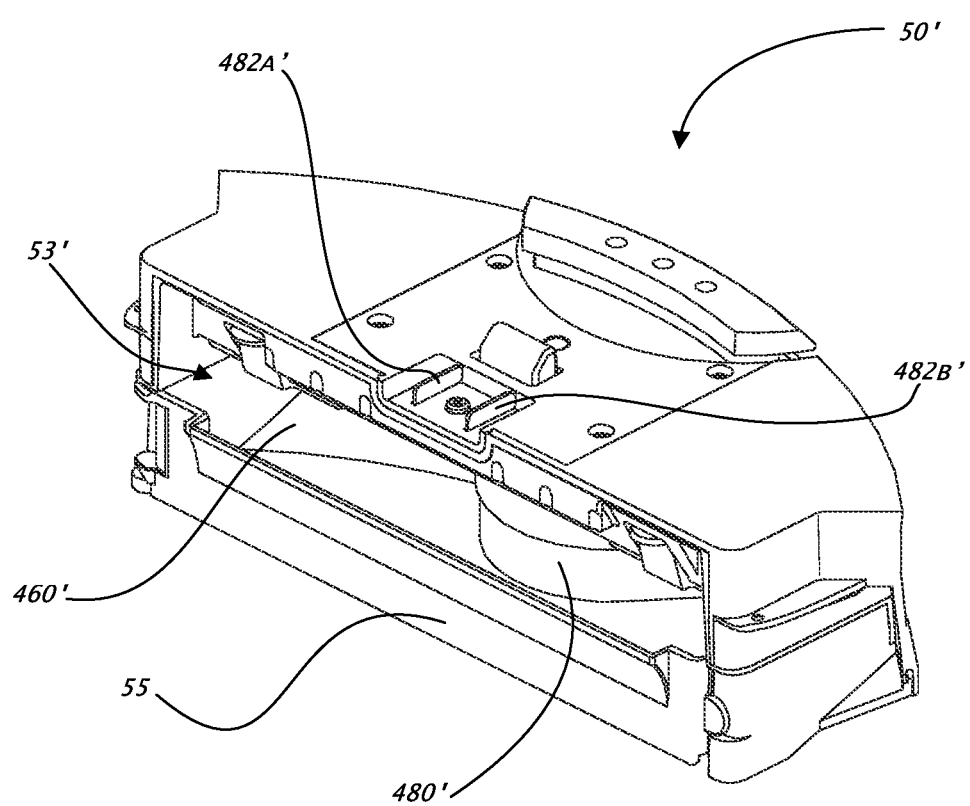
FIG. 19D is a perspective view of the dust bin of the autonomous robotic cleaner of FIG. 19A.
Figure 19E:
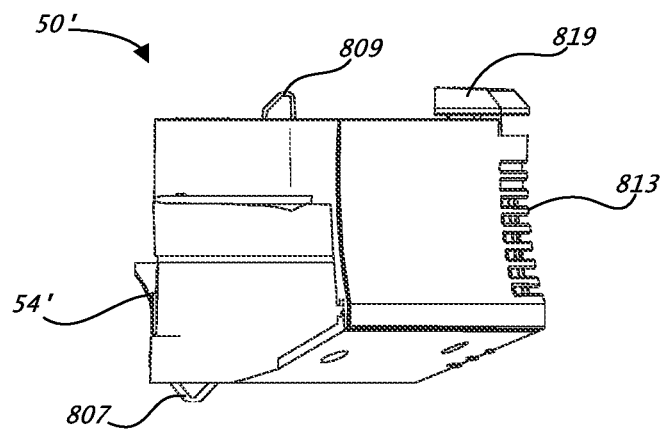
FIG. 19E is a side view of the dust bin of the autonomous robotic cleaner of FIG. 19A.
Figure 19F:
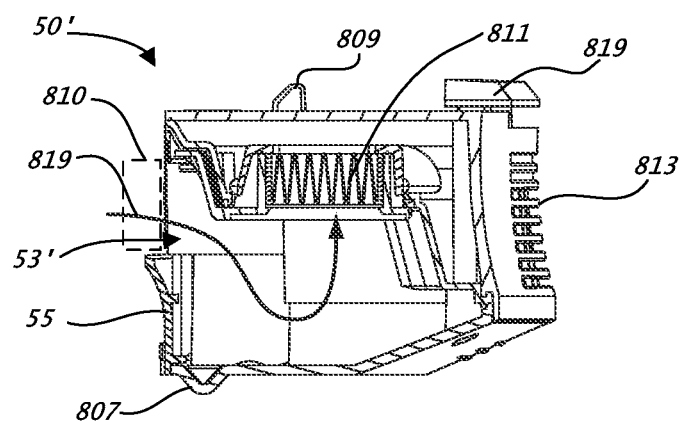
FIG. 19F is a cross-section of the dust bin of the autonomous robotic cleaner of FIG. 19A, taken along the line 19F-19F.
Figure 19G:
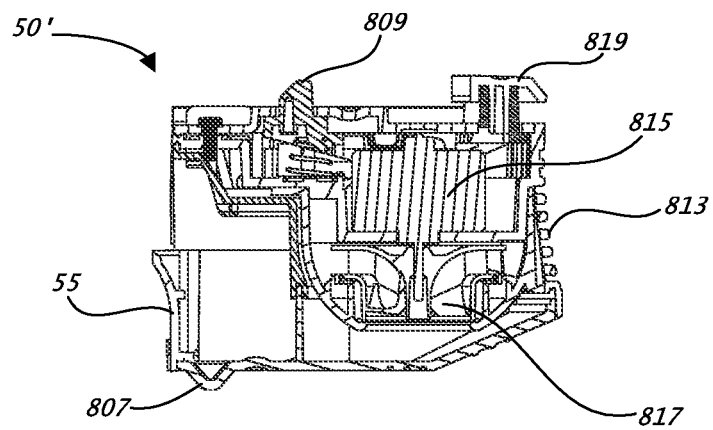
FIG. 19G is a cross-section of the dust bin of the autonomous robotic cleaner of FIG. 19A, taken along the line 19G-19G.

A bin guide 33 defines at least a portion of a receiving volume 37 defined by the robot body 31'. Bin 50' is movable (e.g., slidable) along bin guide 33 to lock into place (e.g., as described below) such that mouth 53' of bin 50' aligns with a top portion of the receiving volume 37. For example, such alignment is shown in FIG. 8A, FIGS. 19C, and 19F. FIG. 19C is a cross-sectional view taken through robot 11', along the receiving volume 37, with bin 50' inserted in the receiving volume 37. Accordingly, as shown in FIG. 19C, for example, debris moves past infrared array assemblies 810 disposed along a top portion of receiving volume 37 and into mouth 53' defined by bin 50'. Such movement is shown schematically in FIG. 19F, for example, in which the position of infrared array assembly 810 (which is disposed along the receiving volume 37 of the robot 11' and, thus, represented as a dashed line in FIG. 19F) is shown relative to mouth 53' defined by bin 50'.

Each infrared array assembly 810 includes an emitter array (first emitter array 804A' or second emitter array 804B', as shown in FIG. 19C), with each respective emitter array including two light sources 806'. Each infrared array assembly 810 also includes a receiver (first receiver 802A' or a second receiver 802B', as shown in FIG. 19C) and a filter 812 disposed between the receiving volume 37 and the respective emitter array and receiver of the infrared array assembly 810. Each filter 812 can be an infrared transparent daylight filter.

Although each infrared array assembly 810 is shown as disposed along receiving volume 37 defined by robot body 31', each infrared array assembly 810 can be disposed on bin 50'. Whether the infrared array assembly 810 is disposed on the receiving volume 37 or the bin 50', the first and second receivers 802A', 802B' and the first and second emitter arrays 804A', 804B' can be substantially evenly spaced across the mouth 53' on each horizontal side of the mouth 53' to substantially span horizontal and vertical dimensions of the mouth 53' with emitted light from the array assemblies 810.

Robot 11' includes a dust bin 50' for collecting debris while the robot 11' is in operation. The dust bin 50' is releasably detachable from the robot 11' (e.g., releasably detachable from the robot body 31') to allow debris to be removed from the dust bin 50' and/or to allow a filter 811 carried by the dust bin 50' to be replaced. The dust bin 50' can be removed from robot 11' by moving a release 819 (e.g., depressing the release 819 and/or lifting the release 819) that moves a latch 809 such that the dust bin 50' can be slidably removed from the robot 11'. In some implementations, release 819 can include one or more lights (e.g., lights indicative of an operating mode of the robot 11') and/or one or more proximity sensors. In certain implementations, release 819 senses the position of the latch 809 such that release 819 provides an indication of the position of the bin 50' (e.g., an indication that the bin 50' is not fully engaged with the robot 11').

The bin 50' includes a barrier 55 which extends horizontally across the width of the bin 50' and extends vertically along at least a portion of the bin 50' such that the barrier 55 defines at least a portion of a horizontal bottom portion of the mouth 53'. In some implementations, barrier 55 defines at least a portion of a compartment that retains debris settled at the bottom of the bin 50' when the bin is in situ in the robot 11'. In certain implementations, at least a portion of the barrier 55 is a door (e.g., a hinged door and/or a slidable door) that is movable to allow access to debris stored in the bin 50'. In some implementations, the barrier 55 is rigidly fixed relative to the mouth 53' and access to debris is obtained through one or more doors forming part of a side wall, a bottom wall, or a rear wall of the bin 50'.

In some implementations, the vertical dimension of the mouth 53' is substantially ½ or less of the combined height of the barrier 55 and the vertical dimension of the mouth 53'. Accordingly, in implementations in which the height of the bin 50' is defined approximately by the combined vertical dimensions of the mouth 53' and the barrier 55, the vertical dimension of the barrier 55 can be greater than the vertical dimension of the mouth 53'. These relative dimensions of the barrier 55 to the mouth 53' can facilitate storage of a large amount of debris in the bin 50' while retaining the profile of the robot 11' during use.

Although the mouth 53' and the barrier 55 are shown as extending substantially across the entire width of the bin 50', other configurations are also possible. For example, the mouth 53' can extend about ⅔ of the width of the bin 50' or less while the barrier 55 extends substantially across the entire width of the bin 50' such that the width of the barrier 55 is at least ⅓ greater than the width of the mouth 53'. These relative dimensions of the barrier 55 to the mouth 53' can facilitate storage of a large amount of debris in the bin 50' while retaining the profile of the robot 11' during use.

Although the bin 50' is shown as defining a mouth 53' having a single opening, other implementations are also possible. For example, the bin 50' may define a mouth having multiple openings which can facilitate increasing turbulence along the flow path 819 (FIG. 19F) and/or facilitate breaking up large pieces of debris as it moves along the flow path 819. For example, the bin 50' may define a mouth having two openings horizontally spaced apart from one another. More generally, as used herein, the term mouth refers to the total open area through which debris passes into the bin 50' during operation.

The bin 50' includes a protrusion 807 disposed toward an end portion of the bin 50' that engaged with the robot 11'. The protrusion 807 can engage with robot 11' to reduce the likelihood of damage to portions of the bin 50' as the bin 50' is slid into engagement with the robot 11'. For example, the protrusion 807 can reduce the likelihood of damage to the door 54' and/or to the release 819 as the bin 50' is slid into the robot 11'. Additionally or alternatively, the protrusion 807 can facilitate alignment of the latch 809 for securing the bin 50' to the robot 11'.

The bin 50' further includes a filter 811, a motor 815, and an impeller 817. During use, a fluid stream 819 (e.g., debris carried in air) is drawn into the bin 50' by negative pressure created by rotation of the impeller 817 driven by the motor 815. The fluid stream 819 moves past the optical detection system 800' such that debris detection and bin-full detection can be carried out as described above. The fluid stream 819 moves through a filter 811 such that the debris is separated from the air, with the debris remaining in the bin 50' (e.g., in a portion of the bin 50' at least partially defined by barrier 55) and the air exiting the bin 50' through an exhaust 813 defined by the bin 50'.

An optical detection system 800' is similar to optical detection system 800 and operates to detect debris and bin-full conditions in a manner analogous to the debris and bin-full detection described above with respect to FIGS. 8A-8E. In general, the views shown in FIGS. 8A-8E correspond to the front view of the bin 50' shown in FIG. 19C. As shown in FIG. 19C, the mouth 53' defined by the bin 50' extends along only part of the vertical dimension of the bin 50'. Thus, to further illustrate the correspondence in structure between the bin 50 shown in FIG. 8A and the bin 50' shown in FIG. 19C, the position of the mouth 53' is shown as dashed line in FIG. 8A.

Accordingly, it should be appreciated that the detection of the debris 48 shown in FIG. 8B is analogous to the debris detection of debris entering bin 50' through mouth 53', along path 819. Similarly, it should be appreciated that the bin-full detection as a result of the accumulation 49 of debris shown in FIG. 8C is analogous to the bin-full detection of an accumulation of debris in a compartment defined by the bin 50'. Likewise, it should be further appreciated that the detection of asymmetric debris accumulation shown in FIGS. 8D and 8E is analogous to the detection of asymmetric debris accumulation in a compartment defined by the bin 50'.

Other details and features combinable with those described herein may be found in U.S. patent application Ser. No. 11/751,267, filed May 21, 2007, entitled Coverage Robots and Associated Cleaning Bins, and U.S. patent application Ser. No. 10/766,303, filed Jan. 28, 2004, entitled Debris Sensor for Cleaning Apparatus, now U.S. Pat. No. 6,956,348. The entire contents of each of the aforementioned applications are hereby incorporated by reference in their entirety.

A number of implementations have been described. Nevertheless, it will be understood that various modifications may be made without departing from the spirit and scope of the disclosure. Accordingly, other implementations are within the scope of the following claims.

What is claimed is:

1. A debris monitoring system comprising:
   a housing;
   a receptacle defining an opening, the receptacle being releasably engageable with the housing to receive debris into the receptacle through the opening;
   a first emitter supported on the housing on one side of the opening and arranged to emit a signal across at least a portion of the opening; and
   a first receiver supported on the housing on an opposite side of the opening and arranged to receive the signal emitted by the first emitter across the opening;
   wherein the receptacle is movable with respect to the first emitter and the first receiver.

2. The debris monitoring system of claim 1 wherein the opening is substantially rectangular and the first receiver and the first emitter are substantially opposed to one another across the opening.

3. The debris monitoring system of claim 1 further comprising a second emitter arranged to direct a signal across the opening.

4. The debris monitoring system of claim 3 wherein the first and second emitter are arranged relative to one another such that their respective signals intersect within the opening.

5. The debris monitoring system of claim 1 wherein the first receiver is less than about 0.25 inches from the first emitter.

6. The debris monitoring system of claim 3 wherein the second emitter is supported on the housing and the receptacle is movable relative to the second emitter.

7. The debris monitoring system of claim 1 further comprising a controller supported on the housing, wherein the first emitter and the first receiver are each in wireless communication with the controller.

8. The debris monitoring system of claim 7 wherein the wireless communication comprises infrared communication.

9. A debris monitoring system comprising:
   a housing;
   a receptacle configured to be carried by the housing and defining an opening to receive debris into the receptacle;
   a plurality of first emitters and a plurality of second emitters, each emitter of each plurality of emitters arranged to emit a signal across at least a portion of the opening and positioned on the housing adjacent the receptacle;
   a first receiver positioned on an opposite side of the opening from the plurality of first emitters to receive reflections of the signal emitted by each of the plurality of first emitters and the first receiver disposed toward the opening to receive an unreflected portion of the signal emitted by each of the plurality of second emitters across at least a portion of the opening; and
   a second receiver positioned on an opposite side of the opening from the plurality of second emitters to receive reflections of the signal emitted by each of the plurality of second emitters and the second receiver disposed toward the opening to receive an unreflected portion of the signal emitted by each of the plurality of first emitters across at least a portion of the opening.

10. The debris monitoring system of claim 9 further comprising a controller configured to pulse the plurality of first emitters on and off and to pulse the plurality of second emitters on and off.

11. The debris monitoring system of claim 10 wherein the controller is further configured to sample of each of the first and second receivers synchronously such that a first sample of each receiver is taken when the plurality of first emitters and the plurality of second emitters are off, a second sample of each receiver is taken when the plurality of first emitters is on and the plurality of second emitters is off, and a third sample of each receiver is taken when the plurality of first emitters is off and the plurality of second emitters is on.

12. The debris monitoring system of claim 9 wherein the plurality of first emitters and the plurality of second emitters are arranged relative to one another such that the signals emitted by the plurality of first emitters intersect the signals emitted by the plurality of second emitters, the intersection being along at least a portion of the opening.

13. The debris monitoring system of claim 12 wherein the plurality of first emitters and the plurality of second emitters are arranged relative to one another such that the signals emitted by the plurality of first emitters intersect the signals emitted by the plurality of second emitters along a line substantially bisecting the opening.

14. The debris monitoring system of claim 9 wherein the plurality of first emitters and the plurality of second emitters are spaced relative to one another such that the signals emitted by the plurality of first emitters and the plurality of second emitters span substantially all of the area of the opening when all of the emitters from each of the plurality of first and second emitters are on.

* * * * *